(12) United States Patent
Hoehn et al.

(10) Patent No.: US 11,896,591 B2
(45) Date of Patent: Feb. 13, 2024

(54) COMPOSITIONS AND METHODS FOR PREPARING AND USING MITOCHONDRIAL UNCOUPLERS

(71) Applicants: UNIVERSITY OF VIRGINIA PATENT FOUNDATION, Charlottesville, VA (US); VIRGINIA TECH INTELLECTUAL PROPERTIES, INC., Blacksburg, VA (US); NEWSOUTH INNOVATIONS PTY LIMITED, Sydney (AU)

(72) Inventors: Kyle Hoehn, Charlottesville, VA (US); Webster L. Santos, Blacksburg, VA (US); Elizabeth S. Childress, Christiansburg, VA (US); Yumin Dai, Blacksburg, VA (US); Jacob Murray, Blacksburg, VA (US); Jose Santiago-Rivera, Blacksburg, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 18 days.

(21) Appl. No.: 16/615,567

(22) PCT Filed: May 22, 2018

(86) PCT No.: PCT/US2018/033901
§ 371 (c)(1),
(2) Date: Nov. 21, 2019

(87) PCT Pub. No.: WO2018/217757
PCT Pub. Date: Nov. 29, 2018

(65) Prior Publication Data
US 2020/0323846 A1    Oct. 15, 2020

Related U.S. Application Data

(60) Provisional application No. 62/509,249, filed on May 22, 2017.

(51) Int. Cl.
*A61K 31/4985* (2006.01)
*C07D 498/04* (2006.01)
(Continued)

(52) U.S. Cl.
CPC ...... *A61K 31/4985* (2013.01); *A61K 31/4965* (2013.01); *A61P 3/04* (2018.01);
(Continued)

(58) Field of Classification Search
None
See application file for complete search history.

(56) References Cited

FOREIGN PATENT DOCUMENTS

| WO | 2007008541 A2 | 1/2007 |
| WO | 2008021389 A2 | 2/2008 |

(Continued)

OTHER PUBLICATIONS

Chemical Abstract Registry No. 392315-46-7, indexed in the Registry File on STN CAS Online Feb. 14, 2002.*

(Continued)

*Primary Examiner* — Po-Chih Chen
(74) *Attorney, Agent, or Firm* — CANTOR COLBURN LLP

(57) ABSTRACT

This disclosure provides compounds of Formula I, II, and III and pharmaceutically acceptable salts thereof for use as mitochondrial uncouplers, where the variables, e.g. $R^1$-$R^9$,

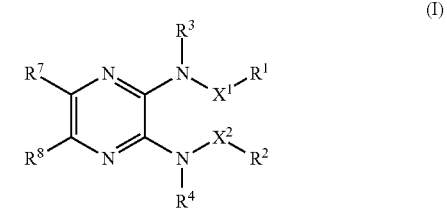

(I)

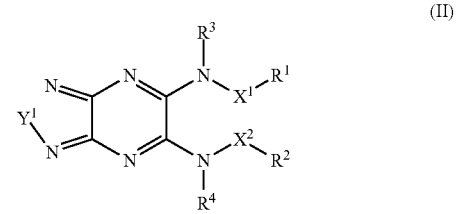

(II)

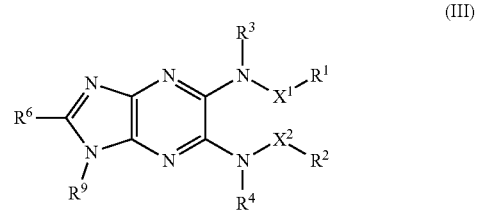

(III)

$X^1$, $X^2$, and $Y^1$ are defined in the specification. The disclosure also provides pharmaceutical compositions comprising a compound or pharmaceutically acceptable salt of Formula I, II, or III, alone or in combination with another active compound. Compounds and compositions of Formula I, II, and III are useful for treating or preventing certain conditions such as obesity, type II diabetes, fatty liver disease, insulin resistance, Parkinson's disease, ischemia reperfusion injury, heart failure, non-alcoholic fatty liver disease (NALFD), and non-alcoholic steatohepatitis (NASH). Compounds of Formula I, II, and III are also useful for regulating glucose homeostatis and insulin action.

11 Claims, 7 Drawing Sheets

(51) Int. Cl.
| | |
|---|---|
| C07D 487/04 | (2006.01) |
| C07D 241/20 | (2006.01) |
| A61P 3/04 | (2006.01) |
| A61K 31/4965 | (2006.01) |

(52) U.S. Cl.
CPC ......... *C07D 241/20* (2013.01); *C07D 487/04* (2013.01); *C07D 498/04* (2013.01)

(56) References Cited

FOREIGN PATENT DOCUMENTS

| WO | 2011073149 A1 | 6/2011 |
|---|---|---|
| WO | 2013192388 A1 | 12/2013 |

OTHER PUBLICATIONS

Chemical Abstract Registry No. 1797876-98-2, indexed in the Registry File on STN CAS Online Jul. 9, 2015.*
Goedeke et al., Therapeutic potential of mitochondrial uncouplers for the treatment of metabolic associated fatty liver disease and NASH. Molecular Metabolism, 2021, 46, p. 1-14.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Chemical Abstract Registry No. 299921-36-1, indexed in the Registry File on STN CAS Online Oct. 27, 2000.*
Fernandez et al., Solid-phase versus solution synthesis of asymmetrically disubstituted furazano[4,5-b]pyrazines. Tetrahedron Letters, 2002, 43, 4741-4745.*
Chemical Abstract Registry No. 330996-20-8, indexed in the Registry file on STN CAS Online Apr. 12, 2001.*
International Search Report; International Application No. PCT/US2018/033901; International Filing Date—May 22, 2018; DATED Nov. 6, 2018; 10 pages.
Kenwood et al., "Structure-Activity Relationships of Furazano[3,4-b]Pyrazines as Mitochondrial Uncouplers," Bioorganic & Medicinal Chemistry Letters, vol. 25, No. 21, Nov. 1, 2015; pp. 4858-4861, XP055414210, (Eng. abstract only).
Kumar et al., "Structural Insight into Inhibition of Human Class II PI3K Isoforms: Homology Modeling, Binding Site Characterization, Docking and Molecular Dynamics Studies," RSC Advances, vol. 6, No. 113, Jan. 1, 2016; pp. 112455-112467, XP055495576, (Eng. abstract only).
McDonald et al., "Pyrazine Chemistry. II. Derivatives of 3-hydroxpyrazinoic Acid," Journal of American Chemical Society (1947), p. 69.
Written Opinion; International Application No. PCT/US2018/033901; International Filing Date—May 22, 2018; dated Nov. 6, 2018; 21 pages.
Ding, S., et al. "A Combinatorial Scaffold Approach Toward Kinase-Directed Heterocycle Libraries," Retrieved from STN, Chemical Abstracts Service, Database Accession No. 2002:96165, (2002), 2 pages, Abstract Only.
Elderfield, R., et al. "Potential Anticancer Agents. IV. Synthesis of Substituted Amino- and Aziridinopyrimidines" Retrieved from STN, Chemical Abstracts Service, Database Accession No. 1961:43305, (1961) 4 pages, Abstract Only.
International Preliminary Report on Patentability; International Application No. PCT/US2018/033901; International Filing Date—May 22, 2018; dated Nov. 26, 2019; 20 pages.
Xiang, J., "Synthesis of 5, 6-bis(4-ethoxyanilino)-2-3-Dicyanopyrazines," Retrieved from STN, Chemical Abstracts Service, Database Accession No. 1998:656606, (1998,) 2 pages. Abstract Only.
Childress et al., "[1,2,5]Oxadiazolo[3,4-b]pyrazine-5,6-diamine Derivatives as Mitochondrial Uncouplers for the Potential Treatment of Nonalcoholic Steatohepatitis," J. Med. Chem. (2020), vol. 63, (No. 5); 1-43.
Ellingson et al., "Pyrazine Chemistry. III. Derivatives of 3-Amino-5,6-dimethylpyrazinoic Acid," Journal of American Chemical Society, (1948), vol. 70, 1257-1261.
Freitag et al., "Development of First Lead Structures for Phosphoinositide 3-Kinase-C2, [gamma] Inhibitors," Journal of Medicinal Chemistry, (2015), vol. 58, 212-221.
Starchenkov et al., "Chemistry of Furazano[3,4-b] Pyrazines 3.* Method for the Synthesis of 5,6-Disubstituted Furazano[3,4-b] Pyrazines," Chemistry of Heterocyclic Compounds, (1997), vol. 33, (No. 10), 1218-1233.
Islam et al., "Chemical Constituents of Essential Oil from the Leaf of Alpinia Nigra of Bangladesh," International Food Research Journal, (2014), vol. 21, (No. 1), 161-164.

* cited by examiner

COMPOSITIONS AND METHODS FOR PREPARING AND USING MITOCHONDRIAL UNCOUPLERS

CROSS REFERENCE TO RELATED APPLICATION

This application is a National Stage application of PCT/2018/033901, filed May 22, 2018, which claims priority to U.S. Provisional application No. 62/509,249, filed May 22, 2017, and all the benefits accruing therefrom under 35 U.S.C. § 119, the content of which is incorporated by reference in its entirety.

STATEMENT REGARDING FEDERALLY SPONSORED RESEARCH OR DEVELOPMENT

This invention was made with government support under Grant No. DK101803, awarded by The National Institutes of Health. The U.S. government has certain rights in the invention.

BACKGROUND

In 2013, the American Medical Association declared obesity as a disease. In the US, 68.8% of adults are overweight (body mass index, BMI>25) 36.5% of US adults are obese (BMI>30). Obesity is a major risk factor for metabolic diseases including diabetes, cardiovascular disease, fatty liver disease, and many forms of cancer. The estimated annual health care cost of obesity-related illness is $149B. While diet and exercise are effective treatments, these interventions have poor patient compliance.

Pharmacologic agents can complement diet and exercise regimens for reducing obesity. Mitochondrial uncouplers are one drug class known to be effective for producing weight loss in humans. For example, 2,4-dinitrophenol (DNP) is a well-known small molecule mitochondrial protonophore that results in weight loss in humans. Patients consuming ~300 mg/d steadily shed an average of 1.5 pounds per week over the course of several months without changes in food intake. Similarly, mice treated with DNP demonstrate improved serological glucose, triglyceride, and insulin levels, as well as decreased oxidative damage, reduced body weight, and increased longevity. However, DNP has a very narrow therapeutic window. As with any weight loss drugs, there is high risk of over-consumption for faster weight loss.

The mechanism of mitochondrial uncoupling is inherently an antioxidant mechanism and consequently mitochondrial uncouplers such as DNP have protective effects on ischemia-reperfusion injury and other disorders related to mitochondrial reactive oxygen species production. Unfortunately, DNP has off-target effects on other cellular membranes resulting in a narrow therapeutic index. DNP was subsequently withdrawn from the North American market by the US Food and Drug Administration in 1938. Currently, there are no uncoupler drugs that are safe enough for use in humans. The development of mitochondrial small molecule protonophores with excellent safety profiles could return these anti-obesity drugs to the marked after nearly 80 years' absence.

Mitochondrial ATP production is derived from nutrient oxidation via a proton gradient across the mitochondrial inner membrane. Nutrient oxidation results in proton efflux from the matrix to create a 10-fold proton gradient across the mitochondrial inner membrane. That is, the inner membrane space pH is ~6.9 and the mitochondrial matrix pH is ~8.0. ATP production occurs when protons re-enter the mitochondrial matrix via ATP synthase, thereby 'coupling' nutrient oxidation to ATP production. In contrast, protons that re-enter the matrix via other routes 'uncouple' nutrient oxidation from ATP production. Increasing 'uncoupling' prevents mitochondrial hyperpolarization, decreases reactive oxygen species production, and can increase weight loss by causing the cell to burn more nutrients (consumption of calories) to produce a given amount of ATP.

Mitochondrial protonophore uncouplers are small molecules that transfer protons across the mitochondrial inner membrane (MIM). These molecules are referred to as 'uncouplers' because they allow protons to re-enter the mitochondrial matrix via a pathway independent of ATP synthase and, therefore, uncouple nutrient oxidation from ATP production. Pharmacologic uncouplers, when used at optimal concentrations, improve the efficiency of the mitochondrial electron transport chain and decrease mitochondrial reactive oxygen species (ROS) production. The major limitation of DNP and other protonophore uncouplers is their unwanted protonophore activity at other membranes including the plasma membrane (PM). This off-target activity increases intracellular acidification, depolarizes electrically stimulated cells, and increases energy demand needed to maintain cellular ion gradients. When these off-target effects are combined with reduced efficiency of mitochondrial ATP production, the side effects include over-heating and ATP depletion. This clinical history with DNP overdose has led to the misconception that all mitochondrial uncouplers will cause these side effects.

Mitochondria play an important role in the pathogenesis of some of the most prevalent human diseases including obesity, cancer, diabetes, neurodegeneration, and heart disease. Many of these diseases can be improved by the use of pharmacological agents like mitochondrial proton transporters that lessen mitochondrial oxidative damage and increase energy expenditure. Genetic and pharmacologic uncoupling have beneficial effects on disorders that are linked to mitochondrial oxidative stress, such as ischemic-reperfusion injury, Parkinson's disease, insulin resistance, aging, and heart failure, and disorders that stand to benefit from increased energy expenditure such as obesity. The development of a selective mitochondrial protonophore uncoupler that does not affect the plasma membrane potential would broaden the safety margin of mitochondrial uncouplers and provide renewed hope that mitochondrial uncoupling can be targeted for the treatment of obesity, fatty liver disease, type II diabetes, and other diseases, disorders, and conditions related to mitochondrial function.

There is a long felt need in the art for compositions and methods useful for preventing and treating obesity, diabetes, fatty liver disease, regulating glucose homeostasis, reducing adiposity, protecting from ischemic-reperfusion injury, and regulating insulin action using mitochondrial uncouplers as well as for compounds useful as mitochondrial uncouplers.

SUMMARY

This disclosure provides compounds useful for preventing and treating obesity and other disease and disorders and methods for making and testing these compounds as well as identifying and making new compounds with similar biological activity.

These unprecedented properties have been long sought after and provide great potential for the treatment of mitochondria-related disorders, including, but not limited to, obesity, diabetes, fatty liver disease, insulin resistance, Parkinson's disease, aging, traumatic brain injury, ischemia-reperfusion injury, and heart failure.

This disclosure provides compounds useful as mitochondrial uncouplers, pharmaceutical compositions containing such compounds, and methods of using the compounds to treat diseases and conditions including obesity, type II diabetes, fatty liver disease, insulin resistance, Parkinson's disease, ischemia reperfusion injury, heart failure, non-alcoholic fatty liver disease (NALFD), and non-alcoholic steatohepatitis (NASH), or for regulating glucose homeostasis or insulin action.

Compounds of this disclosure are useful for preventing or reducing the incidence diet-induced glucose intolerance, liver fat accumulation, and diet-induced adiposity in patients at risk for such conditions and for increasing respiration and increasing fat oxidation in subjects in need thereof.

Thus in a first aspect the disclosure provides compounds of Formula I, and the pharmaceutically acceptable salts of Formula I.

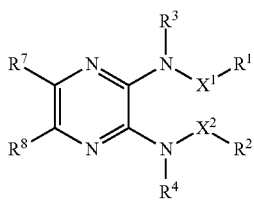

(I)

Within Formula I the variables, $R^1$, $R^2$, $R^3$, $R^4$, $R^7$ $R^8$, $X^1$, and $X^2$ carry the following definitions.

$R^1$ and $R^2$ are the same or different and are each independently mono- or bicyclic aryl, mono- or bicyclic heteroaryl, cycloalkyl, or heterocycloalkyl, each of which is unsubstituted or substituted with one or more groups independently selected from halogen, hydroxyl, amino, nitro, cyano, —CHO, —COOH, $C_1$-$C_8$alkyl, $C_2$-$C_8$alkenyl, $C_2$-$C_8$alkynyl, and —($C_0$-$C_4$alkylene)cycloalkyl.

$X^1$ and $X^2$ are the same or different and are absent (a covalent bond), —CH$_2$—, —C(O)—, —S(O)—, or S(O)$_2$—.

$R^3$ and $R^4$ are each independently hydrogen or $C_1$-$C_4$alkyl.

$R^7$ and $R^8$ are each independently hydrogen, halogen, hydroxyl, amino, nitro, cyano, —CHO, —COOH, $C_1$-$C_6$alkyl, $C_2$-$C_8$alkenyl, $C_2$-$C_8$alkynyl, —($C_0$-$C_4$alkylene)cycloalkyl, —($C_0$-$C_4$alkylene)heterocycloalkyl, —($C_0$-$C_4$alkylene)phenyl, or —($C_0$-$C_4$alkylene)heteroaryl which cycloalkyl, heterocycloalkyl, phenyl, or heteroaryl is unsubstituted or substituted with one or more substituents independently selected from halogen, hydroxyl, amino, nitro, cyano, —CHO, —COOH, and $C_1$-$C_6$alkyl;

Each alkyl, alkenyl, alkynyl, or alkylene in the definition of $R^1$ and $R^2$ is unsubstituted or substituted with one or more substituents independently chosen from halogen, hydroxyl, amino, nitro, cyano, —CHO, and —COOH, and one or more methylene units in any alkyl, alkenyl, alkynyl, or alkylene is optionally replaced by O, NR, —C(O)—, —C(O)O—, —S(O)n—, —C(O)NR$^5$—, or —NR$^5$C(O)— where n is 0, 1, or 2, and $R^8$ is independently chosen at each occurrence from hydrogen, $C_1$-$C_6$alkyl, and ($C_0$-$C_2$alkyl)cycloalkyl.

$N^2$,$N^3$-bis(2-fluorophenyl)pyrazine-2,3-diamine is excluded from the scope of Formula I.

The disclosure further provides compounds of Formula II and the pharmaceutically acceptable salts of Formula II.

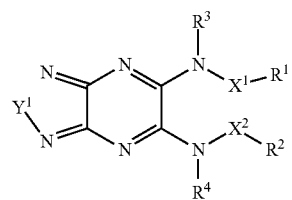

(II)

Within Formula II the variables, $R^1$, $R^2$, $R^3$, $R^4$, $X^1$, $X^2$, and Y carry the following definitions.

$R^1$ and $R^2$ are the same or different and are each independently $C_1$-$C_8$alkyl, mono- or bicyclic aryl, mono- or bicyclic heteroaryl, cycloalkyl, or heterocycloalkyl, each of which is unsubstituted or substituted with one or more groups independently selected from halogen, hydroxyl, amino, nitro, cyano, —CHO, —COOH, $C_1$-$C_8$alkyl, $C_2$-$C_8$alkenyl, $C_2$-$C_8$alkynyl, and —($C_0$-$C_4$alkylene)cycloalkyl, where each alkyl, alkenyl, alkynyl, or alkylene in the definitions of $R^1$ and $R^2$ is unsubstituted or substituted with one or more substituents independently chosen from halogen, hydroxyl, amino, nitro, cyano, —CHO, or —COOH, and one or more methylene units in any alkyl, alkenyl, alkynyl, or alkylene is optionally replaced by O, NR$^5$, —C(O)—, —C(O)O—, —S(O)n—, —C(O)NR$^5$—, or —NR$^5$C(O)— where n is 0, 1, or 2, and $R^8$ is independently chosen at each occurrence from hydrogen, $C_1$-$C_6$alkyl, and ($C_0$-$C_2$alkyl)cycloalkyl.

$X^1$ and $X^2$ are the same or different and are absent (a covalent bond), —CH$_2$—, —C(O)—, —S(O)—, or S(O)$_2$—.

$R^3$ and $R^4$ is hydrogen or $C_1$-$C_4$alkyl.

$Y^1$ is S or O.

When $X^1$ and $X^2$ are both absent, $R^1$ and $R^2$ are not both unsubstituted $C_1$-$C_8$alkyl.

The following compounds are excluded from the scope of Formula II:

(2-fluorophenyl){6-[(2-fluorophenyl)amino](1,2,5-oxadiazolo[3,4-e]pyrazine-5-yl)}amine (BAM15);

(4-chlorophenyl){6-[(4-chlorophenyl)amino](1,2,5-oxadiazolo[3,4-e]pyrazine-5-yl)}amine (BAM8);

(4-fluorophenyl){6-[(4-fluorophenyl)amino](1,2,5-oxadiazolo[3,4-e]pyrazine-5-yl)}amine (BAM9);

(2-chlorophenyl){6-[(2-chlorophenyl)amino](1,2,5-oxadiazolo[3,4-e]pyrazine-5-yl)}amine (BAM15A);

(2-bromophenyl){6-[(2-bromophenyl)amino](1,2,5-oxadiazolo[3,4-e]pyrazine-5-yl)}amine (BAM15B);

(2-iodophenyl){6-[(2-iodophenyl)amino](1,2,5-oxadiazolo[3,4-e]pyrazine-5-yl)}amine (BAM15C);

(2-fluoro, 4-chlorophenyl){6-[(2-fluoro, 4-chlorophenyl)amino](1,2,5-oxadiazolo[3,4-e]pyrazine-5-yl)}amine (BAM15D);

(2,4-difluorophenyl){6-[(2,4-difluorophenyl)amino](1,2,5-oxadiazolo[3,4-e]pyrazine-5-yl)}amine (BAM15 F);

(2-fluorophenyl){6-[(4-fluorophenyl)amino](1,2,5-oxadiazolo[3,4-e]pyrazine-5-yl)}amine;

(2-methoxyphenyl){6-[(2-methoxyphenyl)amino](1,2,5-oxadiazolo[3,4-e]pyrazine-5-yl)}amine;

(3-methoxyphenyl){6-[(3-methoxyphenyl)amino](1,2,5-oxadiazolo[3,4-e]pyrazine-5-yl)}amine;

(3-trifluoromethylphenyl){6-[(3-trifluoromethylphenyl)amino](1,2,5-oxadiazolo[3,4-e]pyrazine-5-yl)}amine;

(2-fluoromethylphenyl){6-[(4-methylphenyl)amino](1,2,5-oxadiazolo[3,4-e]pyrazine-5-yl)}amine;

dimethyl 4,4'-([1,2,5]oxadiazolo[3,4-b]pyrazine-5,6-diylbis(azanediyl))dibenzoate;
(3-methylphenyl){6-[(3-methylphenyl)amino](1,2,5-oxadiazolo[3,4-e]pyrazine-5-yl)}amine;
(2-methylphenyl){6-[(2-methylphenyl)amino](1,2,5-oxadiazolo[3,4-e]pyrazine-5-yl)}amine;
(4-methylphenyl){6-[(4-methylphenyl)amino](1,2,5-oxadiazolo[3,4-e]pyrazine-5-yl)}amine;
(4-cyanophenyl){6-[(cyanophenyl)amino](1,2,5-oxadiazolo[3,4-e]pyrazine-5-yl)}amine;
(4-methoxyphenyl){6-[(4-methoxyphenyl)amino](1,2,5-oxadiazolo[3,4-e]pyrazine-5-yl)}amine;
4,4'-([1,2,5]oxadiazolo[3,4-b]pyrazine-5,6-diylbis(azanediyl))dibenzoic acid;
dimethyl 2,2'-([1,2,5]oxadiazolo[3,4-b]pyrazine-5,6-diylbis(azanediyl))dibenzoate;
(2-fluorophenyl){6-[(4-methoxyphenyl)amino](1,2,5-oxadiazolo[3,4-e]pyrazine-5-yl)}amine;
or (4-trifluoromethylphenyl){6-[(4-trifluoromethylphenyl)amino](1,2,5-oxadiazolo[3,4-e]pyrazine-5-yl)}amine.

In yet another aspect the disclosure provides compounds of Formula III, and the pharmaceutically acceptable salts thereof.

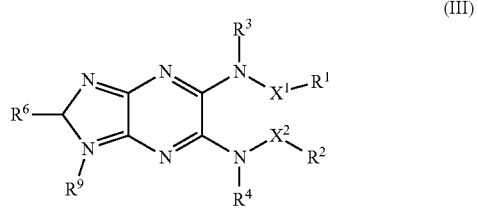

(III)

Within Formula III the variables, $R^1$, $R^2$, $R^3$, $R^4$, $R^6$, $R^9$, $X^1$, and $X^2$, carry the following definitions.

$R^1$ and $R^2$ are each independently mono- or bicyclic aryl, mono- or bicyclic heteroaryl, cycloalkyl, and heterocycloalkyl, each of which is unsubstituted or substituted with one or more groups independently selected from halogen, hydroxyl, amino, nitro, cyano, —CHO, —COOH, $C_1$-$C_8$alkyl, $C_2$-$C_8$alkenyl, $C_2$-$C_8$alkynyl, and —($C_0$-$C_4$alkylene)cycloalkyl.

In $R^1$ and $R^2$ each alkyl, alkenyl, alkynyl, or alkylene is unsubstituted or substituted with one or more substituents independently chosen from halogen, hydroxyl, amino, nitro, cyano, —CHO, and —COOH, and one or more methylene units in any alkyl, alkenyl, alkynyl, or alkylene is optionally replaced by O, $NR^5$, —C(O)—, —C(O)O—, —S(O)n—, —C(O)$NR^5$—, or —$NR^5$C(O)— where n is 0, 1, or 2, and $R^5$ is independently chosen at each occurrence from hydrogen, $C_1$-$C_6$alkyl, and ($C_0$-$C_2$alkyl)cycloalkyl.

$X^1$ and $X^2$ are the same or different and are absent (a covalent bond), —$CH_2$—, —C(O)—, —S(O)—, or $S(O)_2$—.

$R^3$ and $R^4$ is hydrogen or $C_1$-$C_4$alkyl.

$R^6$ is hydrogen, $C_1$-$C_4$alkyl, $C_1$-$C_2$haloalkyl, $C_1$-$C_2$haloalkoxy, or phenyl.

$R^9$ is hydrogen, $C_1$-$C_4$alkyl, or $C_1$-$C_4$alkylester.

DETAILED DESCRIPTION

Terminology

Figure 1:
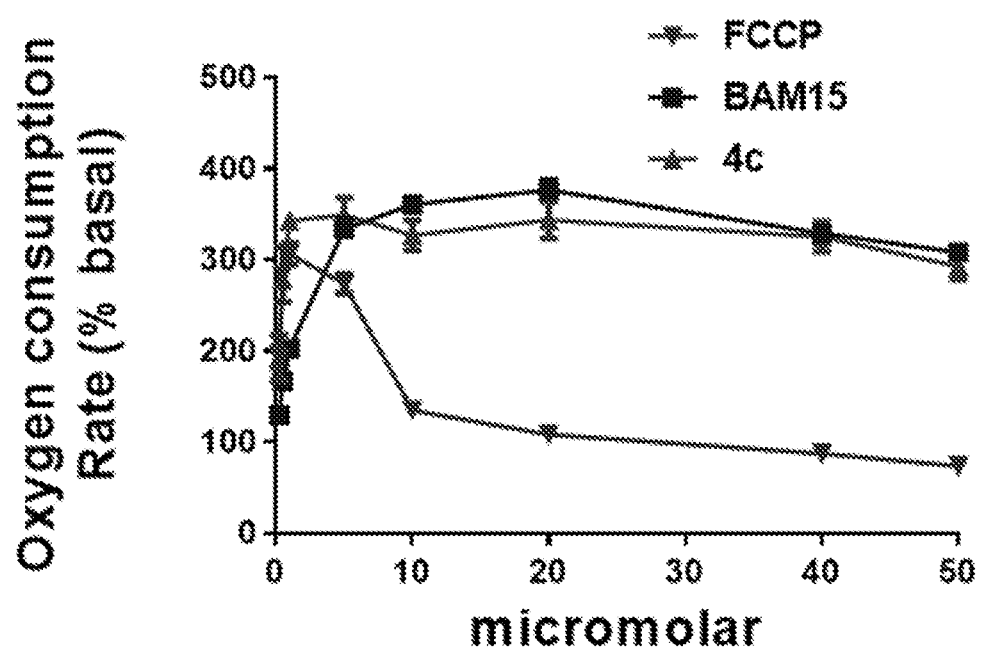
FIG. 1. Oxygen consumption rate as a function of drug dose. Compound 4c exhibits produces a higher oxygen consumption rate than mitochondrial uncouplers, BAM15 or FCCP.

In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below. The terms "a" and "an" do not denote a limitation of quantity, but rather denote the presence of at least one of the referenced item. The term "or" means "and/or". The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the terms "administration of" and or "administering" a compound should be understood to mean providing a compound of the disclosure or a prodrug of a compound of the invention to a subject in need of treatment.

As used herein, "alleviating a disease or disorder symptom," means reducing the severity of the symptom or the frequency with which such a symptom is experienced by a subject, or both.

The terms "comprises," "comprising," and the alternate transitional phrases "includes," "including," "contain," and "containing" are open ended transitional phrases having the meaning ascribed to them in U.S. Patent Law. "Comprises" and the other open ended terms encompass the intermediate term "consisting essentially of" and the closed ended terms "consisting of" and "consists of." Claims reciting one of the open-ended transitional phrases can be written with any other transitional phrase, which may be more limiting, unless clearly precluded by the context or art.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used in the specification and the appended claims, the terms "for example," "for instance," "such as," "including" and the like are meant to introduce examples that further clarify more general subject matter. Unless otherwise specified, these examples are provided only as an aid for understanding, and are not meant to be limiting in any fashion.

The terms "formula" and "structure" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

As used herein, "health care provider" includes either an individual or an institution that provides preventive, curative, promotional or rehabilitative health care services to a subject, such as a patient.

"Injecting or applying" includes administration of a compound by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

"Instructional material" includes a publication, a recording, a diagram, or any other medium of expression which can be used to communicate the usefulness of invention compound of the disclosure in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains the identified compound of the disclosure or be shipped together with a container which contains the identified compound. Alternatively, the instructional material may be shipped separately from the container with the intention that the instructional material and the compound be used cooperatively by the recipient.

The term, "mitochondrial uncoupling", also referred to as "uncoupling", refers to the process whereby protons enter the mitochondrial matrix via a pathway independent of ATP synthase and thereby uncouple nutrient oxidation from ATP production. This process can be pharmacologically induced by small molecule mitochondrial protonophores, which directly shuttle protons across the mitochondrial inner membrane into the matrix. The primary pathway for energy production in aerobic cells involves the oxidation of nutrients (including fats, carbohydrates, and amino acids) in mitochondria, which promotes the efflux of protons out of the mitochondrial matrix. This process creates a pH and electrochemical gradient across the mitochondrial inner membrane. Protons normally re-enter the mitochondrial matrix via ATP synthase, which results in ATP production. Protons can also re-enter the mitochondrial matrix via pathways independent of ATP synthase, which 'uncouples' nutrient oxidation and proton efflux from ATP production.

The term "modulate", as used herein, refers to changing the level of an activity, function, or process. The term "modulate" encompasses both inhibiting and stimulating an activity, function, or process.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

"Pharmaceutical compositions" are compositions comprising at least one active agent, such as a compound or salt, solvate, or hydrate of Formula (I) or a prodrug thereof, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as a Gram-negative bacterial infection. "Pharmaceutical compositions" includes compositions for human and animal (veterinary) use.

"Pharmaceutically acceptable carrier" applied to pharmaceutical compositions/combinations of the disclosure refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The term also encompasses any of the agents approved by a regulatory agency of the US Federal government or listed in the US Pharmacopeia for use in animals, including humans.

"Pharmaceutically acceptable" means physiologically tolerable, for either human or veterinary application.

"Plurality" means at least two.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this disclosure.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, "treat," "treating", or "treatment" includes treating, ameliorating, or inhibiting an injury or disease related condition or a symptom of an injury or disease related condition. In one embodiment the disease, injury or disease related condition or a symptom of an injury or disease related condition is prevented; while another embodiment provides prophylactic treatment of the injury or disease related condition or a symptom of an injury or disease related condition.

Chemical Definitions

Compounds are described using standard nomenclature. Unless defined otherwise, all technical and scientific terms used herein have the same meaning as is commonly understood by one of skill in the art to which this disclosure belongs. Unless clearly contraindicated by the context, each compound name includes the free acid or free base form of the compound as well as all pharmaceutically acceptable salts, solvates, and hydrates of the compound.

The terms "Formula I," "Formula II," and "Formula III" encompasses all compounds that satisfy these formulae, including any enantiomers, racemates and stereoisomers, as well as all pharmaceutically acceptable salts, solvates, and hydrates of such compounds. "Formula I" includes all subgeneric groups of Formula I unless clearly contraindicated by the context in which this phrase is used, likewise for Formula II and Formula III.

Compounds of Formula I, II, and III include all compounds of Formula I, II, and III having isotopic substitutions at any position. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C. In some embodiments, any one or more hydrogen atoms are replaced with deuterium atoms.

A dash ("-") that is not between two letters or symbols is used to indicate a point of attachment for a substituent. For example, —C(O)NH$_2$ is attached through carbon of the keto C(O) group.

"Alkyl" is a branched or straight chain saturated aliphatic hydrocarbon group, having the specified number of carbon atoms, generally from 1 to about 8 carbon atoms. The term $C_1$-$C_6$-alkyl as used herein indicates an alkyl group having from 1, 2, 3, 4, 5, or 6 carbon atoms. Other embodiments include alkyl groups having from 1 to 6 carbon atoms, 1 to 4 carbon atoms or 1 or 2 carbon atoms, e.g. $C_1$-$C_8$-alkyl, $C_1$-$C_4$-alkyl, and $C_1$-$C_2$-alkyl. Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more double carbon-carbon bonds that may occur at any stable point along the chain, having the specified number of carbon atoms. Examples of alkenyl include, but are not limited to, ethenyl and propenyl.

"Alkynyl" is a branched or straight chain aliphatic hydrocarbon group having one or more triple carbon-carbon bonds that may occur at any stable point along the chain, having the specified number of carbon atoms. Examples of alkynyl include, but are not limited to, ethynyl and propynyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkylester" is an alkyl group as defined herein covalently bound to the group it substitutes by an ester linkage.

The ester linkage may be in either orientation, e.g., a group of the formula —OC(O)-alkyl or a group of the formula —C(O)O-alkyl.

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Aryl groups include, for example, phenyl, naphthyl, including 1-naphthyl, 2-naphthyl, and bi-phenyl.

"Cycloalkyl" is a saturated hydrocarbon ring group, having the specified number of carbon atoms. Monocyclic cycloalkyl groups typically have from 3 to about 8 carbon ring atoms or from 3 to 6 (3, 4, 5, or 6) carbon ring atoms. Cycloalkyl substituents may be pendant from a substituted nitrogen, oxygen, or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl.

"Halo" or "halogen" indicates any of fluoro, chloro, bromo, and iodo.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, 2,2,2-trifluoroethyl, and penta-fluoroethyl.

"Haloalkoxy" indicates a haloalkyl group as defined herein attached through an oxygen bridge (oxygen of an alcohol radical).

The term "heterocycle" indicates a monocyclic saturated, partially unsaturated, or aromatic ring containing from 1 to 4 heteroatoms chosen from N, O, and S, with remaining ring atoms being carbon, or a bicyclic saturated, partially unsaturated, or aromatic heterocycle containing at least 1 heteroatom chosen from N, O, and S in one of the two rings of the two ring system and containing up to about 4 heteroatoms independently chosen from N, O, and S in each ring of the two ring system. Usually each ring of the heterocycle contains from 4-6 ring atoms but some other number of ring atoms may be specified. Unless otherwise indicated, the heterocycle may be attached to its pendant group at any heteroatom or carbon atom that results in a stable structure. When indicated the heterocycles described herein may be substituted on carbon, sulfur, or nitrogen atom if the resulting compound is stable. It is preferred that the total number of heteroatoms in a heterocycle is not more than 4 and that the total number of S and O atoms in a heterocycle is not more than 2, more preferably not more than 1. Examples of heterocycles include, pyridyl, indolyl, pyrimidinyl, pyridazinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyrazolyl, pyrrolidinyl, morpholinyl, piperazinyl, piperidinyl, and pyrrolidinyl. In certain embodiments a heterocycle is chosen from pyridinyl, pyrimidinyl, furanyl, thienyl, and pyrrolyl.

Additional examples of heterocycles include, but are not limited to, phthalazinyl, indolizinyl, indazolyl, benzothiazolyl, benzimidazolyl, benzofuranyl, benzoisoxolyl, dihydrobenzodioxinyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, 5 pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocumarinyl, chromanyl, tetrahydroquinolinyl, dihydroquinolinyl, dihydroquinolinonyl, dihydroisoquinolinonyl, dihydrocumarinyl, dihydroisocumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N oxide, indazolyl N-oxide, benzothiazolyl N-oxide, benzimidazolyl N-oxide, pyrrolyl N-oxide, oxadiazolyl N-oxide, thiadiazolyl N-oxide, tetrazolyl N-oxide, benzothiopyranyl S-oxide, and benzothiopyranyl S,S-dioxide.

"Heterocycloalkyl" refers to a heterocycle as defined above but does not include aromatic or unsaturated rings, thus it is composed of a saturated ring or rings. Examples of heterocycloalkyls include tetrahydropyranyl, tetrahydrofuranyl, piperidinyl, piperazinyl, morpholinyl, thiomorpholinyl, oxazolidinyl, tetrahydrothiophenyl, tetrahydrothiopyranyl, thiazolidinyl, and pyrrolidinyl.

"Heteroaryl" is a stable monocyclic aromatic ring having the indicated number of ring atoms which contains from 1 to 4, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 4, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridazinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxinyl, furanyl, imidazolyl, indolyl, and isoxazolyl.

The term "substituted" means that any one or more hydrogens on the designated atom or group is replaced with a selection from the indicated group, provided that the designated atom's normal valence is not exceeded. When the substituent is oxo (i.e., $=O$) then 2 hydrogens on the atom are replaced. When an oxo group substitutes a heteroaromatic moiety, the resulting molecule can sometimes adopt tautomeric forms. For example a pyridyl group substituted by oxo at the 2- or 4-position can sometimes be written as a pyridine or hydroxypyridine. Combinations of substituents and/or variables are permissible only if such combinations result in stable compounds or useful synthetic intermediates.

A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group.

Suitable groups that may be present on a "substituted" or "optionally substituted" position include, but are not limited to, e.g., halogen; cyano; —OH; oxo; —NH$_2$; nitro; azido; alkanoyl (such as a C$_2$-C$_6$ alkanoyl group); C(O)NH$_2$; alkyl groups (including cycloalkyl and (cycloalkyl)alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; mono- or dialkylamino groups including groups having alkyl groups from 1 to about 6 carbon atoms; mono- or dialkylaminocarbonyl groups (i.e. alkylNHCO— or (alkyl1)(alkyl2)NCO—) having alkyl groups from about 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocycle having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocycles may be further substituted, e.g. with hydroxy, alkyl, alkoxy, halogen and amino. In certain embodiments "optionally substituted" includes one or more substituents independently chosen from halogen, hydroxyl, oxo, amino, cyano, —CHO, —CO$_2$H, —C(O)NH$_2$, C$_1$-C$_6$-alkyl, C$_2$-C$_6$-alkenyl, C$_1$-C$_6$-alkoxy, C$_2$-C$_6$-alkanoyl, C$_1$-C$_6$-alkylester, (mono- and di-C$_1$-C$_6$-alkylamino)C$_0$-C$_2$-alkyl, (mono- and di-C$_1$-C$_6$-alkylamino)(CO)C$_0$-C$_2$-alkyl, C$_1$-C$_2$-haloalkyl, C$_1$-C$_2$haloalkoxy, and heterocyclic substituents of 5-6 members and 1 to 3 N, O or S atoms, i.e. pyridyl, pyrazinyl, pyrimidinyl, furanyl, pyrrolyl, thienyl, thiazolyl, triazinyl, oxazolyl, isoxazolyl, imidazolyl, tetrahydrofuranyl, tetrahydropyranyl, piperidinyl, morpholinyl, piperazinyl, and pyrrolidinyl, each of which heterocycle can be substituted by amino, C$_1$-C$_6$-alkyl, C$_1$-C$_6$-alkoxy, or —CONH$_2$.

"Halogen" or "halo" includes bromo, chloro, fluoro, and iodo.

"Haloalkyl" is an alkyl radical bearing at least one halogen substituent, for example, chloromethyl, fluoroethyl or trifluoromethyl and the like.

In certain situations, the compounds of any of Formula I, II, and III may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column. In addition, compounds with carbon-carbon double bonds may occur in Z- and E-forms, with all isomeric forms of the compounds being included in the present disclosure.

Where a compound exists in various tautomeric forms, the disclosure is not limited to any one of the specific tautomers, but rather includes all tautomeric forms. The compounds of the disclosure may exist in tautomeric forms. both mixtures and separate individual tautomers are included. For example, the following structure:

is understood to represent a mixture of the structures:

as well as

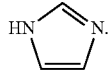

Certain compounds are described herein using a general formula that includes variables, e.g. R$^1$-R$^9$. Unless otherwise specified, each variable within such a formula is defined independently of other variables. Thus, if a group is said to be substituted, e.g. with 0-2 R*, then the group may be substituted with up to two R* groups and R* at each occurrence is selected independently from the definition of R*. Also, combinations of substituents and/or variables are permissible only if such combinations result in stable compounds.

Abbreviations

The following abbreviations are used in the specification including in the examples.

| | |
|---|---|
| AMPK | AMP-activated protein kinase |
| Ar | aryl |
| BMI | body mass index |
| DNP | 2,4-dinitrophenol |
| Et | ethyl |
| $Et_3N$ | triethylamine |
| FCCP | carbonyl cyanide p-trifluoromethoxyphenylhydrazone |
| HBA | hydrogen bond acceptor |
| HBD | hydrogen bond donor |
| HOAc | acetic acid |
| MIM | mitochondrial inner membrane |
| NaOtBu | sodium tert-butoxide |
| OCR | oxygen consumption rate |
| $Pd(dba)_2$ | Palladium(0) bis(dibenzylideneacetone) |
| Ph | phenyl |
| PM | plasma membrane |
| rac-BINAP | (±)-2,2'-bis(diphenylphosphino)-1,1'-binaphthalene |
| ROS | reactive oxygen species |
| THF | tetrahydrofuran |
| TMPD | N,N,N',N'-Tetramethyl-p-phenylenediamine |
| UCP | uncoupling protein |
| WD | western diet |

Chemical Description

In addition to compounds and salts of Formula I set forth in the SUMMARY section, the disclosure provides compounds and pharmaceutically acceptable salts of Formula I in which the variables, $R^1$, $R^2$, $R^3$, $R^4$, $R^7$, $R^8$, $X^1$, and $X^2$ carry any of the following definitions. Any of the following definitions of variables may be combined so long as a stable compound results. It should be noted that for each embodiment of compounds of Formula I the exclusion of $N^2,N^3$-bis(2-fluorophenyl)pyrazine-2,3-diamine applies. Thus the disclosure includes compounds and salts of Formula I

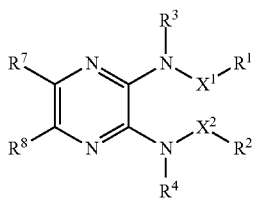

(I)

in which one or more of the following conditions are met:
(a) $X^1$ and $X^2$ are both absent.
(b) $X^1$ and $X^2$ are both —$CH_2$—.
(c) $R^3$ and $R^4$ are independently hydrogen or methyl.
(d) $R^3$ and $R^4$ are both hydrogen.
(e) $R^7$ and R are independently chosen from hydrogen, halogen, cyano, COOH, $C_1$-$C_4$alkoxy, and $C_1$-$C_4$alkyl.
(f) $R^7$ and R are both hydrogen.
(g) $R^1$ and $R^2$ are both phenyl, each of which are both substituted with at least one substituent chosen from halogen, cyano, amino, —COOH, —NHC(O)$CF_3$, $C_1$-$C_2$alkoxy, $C_1$-$C_4$alkylester, trifluoromethyl, trifluoromethoxy, and optionally substituted with one or more additional substituents independently selected from hydroxyl, nitro, —CHO, $C_1$-$C_8$alkyl, $C_2$-$C_8$alkenyl, $C_2$-$C_8$alkynyl, and —($C_0$-$C_4$alkylene)cycloalkyl, where each alkyl, alkenyl, alkynyl, or alkylene is unsubstituted or substituted with one or more substituents independently chosen from halogen, hydroxyl, amino, nitro, cyano, —CHO, or —COOH, and one or more methylene units in any alkyl, alkenyl, alkynyl, or alkylene is optionally replaced by O, NR, —C(O)—, —C(O)O—, —S(O)n—, —C(O)$NR^5$—, or —$NR^5$C(O)— where n is 0, 1, or 2, and $R^5$ is independently chosen at each occurrence from hydrogen, $C_1$-$C_6$alkyl, and ($C_0$-$C_2$alkyl)cycloalkyl.

(h) $R^1$ are $R^2$ both phenyl and are each substituted with one or two substituents chosen from fluoro, amino, —C(O)OCH$_3$, —NHC(O)$CF_3$, —COOH, methyl, methoxy, ethoxy, trifluoromethyl, and trifluoromethoxy.
(i) $R^1$ and $R^2$ are the same.
(j) $R^1$ and $R^2$ are different.
(k) $R^1$ and are R are chosen from 2-fluorophenyl, 2,4-difluorophenyl, 3-methylphenyl, 2-methoxyphenyl, 3-methoxyphenyl, 4-methoxyphenyl, 4-ethoxyphenyl, 2-trifluoromethoxyphenyl, 3-trifluoromethoxyphenyl, 4-acetamide-phenyl, and 4-COOH-phenyl.
(k) $R^1$ and $R^2$ are the same or different and are each chosen from mono- or bicyclic aryl, mono- or bicyclic heteroaryl, cycloalkyl, and heterocycloalkyl, each of which is substituted with one or more groups independently selected from halogen, hydroxyl, amino, nitro, cyano, —CHO, —COOH, $C_1$-$C_8$alkyl, $C_2$-$C_8$alkenyl, $C_2$-$C_8$alkynyl, and —($C_0$-$C_4$alkylene)cycloalkyl, with the proviso that one of $R^1$ and $R^2$ is substituted with a substituent that is not unsubstituted $C_1$-$C_8$alkyl;
$X^1$ and $X^2$ are the same or different and are absent (a covalent bond), —$CH_2$—, —C(O)—, S(O)—, or S(O)$_2$—;
$R^3$ and $R^4$ are each independently hydrogen or $C_1$-$C_4$alkyl; and
$R^7$ and $R^8$ are each independently hydrogen, halogen, hydroxyl, amino, nitro, cyano, —CHO, —COOH, $C_1$-$C_8$alkyl, $C_2$-$C_8$alkenyl, $C_2$-$C_8$alkynyl, —($C_0$-$C_4$alkylene)cycloalkyl, and —($C_0$-$C_4$alkylene)phenyl;
where each alkyl, alkenyl, alkynyl, or alkylene is unsubstituted or substituted with one or more substituents independently chosen from halogen, hydroxyl, amino, nitro, cyano, —CHO, or —COOH, and one or more methylene units in any alkyl, alkenyl, alkynyl, or alkylene is optionally replaced by O, NR, —C(O)—, —C(O)O—, —S(O)n—, —C(O)$NR^5$—, or —$NR^5$C(O)— where n is 0, 1, or 2, and $R^8$ is independently chosen at each occurrence from hydrogen, $C_1$-$C_8$alkyl, and ($C_0$-$C_2$alkyl)cycloalkyl; and where $N^2,N^3$-bis(2-fluorophenyl)pyrazine-2,3-diamine is excluded.
(l) $R^1$ and $R^2$ are both phenyl, each of which are both substituted with at least one substituent chosen from halogen, cyano, amino, —COOH, —NHC(O)$CF_3$, $C_1$-$C_2$alkoxy, $C_1$-$C_4$alkylester, trifluoromethyl, trifluoromethoxy, and optionally substituted with one or more additional substituents independently selected from hydroxyl, nitro, —CHO, $C_1$-$C_8$alkyl, $C_2$-$C_8$alkenyl, $C_2$-$C_8$alkynyl, and —($C_0$-$C_4$alkylene)cycloalkyl, where each alkyl, alkenyl, alkynyl, or alkylene is unsubstituted or substituted with one or more substituents independently chosen from halogen, hydroxyl, amino, nitro, cyano, —CHO, and —COOH, and one or more methylene units in any alkyl, alkenyl, alkynyl, or alkylene is optionally replaced by O, NR, —C(O)—, —C(O)O—, —S(O)n—, —C(O)$NR^5$—, or —$NR^5$C(O)— where n is 0, 1, or 2, and $R^5$ is independently chosen at each occurrence from hydrogen, $C_1$-$C_8$alkyl, and ($C_0$-$C_2$alkyl)cycloalkyl;

X¹ and X² are either absent or —CH₂—;
R³ and R⁴ are either hydrogen or methyl;
R⁷ and R⁸ are both hydrogen.

As a particular example, Formula I includes compound 100, methyl (3-((2-fluorophenyl)amino)-5-(2-methoxyphenyl)pyrazin-2-yl)(4-(2,2,2-trifluoroethoxy)-2-(trifluoromethyl)phenyl)carbamate, and its pharmaceutically acceptable salts.

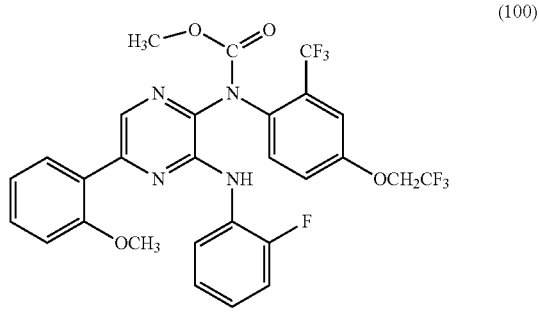

(100)

In addition to compounds and salts of Formula II set forth in the SUMMARY section, the disclosure provides compounds and pharmaceutically acceptable salts of Formula I in which the variables, R¹, R², R³, R⁴, X¹, X², and Y¹ carry any of the following definitions. Any of the following definitions of variables may be combined so long as a stable compound results. It should be noted that for each embodiment the exclusion the list of oxadiazolopyrazine provides in the SUMMARY section for Formula II applies.

Thus the disclosure includes compounds and salts of Formula II

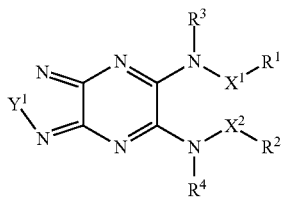

(II)

in which one or more of the following conditions are met:
(a) X¹ and X² are both absent, —NHS(O)₂—, or —NHC(O)—.
(b) X¹ and X² are both absent.
(c) X¹ and X² are both —NHS(O)₂—.
(d) X¹ and X² are both —NHC(O)—.
(e) R³ and R⁴ are independently hydrogen or methyl.
(f) R³ and R⁴ are both hydrogen.
(g) Y¹ is O.
(h) Y¹ is S.
(i) R¹ and R² are both phenyl, each of which is substituted with one or more substituents (within the definition of substituents for R¹ and R² in Formula II, set forth in the SUMMARY).
(j) R¹ and R² are both phenyl, each of which is substituted with one of more with at least one substituent chosen from halogen, hydroxyl, cyano, amino, nitro, —COOH, —NHC(O)CF₃, C₁-C₂alkyl, C₁-C₂alkoxy, C₁-C₄alkylester, trifluoromethyl, and trifluoromethoxy, and optionally substituted with one or more additional substituents independently selected from hydroxyl, nitro, —CHO, C₁-C₈alkyl, C₂-C₈alkenyl, C₂-C₈alkynyl, and —(C₀-C₄alkylene)cycloalkyl, where each alkyl, alkenyl, alkynyl, or alkylene is unsubstituted or substituted with one or more substituents independently chosen from halogen, hydroxyl, amino, nitro, cyano, —CHO, or —COOH, and one or more methylene units in any alkyl, alkenyl, alkynyl, or alkylene is optionally replaced by O, NR, —C(O)—, —C(O)O—, —S(O)n—, —C(O)NR⁵—, or —NR⁵C(O)— where n is 0, 1, or 2, and R⁵ is independently chosen at each occurrence from hydrogen, C₁-C₆alkyl, and (C₀-C₂alkyl)cycloalkyl.

(k) R¹ and R² are both phenyl and are each substituted with one or two substituents independently chosen from fluoro, amino, nitro, —C(O)OCH₃, —NHC(O)CF₃, —COOH, methyl, methoxy, ethoxy, —CH₂CH₂OH, trifluoromethyl, and trifluoromethoxy.

(l) R¹ is substituted phenyl and R² is substituted or unsubstituted pyridyl.

(m) R¹ is phenyl substituted with one or two substituents independently chosen from fluoro, amino, nitro, —C(O)OCH₃, —NHC(O)CF₃, —COOH, methyl, methoxy, ethoxy, —CH₂CH₂OH, trifluoromethyl, and trifluoromethoxy.

(n) R¹ and R² are both unsubstituted cycloalkyl.
(o) R¹ and R² are the same.
(p) R¹ and R² are different.
(q) The disclosure provides compounds and pharmaceutically acceptable salts thereof of Formula II in which R¹ and R² are different;

R¹ is phenyl substituted with at least one fluoro and optionally additionally substituted with one or more groups independently selected from halogen, hydroxyl, amino, nitro, cyano, —CHO, —COOH, C₁-C₈alkyl, C₂-C₈alkenyl, C₂-C₈alkynyl, and —(C₀-C₄alkylene)cycloalkyl;

R² is chosen from C₂-C₈alkyl, mono- or bicyclic aryl, mono- or bicyclic heteroaryl, cycloalkyl, and heterocycloalkyl, each of which is unsubstituted or substituted with one or more groups independently selected from halogen, hydroxyl, amino, nitro, cyano, —CHO, —COOH, C₁-C₈alkyl, C₂-C₈alkenyl, C₂-C₈alkynyl, and —(C₀-C₄alkylene)cycloalkyl, or Where in R¹ and R² each alkyl, alkenyl, alkynyl, or alkylene is unsubstituted or substituted with one or more substituents independently chosen from halogen, hydroxyl, amino, nitro, cyano, —CHO, or —COOH, and one or more methylene units in any alkyl, alkenyl, alkynyl, or alkylene is optionally replaced by O, NR, —C(O)—, —C(O)O—, —S(O)n—, —C(O)NR⁵—, or —NR⁵C(O)— where n is 0, 1, or 2, and R⁵ is hydrogen, C₁-C₆alkyl, or (C₀-C₂alkyl)cycloalkyl;

Where R² is not 2-iodo-phenyl, 2-bromo-phenyl, 4-methyl-phenyl, 4-fluoro-phenyl, 4-bromo-phenyl, 4-chloro-phenyl, 3,4-dimethyl-phenyl, 3-chloro, 4-methylphenyl, 2,5-dimethylphenyl, 2-methoxyphenyl, 4-(CH₃CH₂OC(O)—)phenyl, or 2,5-dimethoxy-phenyl when R¹ is phenyl substituted with one fluoro substituents and no additional substituents;

X¹ and X² are the same or different and are absent (a covalent bond), —CH₂—, —C(O)—, —S(O)—, or S(O)₂—;

R³ and R⁴ is hydrogen or C₁-C₄alkyl; and
Y is S or O.

The disclosure further includes compounds Formula II-A

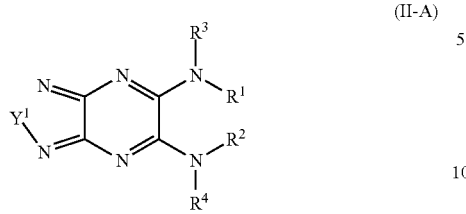
(II-A)

and the pharmaceutically acceptable salts thereof, wherein:
Y is S or O;
$R^1$ and $R^2$ are not the same;
$R^1$ is 2-fluorophenyl which is optionally substituted one or more additional substituents independently selected from halogen amino, nitro, —C(O)OCH$_3$, —NHC(O)CF$_3$, —COOH, C$_1$-C$_2$alkyl, C$_1$-C$_2$alkoxy, —CH$_2$CH$_2$OH, trifluoromethyl, and trifluoromethoxy;
$R^2$ is phenyl which is substituted with one or more substituents independently selected from halogen, amino, nitro, —C(O)OCH$_3$, —NHC(O)CF$_3$, —COOH, C$_1$-C$_2$alkyl, C$_1$-C$_2$alkoxy, —CH$_2$CH$_2$OH, trifluoromethyl, and trifluoromethoxy;
$R^3$ and $R^4$ are independently hydrogen or methyl.

In addition to compounds and salts of Formula III set forth in the SUMMARY section, the disclosure provides compounds and pharmaceutically acceptable salts of Formula I in which the variables, $R^1$, $R^2$, $R^3$, $R^4$, $R^6$, $R^9$, $X^1$, and $X^2$ carry any of the following definitions. Any of the following definitions of variables may be combined so long as a stable compound results. Thus the disclosure includes compounds and salts of Formula III

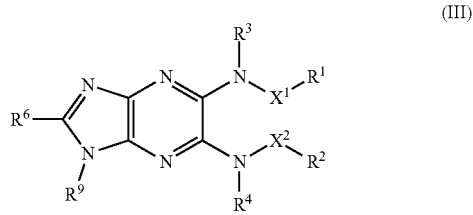
(III)

In which one or more of the following conditions are met:
(a) $X^1$ and $X^2$ are both absent.
(b) $R^6$ is hydrogen, methyl, or —C(O)OCH$_3$; and $R^9$ is trifluoromethyl.
(c) $R^1$ and $R^2$ are the same or different and are phenyl substituted with one or more groups independently selected from halogen, hydroxyl, amino, nitro, cyano, —CHO, —COOH, C$_1$-C$_8$alkyl, C$_2$-C$_8$alkenyl, C$_2$-C$_8$alkynyl, and —(C$_0$-C$_4$alkylene)cycloalkyl;
in $R^1$ and $R^2$ each alkyl, alkenyl, alkynyl, or alkylene is unsubstituted or substituted with one or more substituents independently chosen from halogen, hydroxyl, amino, nitro, cyano, —CHO, and —COOH, and one or more methylene units in any alkyl, alkenyl, alkynyl, or alkylene is optionally replaced by O, NR, —C(O)—, —C(O)O—, —S(O)n—, —C(O)NR$^5$—, or —NR$^5$C(O)— where n is 0, 1, or 2, and $R^5$ is independently chosen at each occurrence from hydrogen, C$_1$-C$_6$alkyl, and (C$_0$-C$_2$alkyl)cycloalkyl.

(d) $R^1$ and $R^2$ are the same or different and are phenyl substituted with one or more groups independently chosen from halogen, hydroxyl, cyano, amino, nitro, —COOH, —NHC(O)CF$_3$, C$_1$-C$_2$alkyl, C$_1$-C$_2$alkoxy, C$_1$-C$_4$alkylester, trifluoromethyl, and trifluoromethoxy.
(e) $R^1$ and $R^2$ are the same.
(f) $R^1$ and $R^2$ are different.

As an example, the disclosure includes the following compound of Formula III:

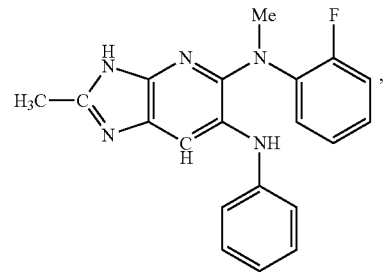 [SMILES: Cc1nc2cc(Nc3ccccc3)c(N(C)c3ccccc3F)nc2[nH]1]

The disclosure makes reference to BAM15, a compound that has the following structure:

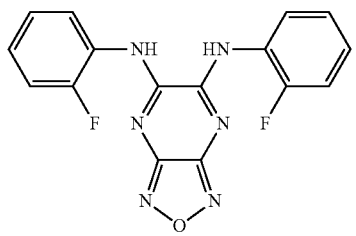 [SMILES: Fc1ccccc1Nc1nc2nonc2nc1Nc1ccccc1F]

BAM15, or N5,N6-bis(2-fluorophenyl)-[1,2,5]oxadiazolo[3,4-b]pyrazine-5,6-diamine, or (2-fluorophenyl){6-[(2-fluorophenyl)amino](1,2,5-oxadiazolo[3,4-e]pyrazine-5-yl)}amine, is further described at the national library of medicine website in the "pubchem" section, where it is referred to as compound ID 565708. Properties of BAM15 include: Molecular Weight: 340.287006 [g/mol] and Molecular Formula: C$_{16}$H$_{10}$F$_2$N$_6$O. Its chemical names are (2-fluorophenyl){6-[(2-fluorophenyl)amino](1,2,5-oxadiazolo[3,4-e]pyrazin-5-yl)}amine and N5,N6-bis(2-fluorophenyl)-[1,2,5]oxadiazolo[3,4-b]pyrazine-5,6-diamine (its IUPAC name).

Other useful compounds useful as reference standards and controls include FCCP and DNP. FCCP, or carbonyl cyanide p-trifluormethoxyphenylhydrazone, has the structure

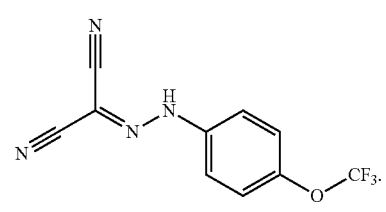
(FCCP)

DNP, or 2,4-dinitrophenol, has the following structure

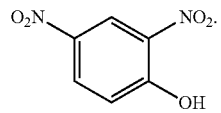 [SMILES: O=[N+]([O-])c1ccc(O)c([N+](=O)[O-])c1]

The structures of the other BAM compounds can be found in U.S. Pat. No. 9,492,448, which is hereby incorporated by reference for its teachings concerning BAM15 and BAM15 analogs (issued Nov. 15, 2016).

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines. It should also be understood that other carboxylic acid derivatives would be useful in the practice of this disclosure, for example, carboxylic acid amides, including carboxamides, lower alkyl carboxamides, dialkyl carboxamides, and the like.

Acceptable salts may be obtained using standard procedures well known in the art, for example Examples of pharmaceutically acceptable salts include, but are not limited to, mineral or organic acid salts of basic residues such as amines or nitrogen-containing heteroaryl rings (e.g. pyridine, quinoline, isoquinoline); alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HO_2C$—$(CH_2)_n$—$CO_2H$ where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Acceptable Salts: Properties, Selection and Use*, P. Heinrich Stahl and Camille G. Wermuth Editors, Wiley-VCH, 2002.

Methods of Treatment

In one embodiment, a compound of the invention is useful for treating disease, disorders, and conditions which are associated with defects in mitochondrial function or which can be treated with drugs or agents that act as uncoupling agents. The methods can comprise administering to a subject in need thereof a pharmaceutical composition comprising an effective amount of compound of Formula I, II, or III, a pharmaceutically acceptable carrier, and optionally at least one additional therapeutic agent.

In one embodiment, the present disclosure provides compositions and methods for increasing oxygen consumption, decreasing cellular reactive oxygen species, depolarizing a mitochondrial inner membrane, and increasing oxygen consumption rate without donating electrons to the electron transport chain using a mitochondrial uncoupler, said method comprising contacting a cell or mitochondria with a composition comprising at least one compound of the disclosure and optionally an additional therapeutic agent.

For example, it is disclosed herein that the mitochondrial uncoupling agents of this disclosure both prevent and reverse body fat mass increases in mice fed a high fat and high sugar Western diet. Apart from body fat, the mitochondrial uncoupling agents decrease insulin levels, which is important because it corrects hyperinsulinemia, improves glucose tolerance, and protect against diet-induced glucose tolerance. It is also disclosed herein that administration of the mitochondrial uncoupling agents reverses insulin resistance, including diet-induced insulin resistance, and restores insulin sensitivity index. Therefore, the compounds of the disclosure are useful for preventing and treating diabetes. It is also disclosed that compounds of the disclosure decrease liver fat, thus providing a treatment for fatty liver disease. It is disclosed herein that a compound of the disclosure can prevent weight gain without altering food intake and can prevent di-t-induced fat accumulation. Compounds of the disclosure are also useful for reversing diet-induced weight or fat gain and can reverse diet-induced fat gain and fatty liver.

A compound of the disclosure may exhibit at least one of the following properties or activities: energy expenditure agonist, mitochondrial uncoupler, antioxidant, increases oxygen consumption, depolarizes the mitochondrial inner membrane, stimulates respiration in isolated mitochondria, increases or stimulates oxygen consumption without donating electrons to the electron transport chain, lacks protonophore activity at the plasma membrane, decreases reperfusion-induced mitochondrial oxidative stress, decreases cellular reactive oxygen species, improves glucose tolerance, provides protection from high fat induce glucose tolerance, activates AMPK without depletion of ATP, prevents, reverses or treats insulin resistance, prevents, reverses or treats hyperinsulinemia, prevents, reverses or treats hyperlipidemia, improves blood lipid profiles, improves leanness, improves insulin sensitivity, protects from ischemic-reperfusion injury, and is less toxic than other mitochondrial inhibitors. In one embodiment, a compound of the disclosure has two or more of these properties. In one embodiment, a compound of the disclosure has three or more of these properties. In one embodiment, a compound of the disclosure has four, five, six, seven, eight, nine, ten, eleven, twelve, or more of these properties. In one embodiment, a compound of the disclosure has one, two, three, four, five, six, seven, eight, nine, or ten of these properties.

One of ordinary skill in the art will appreciate that not all configurations need to be effective or as effective as other compounds of the genus based on the teachings disclosed herein.

In one aspect, the disease, disorder or condition is selected from the group consisting of obesity, ischemia reperfusion injury, hyperinsulinemia, hyperlipidemia, glycemia, glucose tolerance, insulin sensitivity, adiposity, insulin resistance, obesity, diabetes, cancer, neurodegeneration, heart disease, renal disease, heart failure, Parkinson's disease, traumatic brain injury, stroke, aging, and disorders standing to benefit from increased energy expenditure. In one aspect, the compound is a mitochondrial uncoupler.

Compounds of the disclosure can be administered to a subject at various times, dosages, and more than once, depending on, for example, the age, sex, health, and weight of the subject, as well as on the particular disease, disorder, or condition to be treated or prevented. In one aspect, a compound is administered at a dosage ranging from about 0.1 mg/kg to about 500 mg/kg body weight. In another aspect, the compound is administered at a dosage ranging from about 0.5 mg/kg to about 100 mg/kg body weight. In yet another aspect, the compound is administered at a dosage ranging from about 1.0 mg/kg to about 50 mg/kg body weight. In one aspect, about 3.0 mg/kg is administered. In another aspect, about 5.0 mg/kg is administered. In one aspect, the dose is selected from 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 300, 400, and 500 mg/kg body weight, as well as all fractions, decimals, and integers in the range of numbers listed. In another aspect, the compound is administered as a unit dose ranging from about 10 mg to about 500 mg/unit dose.

In one aspect, a compound is administered to a subject more than once. In one aspect, the compound is a mitochondrial protonophore uncoupler lacking protonophore activity at the plasma membrane.

BAM15 and analogs and derivatives were shown to have, inter alia, uncoupling activity (see, for example, U.S. Pat. No. 9,492,448 to Hoehn et al.). The present application discloses novel and non-obvious compounds that also have uncoupling activity, and have improved pharmaceutical properties over BAM15. BAM15 and its previously disclosed analogs where symmetrical compounds—both its amine groups are substituted with the same substituent. This disclosure provides surprisingly improved asymmetrical mitochondrial uncoupler compounds. These compounds have two amine groups substituted with different substituents.

Pharmaceutical Compositions

Mitochondria regulate cellular metabolism and play an important role in the pathogenesis of some of the most prevalent human diseases including obesity, cancer, diabetes, neurodegeneration, and heart disease. The compounds of the disclosure are useful for treating and preventing these diseases and disorders and other described herein, as well as others where a mitochondrial uncoupler is useful.

BAM15 is in the public domain. It is arbitrarily named BAM15 herein. Its IUPAC name is 5-N,6-N-bis(2-fluorophenyl)-[1,2,5]oxadiazolo[3,4-b]pyrazine-5,6-diamine, it is compound number ST056388 from Timtec. The library it came from is the Timtec ApexScreen 5040.

Many anti-diabetes drugs such as insulin-sensitizers promote glucose clearance from the blood by effectively 'pushing' glucose into nutrient overloaded tissues; however, in contrast to this approach our strategy is aimed at reducing cellular nutrient stores so that tissues will 'pull' glucose from the circulation. The present method is modeled after exercise and calorie restriction interventions which also reduce cellular nutrient stores to improve glycemia and insulin sensitivity. The proof of principle is validated in humans treated with the mitochondrial uncoupler 2,4-dinitrophenol (DNP). DNP decreases adiposity and improves metabolism in humans; however, it also has a very narrow therapeutic window and was removed from FDA approval in 1938. Other anti-diabetes drugs including agonists of thyroid hormone and inhibitors of 11-0 hydroxysteroid dehydrogenase type 1 have off-target effects of increased energy expenditure that may mediate some of the protective effects of these compounds. Nevertheless, there are no drugs have been specifically targeted for increased energy expenditure.

In one embodiment, the present disclosure provides compositions and methods for preventing or treating a disease, disorder, or condition, comprising administering to a subject in need thereof a pharmaceutical composition comprising a pharmaceutically acceptable carrier, optionally at least one additional therapeutic agent, and an effective amount of at least one compound having a structure of a Formula I, II, or III.

Compounds of the disclosure can be administered to a subject at various times, dosages, and more than once, depending on, for example, the age, sex, health, and weight of the subject, as well as on the particular disease, disorder, or condition to be treated or prevented. In one aspect, a compound is administered at a dosage ranging from about 0.1 mg/kg to about 50 mg/kg body weight. In another aspect, the compound is administered at a dosage ranging from about 0.5 mg/kg to about 25 mg/kg body weight. In yet another aspect, the compound is administered at a dosage ranging from about 1.0 mg/kg to about 5.0 mg/kg body weight. In one aspect, about 3.0 mg/kg is administered. In another aspect, about 5.0 mg/kg is administered. In another aspect, the compound is administered as a unit dose ranging from about 10 mg to about 500 mg/unit dose. In one aspect, the compound is administered more than once. In one aspect, the compound is a mitochondrial protonophore uncoupler lacking protonophore activity at the plasma membrane.

A compound of the disclosure, has certain properties that can be tested for and identified in other compounds using the methods of the disclosure. For example, a compound of the disclosure has the measurable properties required of a mitochondrial protonophore uncoupler when subjected to a series of biochemical assays such as the ability to: 1) stimulate OCR when ATP synthase is inhibited; 2) depolarize the mitochondrial inner membrane; 3) stimulate respiration in isolated mitochondria; and 4) increase OCR without donating electrons to the electron transport chain.

In one aspect, a compound of the disclosure comprises a molecular weight between 205-370, HBA<5, HBD<3, 1-3 rings, and a calculated Log S of >10-3.

The present disclosure further provides compositions and methods for identifying compounds comprising the activity described herein. The novel screening assay is modeled upon the mechanisms of action of diet and exercise, including cellular nutrient composition, amplified antioxidant defense, and insulin sensitivity.

As described herein, the compositions of the present disclosure comprise, as an active agent, compounds having the structure of any of the formulas disclosed herein in a pharmaceutically acceptable form. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

The values provided herein for radicals, substituents, and ranges, are for illustration only; they do not exclude other defined values or other values within defined ranges for the radicals and substituents. The disclosed compounds include compounds of the specific Formulas recited herein having any combination of the exemplary values, preferred values, and more preferred values described herein.

It will be appreciated by those skilled in the art that compounds of the disclosure having a chiral center may exist in and be isolated in optically active and racemic forms. Some compounds may exhibit polymorphism. It is to be understood that the present disclosure encompasses any racemic, optically-active, polymorphic, or stereoisomeric form, or mixtures thereof, of a compound of the disclosure, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine compound activity using the standard tests described herein, or using other similar tests which are well known in the art.

In one embodiment, at least one of the compounds being administered is administered at least once a day. In one aspect, a compound is administered more than once. In one aspect, it is administered at least twice a day. In another embodiment, it is administered at least once a week. In yet another embodiment, it is administered at least once a month.

The disclosure further provides pharmaceutical compositions comprising compounds of the disclosure. The pharmaceutical composition may comprise one or more compounds of the disclosure, and biologically active analogs, homologs, derivatives, modifications, and pharmaceutically acceptable salts thereof, and a pharmaceutically acceptable carrier. In one embodiment, the compounds are administered as a pharmaceutical composition.

The route of administration can vary depending on the type of compound being administered. In one aspect, the compounds are administered via routes such as oral, topical, rectal, intramuscular, intramucosal, intranasal, inhalation, ophthalmic, and intravenous.

The present disclosure further provides for administration of a compound of the disclosure as a controlled-release formulation.

In one embodiment, the present disclosure provides administering at least three compounds, wherein at least three of the compounds are topiramate, ondansetron, and naltrexone.

In one embodiment, the present disclosure provides compositions and methods for treating alcohol-related diseases and disorders using pharmaceutical compositions comprising effective amounts of topiramate, ondansetron, and naltrexone.

The dosage of the active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present disclosure has application for both human and veterinary use.

Processes for preparing compounds of any of the formulas of the disclosure or for preparing intermediates useful for preparing compounds of any of the formulas of the disclosure are provided as further embodiments of the disclosure. Intermediates useful for preparing compounds of Formula I, II, and III are also provided as further embodiments of the disclosure.

Processes for preparing compounds of any of the formulas of the disclosure are provided as further embodiments of the disclosure and are illustrated by the following procedures in which the meanings of the generic radicals are as given above unless otherwise qualified.

The compounds of any of the formulas of the disclosure can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the disclosure can be administered using various kinds of delivery systems and media. Furthermore, compounds of the disclosure can be administered in combination with other therapeutic agents and compounds and can be used with other kinds of treatments.

In one embodiment, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula I, II, and III to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), which are hereby incorporated by reference for their teachings regarding topical formulations.

Useful dosages of the compounds of the formulas of the disclosure can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of Formula I, II, or III in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

For example, in one embodiment relating to oral administration to humans, a dosage of between approximately 0.1 and 300 mg/kg/day, or between approximately 0.5 and 50 mg/kg/day, or between approximately 1 and 10 mg/kg/day, is generally sufficient, but will vary depending on such things as the disorder being treated, the length of treatment, the age, sex, weight, and/or health of the subject, etc. In one aspect, a unit dose is used. In one aspect, the unit dose is supplied in a syringe. The combinations of drugs can be administered in formulations that contain all drugs being used, or the drugs can be administered separately. In some cases, it is anticipated that multiple doses/times of administration will be required or useful. Additionally, for some treatment regimens, at least two compounds will be used. In one aspect, at least three compounds will be administered. The present disclosure further provides for varying the length of time of treatment.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, when the active ingredient needs to enter circulation and be delivered via blood, the active ingredient, in one embodiment, should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In another embodiment, a formulation of the disclosure can be impregnated into a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

The composition of the disclosure can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Non-synthetic matrix proteins like collagen, glycosaminoglycans, and hyaluronic acid, which are enzymatically digested in the body, are useful for delivery (see U.S. Pat. Nos. 4,394,320; 4,472,840; 5,366,509; 5,606,019; 5,645,591; and 5,683,459) and are suitable for use with the present disclosure. Other implantable media and devices can be used for delivery of the compounds of the disclosure in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The compounds of the present disclosure can be further combined with growth factors, nutrient factors, pharmaceuticals, calcium-containing compounds, anti-inflammatory agents, antimicrobial agents, or any other substance capable of expediting or facilitating bone or tissue growth, stability, and remodeling.

The compositions of the present disclosure can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

Examples of antimicrobial agents that can be used in the present disclosure include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

In one embodiment, the compounds of the disclosure can first be encapsulated into microcapsules, microspheres, microparticles, microfibers, reinforcing fibers and the like to facilitate mixing and achieving controlled, extended, delayed and/or sustained release and combined other agents or drugs. Encapsulating the biologically active agent can also protect the agent against degradation during formation of the composite of the disclosure.

In another embodiment of the disclosure, the compound is controllably released into a subject when the composition of the disclosure is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

The method of the disclosure includes a kit comprising a compound identified in the disclosure and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the disclosure prior to administering the compound to a cell or a subject. Preferably the subject is a human.

In accordance with the present disclosure, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present disclosure.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present disclosure, and are not to be construed as limiting in any way the remainder of the disclosure. Therefore, the examples should be construed to encompass any and all variations which become evident as a result of the teaching provided herein.

EXAMPLES

The following synthetic schemes and general procedures provide general methods for the synthesis of the different classes of compounds of this disclosure. Those of ordinary skill in the art of synthetic organic synthesis will readily recognize the changes to starting materials and reaction conditions needed to effect synthesis of the particular compounds of the disclosure listed in Example 1, which follows.

added dropwise, and the reaction was then allowed to warm to room temperature and allowed to stir for 19 h. After which, the solution was concentrated via vacuum, and the residue was purified by silica gel column chromatography to yield an asymmetrical arylamine, 4.

Scheme 1. Synthesis of Symmetrical Oxadiazolo-Pyrazine Diarylamine Compounds

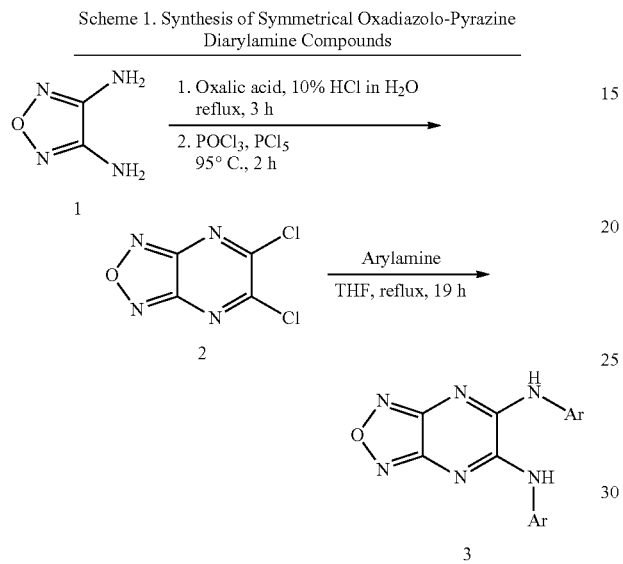

General Procedure A: Symmetric 5,6-Dichloro-[1,2,5]oxadiazolo[3,4-b]pyrazine (2, 1 equiv.) was dissolved in THF (0.6 M solution). The desired substituted arylamine (3 equiv.) was then added. The reaction mixture was allowed reflux for 13 h. After which, the solution was concentrated via vacuum, and the residue was purified by silica gel column chromatography to yield the title compound.

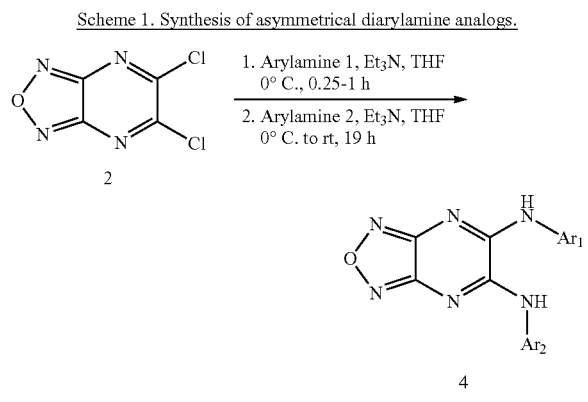

General Procedure B: 5,6-Dichloro-[1,2,5]oxadiazolo[3,4-b]pyrazine (2, 1 equiv.) was dissolved in THF (0.52 M solution) and cooled to 0° C. The desired substituted arylamines (0.9 equiv.) was then added dropwise and allowed to stir for 10 min. Triethylamine (1 equiv.) was then added dropwise and allowed to stir at 0° C. for 1 h. The second desired substituted arylamine was then added dropwise and allowed to stir for 10 min. Triethylamine (1 equiv.) was then Scheme 2. Methylation of BAM15.

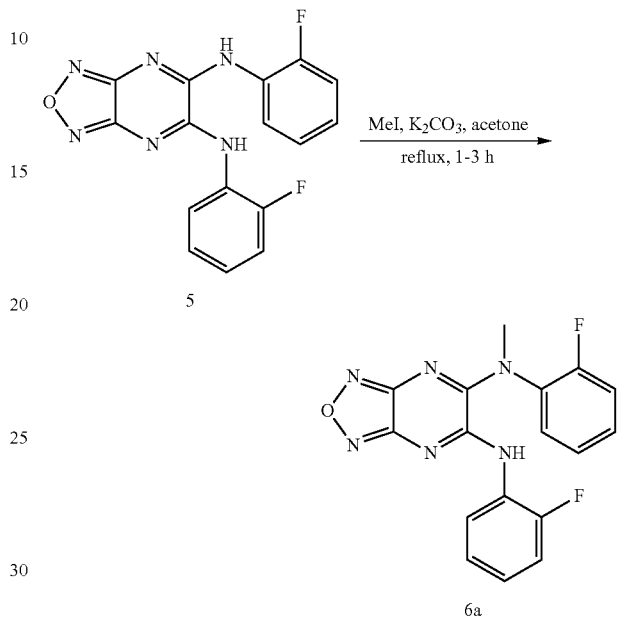

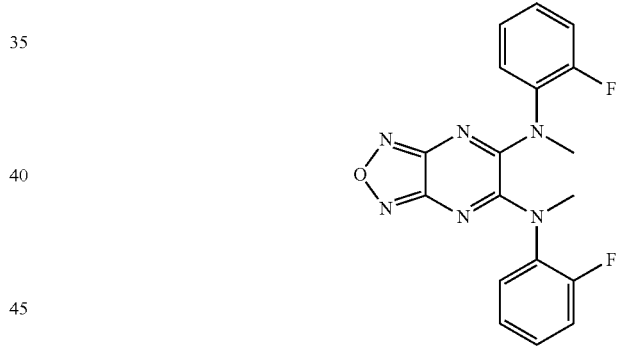

Scheme 3. Synthesis of asymmetrical arylamine/alkylamine analogs.

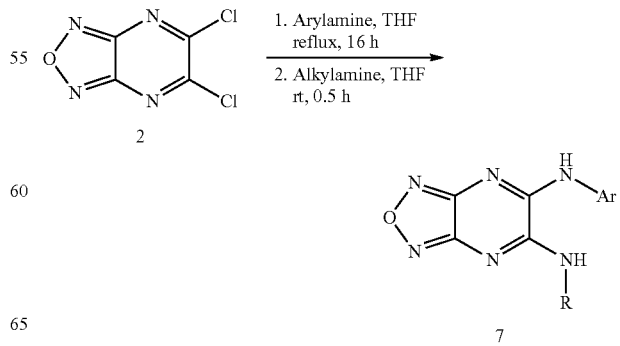

General Procedure C. Unsymmetric Alkylamine and Arylamine Derivative Synthesis 5,6-Dichloro-[1,2,5]oxadiazolo[3,4-b]pyrazine (2, 1 equiv.) was dissolved in THF (0.6 M solution). The desired arylamine (2 equiv.) was then added. The reaction mixture was allowed to reflux for 16 h. After which, the solution was concentrated via vacuum, and the residue was purified via flash chromatography using dichloromethane/methanol solvent system to obtain the monoaminated intermediate. The intermediate was in turn dissolved in THF (0.6 M). The desired alkylamine was added dropwise at room temperature and allowed to stir for 1 h. The resulting reaction mixture was then concentrated via vacuum, and the resulting residue was purified via flash chromatography using dichloromethane/methanol solvent system to obtain the asymmetrical arylamine/alkylamine compound, 7.

General Procedure E. Oxadiazole ring reduction and 1H-imidazo ring formation. In a sealed container, the desired derivative 3 or 4 (1 equiv.), Fe (10 equiv.), Yb(OTf)$_3$ (0.1 equiv.) and triethyl-orthoformate/acetate/benzoate (5 equiv.) were mixed in acetic acid. The mixture was heated at 90° C. and stirred for 3 h. The resulting mixture was filtered through celite and then dissolved in 1:1 water/ethyl acetate. The first aqueous layer was discarded. The organic phase was washed twice with a saturated aqueous solution of sodium bicarbonate. The organic phase was concentrated via vacuum, and the resulting residue was purified via flash chromatography using hexanes/ethyl acetate solvent system to obtain the title compound.

Scheme 4. Synthesis of [1,2,5]thiadiazolo[3,4-b]pyrazine analogs.

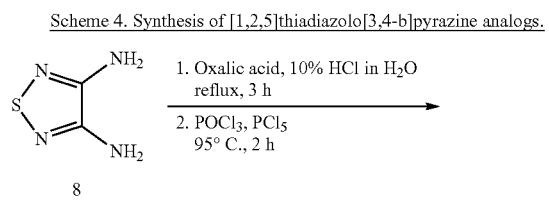

Scheme 6. Synthesis of trifluoromethyl-imidazo[4,5-b]pyrazine analogs.

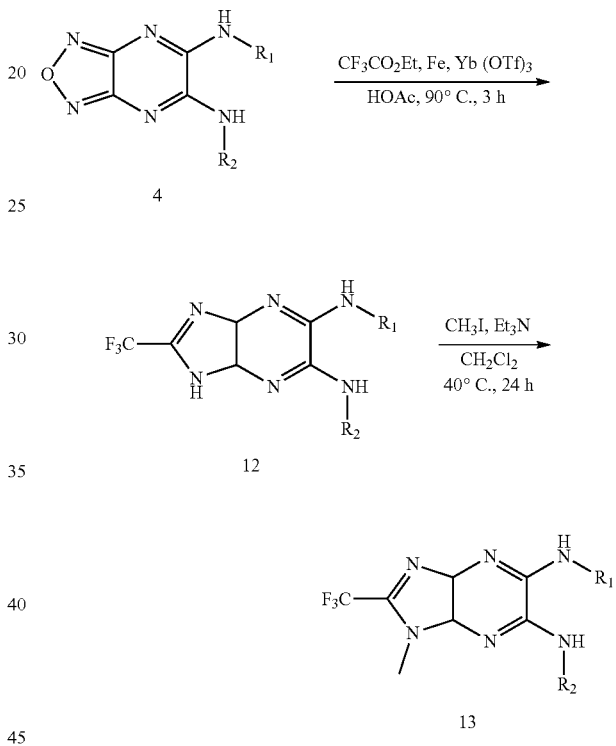

Scheme 5. Synthesis of imidazo[4,5-b]pyrazine analogs.

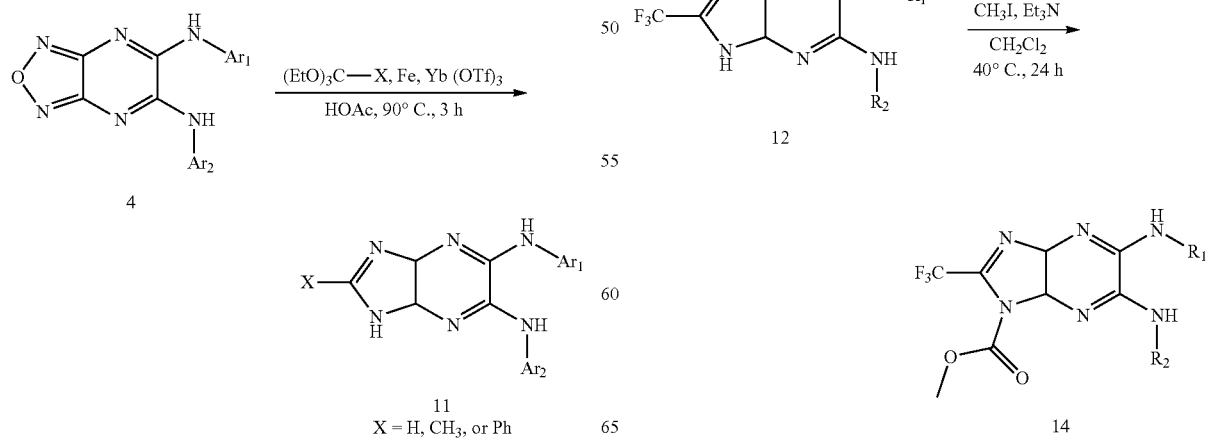

General Procedure F. Oxadiazole ring reduction and 2-(trifluoromethyl)-1H-imidazo ring formation. In a sealed container, the desired derivative 3, 4 or 7 (1 equiv.), Fe (10 equiv.), Yb(OTf)$_3$ (0.1 equiv.) and ethyl-2,2,2-trifluoroacetate (10 equiv.) were mixed in acetic acid. The mixture was heated at 90° C. and stirred for 3 h. The resulting mixture was filtered through Celite and then dissolved in 1:1 water/ethyl acetate. The first aqueous layer was discarded. The organic phase was washed twice with a saturated aqueous solution of sodium bicarbonate. The organic phase was concentrated via vacuum, and the resulting residue was purified via flash chromatography using hexanes/ethyl acetate solvent system to obtain compound 12.

General Procedure G. Methylation of the 1H-imidazole position. In a sealed container, the desired derivative 12 (1 equiv.), triethylamine (2 equiv.) and iodomethane (10 equiv.) were dissolved in dichloromethane. The solution was heated to 40° C. and stirred for 24 h. The resulting mixture was concentrated via vacuum and the residue was purified via flash chromatography using a hexanes/ethyl acetate solvent system to obtain compound 13.

General Procedure H. Addition of methyl formate to 1H-imidazole position. The desired derivative 12 (1 equiv.) and triethylamine (3 equiv.) were dissolved in dichloromethane. At 0° C., methyl chloroformate (3 equiv.) was added to the solution and stirred for 1 h. The resulting mixture was concentrated via vacuum and the residue was purified via flash chromatography using a dichloromethane/methanol solvent system to obtain compound 14.

Scheme 7. Synthesis of pyrazine analogs.

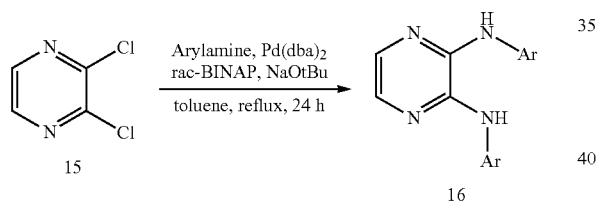

General Procedure D. Symmetric Pyrazine Derivative Synthesis. 2,3 Dichloropyrazine (15, 1 equiv.), arylamine (2.68 equiv.), sodium tert-butoxide (2 equiv.), rac-BINAP (0.2 equiv.), Pd(0)(dba)$_2$ (0.10 equiv.) were added into 4 mL of dry toluene and purged with nitrogen while stirring at room temperature for 20 min. The reaction mixture was heated to reflux for 24 h, allowed to cool to room temperature and the solvent was removed under reduced pressure. The resulting residue was extracted with CH$_2$Cl$_2$ and washed with water twice. The organic layer was dried over anhydrous sodium sulfate and the solvent removed under reduced pressure yielding an oily crude product. The product was purified via flash chromatography on SiO$_2$ with a solvent system of hexanes/ethyl acetate. The final product was dried under vacuum to yield the desired product as a yellow oil.

Example 1. Synthesis of Compounds

Compounds of the disclosure were synthesized according to Schemes 1-8 and General Procedures A-H. TABLE 1 providing the compound structures with an identifying compound number is provided below.

TABLE 1

| Compound | Structure |
|---|---|
| 3a | 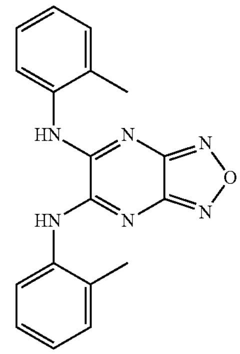 [SMILES: Cc1ccccc1Nc1nc2nonc2nc1Nc1ccccc1C] |
| 3b | 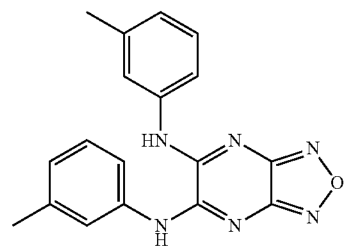 [SMILES: Cc1cccc(Nc2nc3nonc3nc2Nc2cccc(C)c2)c1] |
| 3c | 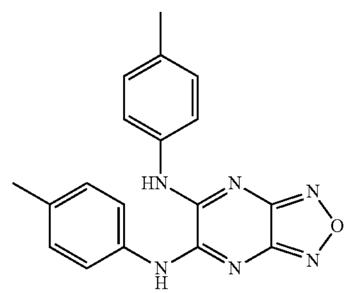 [SMILES: Cc1ccc(Nc2nc3nonc3nc2Nc2ccc(C)cc2)cc1] |
| 3d | 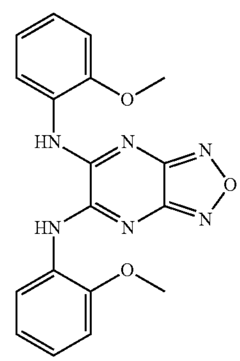 [SMILES: COc1ccccc1Nc1nc2nonc2nc1Nc1ccccc1OC] |
| 3e | 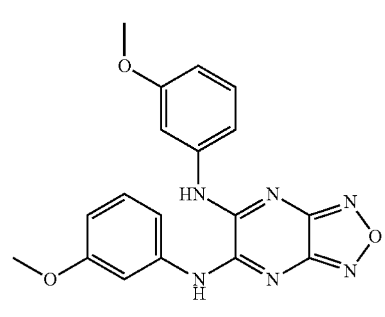 [SMILES: COc1cccc(Nc2nc3nonc3nc2Nc2cccc(OC)c2)c1] |

TABLE 1-continued

| Compound | Structure |
|---|---|
| 3f | (4-methoxyphenyl)-NH and (4-methoxyphenyl)-NH substituents on [1,2,5]oxadiazolo[3,4-b]pyrazine |
| 3g | (2-ethoxyphenyl)-NH and (2-ethoxyphenyl)-NH substituents on [1,2,5]oxadiazolo[3,4-b]pyrazine |
| 3h | (3-ethoxyphenyl)-NH and (3-ethoxyphenyl)-NH substituents on [1,2,5]oxadiazolo[3,4-b]pyrazine |
| 3i | (4-ethoxyphenyl)-NH and (4-ethoxyphenyl)-NH substituents on [1,2,5]oxadiazolo[3,4-b]pyrazine |
| 3j | (3-hydroxyphenyl)-NH and (3-hydroxyphenyl)-NH substituents on [1,2,5]oxadiazolo[3,4-b]pyrazine |
| 3k | (2-trifluoromethoxyphenyl)-NH and (2-trifluoromethoxyphenyl)-NH substituents on [1,2,5]oxadiazolo[3,4-b]pyrazine |
| 3l | (3-trifluoromethoxyphenyl)-NH and (3-trifluoromethoxyphenyl)-NH substituents on [1,2,5]oxadiazolo[3,4-b]pyrazine |
| 3m | (4-trifluoromethoxyphenyl)-NH and (4-(2,2,2-trifluoroethyl)phenyl)-NH substituents on [1,2,5]oxadiazolo[3,4-b]pyrazine |
| 3n | (3-fluorophenyl)-NH and (3-fluorophenyl)-NH substituents on [1,2,5]oxadiazolo[3,4-b]pyrazine |

TABLE 1-continued

| Compound | Structure |
|---|---|
| 3o | (structure) |
| 3p | (structure) |
| 3q | (structure) |
| 3r | (structure) |
| 3s | (structure) |
| 3t | (structure) |
| 3u | (structure) |
| 3v | (structure) |

TABLE 1-continued
| Compound | Structure |
|---|---|
| 3w | 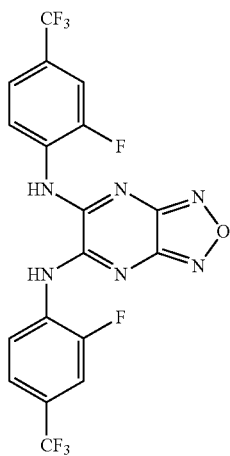 [SMILES: Fc1cc(C(F)(F)F)ccc1Nc1nc2nonc2nc1Nc1ccc(C(F)(F)F)cc1F] |
| 3x | 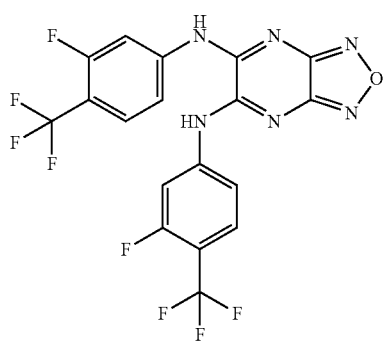 [SMILES: Fc1cc(Nc2nc3nonc3nc2Nc2ccc(C(F)(F)F)c(F)c2)ccc1C(F)(F)F] |
| 3y | 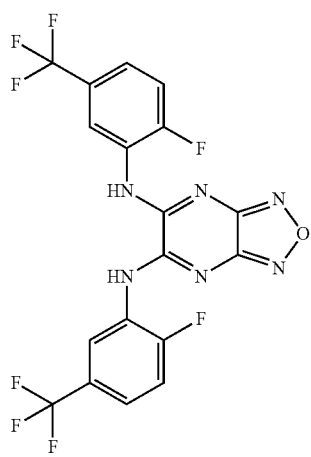 [SMILES: Fc1ccc(C(F)(F)F)cc1Nc1nc2nonc2nc1Nc1cc(C(F)(F)F)ccc1F] |
| 3z | 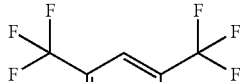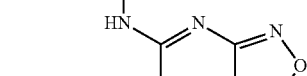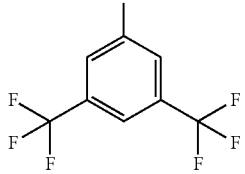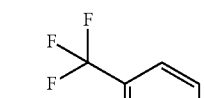 |
| 3aa | 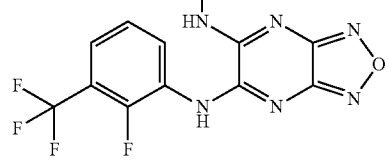 |
| 3bb | 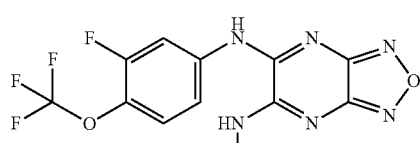 |
| 3cc | 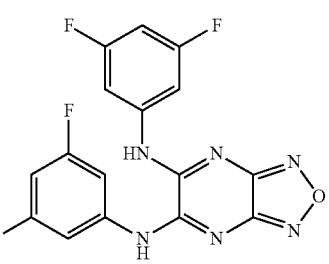 |

TABLE 1-continued

| Compound | Structure |
|---|---|
| 3dd | (structure) |
| 3ee | (structure) |
| 3y | (structure) |
| 3z | (structure) |
| 3aa | (structure) |
| 3bb | (structure) |
| 3cc | (structure) |
| 3dd | (structure) |
| 3ee | (structure) |

TABLE 1-continued

| Compound | Structure |
|---|---|
| 4a | 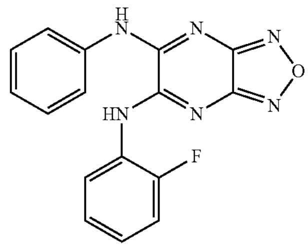 [SMILES: Fc1ccccc1Nc1nc2nonc2nc1Nc1ccccc1] |
| 4b | 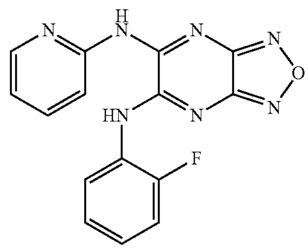 [SMILES: Fc1ccccc1Nc1nc2nonc2nc1Nc1ccccn1] |
| 4c | 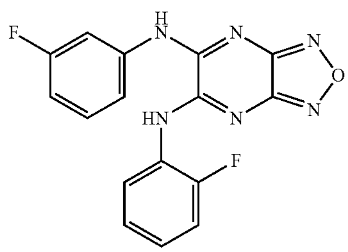 [SMILES: Fc1cccc(Nc2nc3nonc3nc2Nc2ccccc2F)c1] |
| 4d | 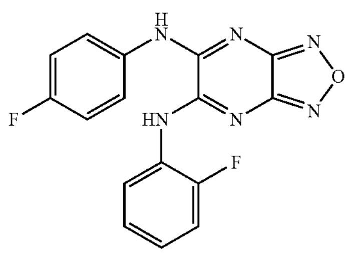 [SMILES: Fc1ccc(Nc2nc3nonc3nc2Nc2ccccc2F)cc1] |
| 4e | 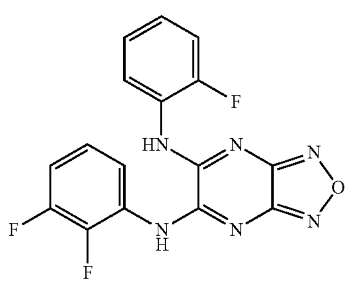 [SMILES: Fc1ccccc1Nc1nc2nonc2nc1Nc1cccc(F)c1F] |
| 4f | |
| 4g | |
| 4h | |
| 4i | |

TABLE 1-continued

| Compound | Structure |
|---|---|
| 4j | (2-methoxyphenyl)-NH / (2-fluorophenyl)-NH substituted furazano[3,4-b]pyrazine |
| 4k | (3-methoxyphenyl)-NH / (2-fluorophenyl)-NH substituted furazano[3,4-b]pyrazine |
| 4l | (4-methoxyphenyl)-NH / (2-fluorophenyl)-NH substituted furazano[3,4-b]pyrazine |
| 4m | (2-fluorophenyl)-NH / (2-ethoxyphenyl)-NH substituted furazano[3,4-b]pyrazine |
| 4n | (2-fluorophenyl)-NH / (3-ethoxyphenyl)-NH substituted furazano[3,4-b]pyrazine |

TABLE 1-continued

| Compound | Structure |
|---|---|
| 4a | phenyl-NH / (2-fluorophenyl)-NH substituted furazano[3,4-b]pyrazine |
| 4b | (pyridin-2-yl)-NH / (2-fluorophenyl)-NH substituted furazano[3,4-b]pyrazine |
| 4c | (3-fluorophenyl)-NH / (2-fluorophenyl)-NH substituted furazano[3,4-b]pyrazine |
| 4d | (4-fluorophenyl)-NH / (2-fluorophenyl)-NH substituted furazano[3,4-b]pyrazine |
| 4e | (2-fluorophenyl)-NH / (3,4-difluorophenyl)-NH substituted furazano[3,4-b]pyrazine |

TABLE 1-continued

| Compound | Structure |
|---|---|
| 4f | (2-fluorophenyl)-NH and (2,4-difluorophenyl)-NH substituents on furazano[3,4-b]pyrazine |
| 4g | (2-fluorophenyl)-NH and (2-fluorophenyl)-NH substituents on furazano[3,4-b]pyrazine |
| 4h | (3-methylphenyl)-NH and (2-fluorophenyl)-NH substituents on furazano[3,4-b]pyrazine |
| 4i | (4-methylphenyl)-NH and (2-fluorophenyl)-NH substituents on furazano[3,4-b]pyrazine |
| 4j | (2-methoxyphenyl)-NH and (2-fluorophenyl)-NH substituents on furazano[3,4-b]pyrazine |
| 4k | (3-methoxyphenyl)-NH and (2-fluorophenyl)-NH substituents on furazano[3,4-b]pyrazine |
| 4l | (4-methoxyphenyl)-NH and (2-fluorophenyl)-NH substituents on furazano[3,4-b]pyrazine |
| 4m | (2-fluorophenyl)-NH and (2-ethoxyphenyl)-NH substituents on furazano[3,4-b]pyrazine |
| 4n | (2-fluorophenyl)-NH and (3-ethoxyphenyl)-NH substituents on furazano[3,4-b]pyrazine |

TABLE 1-continued

| Compound | Structure |
|---|---|
| 4o | *(structure: 5-(2-fluorophenylamino)-6-(4-ethoxyphenylamino)-[1,2,5]oxadiazolo[3,4-b]pyrazine)* |
| 4p | *(structure: 5-(2-fluorophenylamino)-6-(3-hydroxyphenylamino)-[1,2,5]oxadiazolo[3,4-b]pyrazine)* |
| 4q | *(structure: 5-(2-trifluoromethoxyphenylamino)-6-(2-fluorophenylamino)-[1,2,5]oxadiazolo[3,4-b]pyrazine)* |
| 4r | *(structure: 5-(3-trifluoromethoxyphenylamino)-6-(2-fluorophenylamino)-[1,2,5]oxadiazolo[3,4-b]pyrazine)* |
| 4s | *(structure: 5-(4-trifluoromethoxyphenylamino)-6-(2-fluorophenylamino)-[1,2,5]oxadiazolo[3,4-b]pyrazine)* |
| 4t | *(structure: 5-(2-fluorophenylamino)-6-(4-(2,2,2-trifluoroacetamido)phenylamino)-[1,2,5]oxadiazolo[3,4-b]pyrazine)* |
| 4u | *(structure: 5-(2-trifluoromethylphenylamino)-6-(2-fluorophenylamino)-[1,2,5]oxadiazolo[3,4-b]pyrazine)* |
| 4v | *(structure: 5-(3-trifluoromethylphenylamino)-6-(2-fluorophenylamino)-[1,2,5]oxadiazolo[3,4-b]pyrazine)* |
| 4w | *(structure: 5-(4-trifluoromethylphenylamino)-6-(2-fluorophenylamino)-[1,2,5]oxadiazolo[3,4-b]pyrazine)* |

TABLE 1-continued
| Compound | Structure |
|---|---|
| 4x | |
| 4y | |
| 4z | |
| 4aa | |⏎
| 4bb | 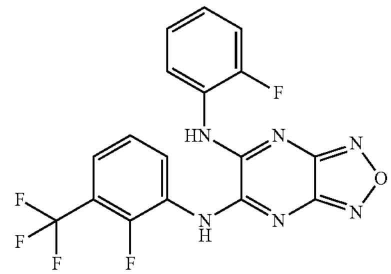 [SMILES: Fc1ccccc1Nc1nc2nonc2nc1Nc1cccc(C(F)(F)F)c1F] |
| 6a | 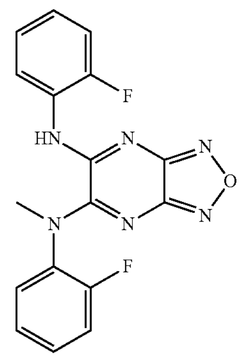 [SMILES: CN(c1ccccc1F)c1nc2nonc2nc1Nc1ccccc1F] |
| 6b | 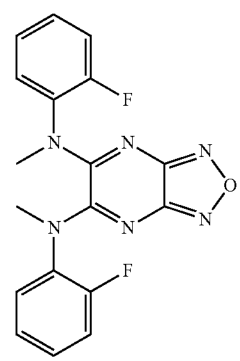 [SMILES: CN(c1ccccc1F)c1nc2nonc2nc1N(C)c1ccccc1F] |
| 7a | 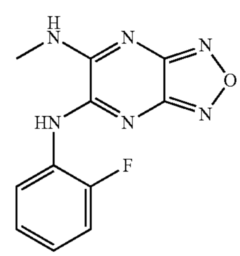 [SMILES: CNc1nc2nonc2nc1Nc1ccccc1F] |
| 7b | 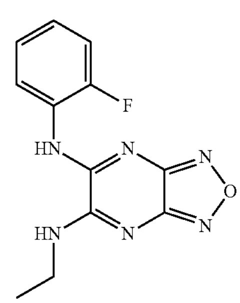 [SMILES: CCNc1nc2nonc2nc1Nc1ccccc1F] |
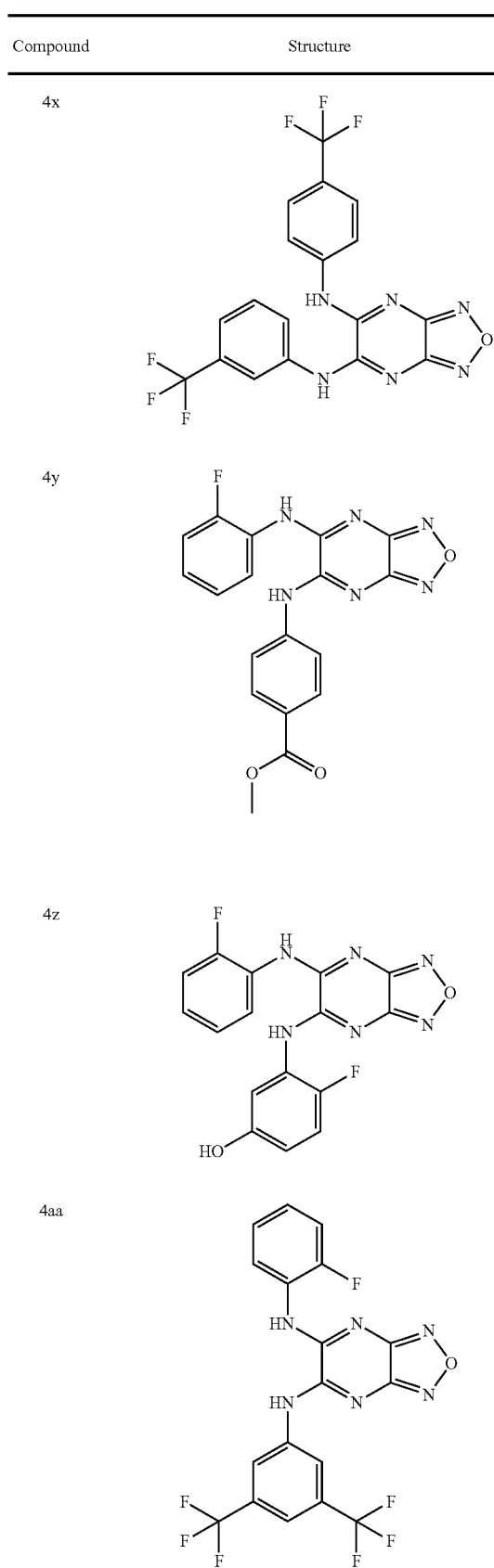
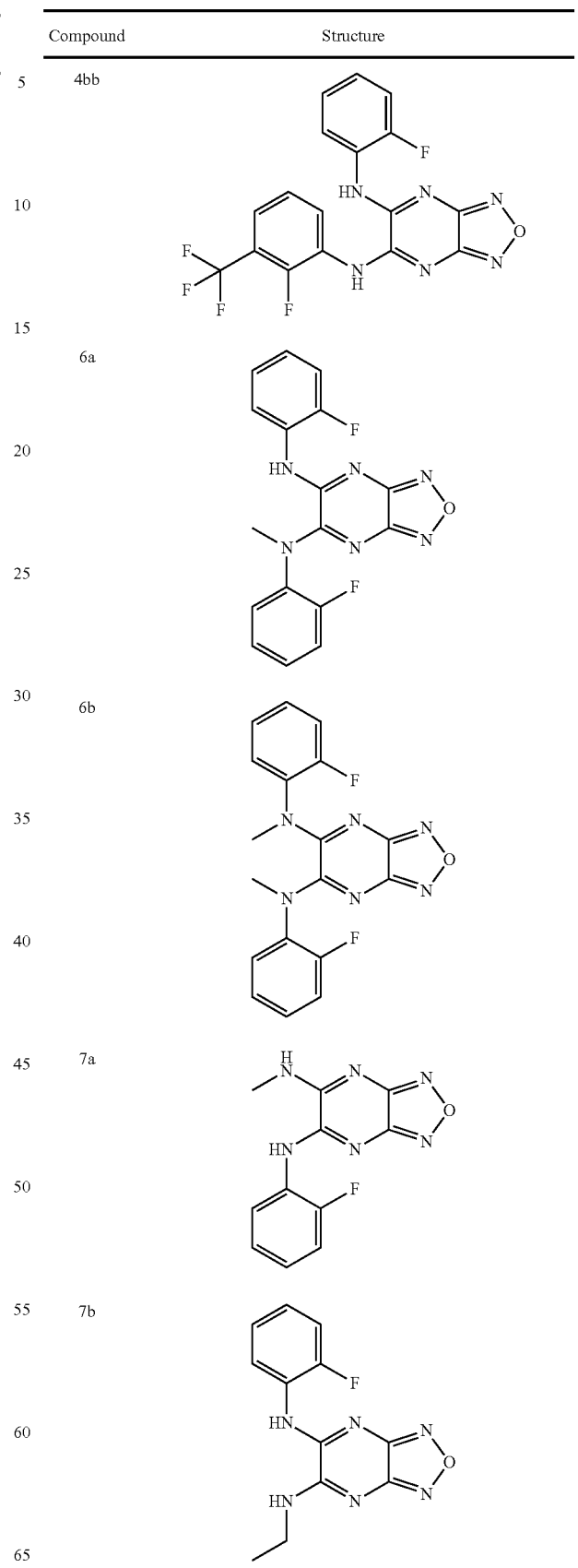

TABLE 1-continued

| Compound | Structure |
|---|---|
| 7c | (structure) |
| 7d | (structure) |
| 7e | (structure) |
| 7f | (structure) |
| 7g | (structure) |
| 7h | (structure) |
| 7i | (structure) |
| 10 | (structure) |
| 11a | (structure) |
| 11b | (structure) |

TABLE 1-continued

| Compound | Structure |
|---|---|
| 11c | (2-fluorophenyl-NH)-(2-fluorophenyl-NH)-pyrazine-imidazole-2-phenyl |
| 12a | (2-fluorophenyl-NH)-(2-fluorophenyl-NH)-pyrazine-imidazole-2-CF₃ |
| 12b | (2-fluoro-5-CF₃-phenyl-NH)-(2-fluoro-5-CF₃-phenyl-NH)-pyrazine-imidazole-2-CF₃ |
| 12c | (2-fluorophenyl-NH)-(2-fluorophenyl-NH)-pyrazine-imidazole-2-CF₃ |
| 12d | (3,5-bis(CF₃)phenyl-NH)-(3,5-bis(CF₃)phenyl-NH)-pyrazine-imidazole-2-CF₃ |
| 12e | (2-fluoro-3-CF₃-phenyl-NH)-(2-fluoro-3-CF₃-phenyl-NH)-pyrazine-imidazole-2-CF₃ |
| 12f | (3-fluoro-4-OCF₃-phenyl-NH)-(3-fluoro-4-OCF₃-phenyl-NH)-pyrazine-imidazole-2-CF₃ |
| 12g | (2-fluoro-4-CF₃-phenyl-NH)-(2-fluoro-4-CF₃-phenyl-NH)-pyrazine-imidazole-2-CF₃ |

TABLE 1-continued

| Compound | Structure |
|---|---|
| 12h | (structure) |
| 12i | (structure) |
| 12j | (structure) |
| 12k | (structure) |
| 12l | (structure) |
| 12m | (structure) |
| 12n | (structure) |
| 12o | (structure) |
| 12p | (structure) |
| 12q | (structure) |

TABLE 1-continued

| Compound | Structure |
|---|---|
| 12r | (structure) |
| 12s | (structure) |
| 12t | (structure) |
| 12u | (structure) |
| 12v | (structure) |
| 12w | (structure) |
| 12x | (structure) |
| 13a | (structure) |
| 13b | (structure) |

TABLE 1-continued
| Compound | Structure |
|---|---|
| 13c | 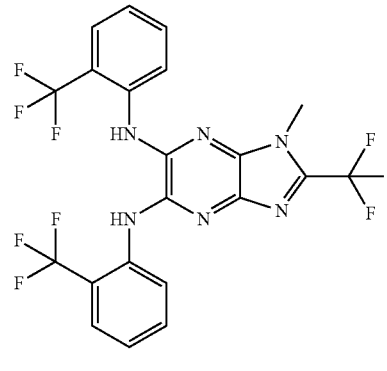 |
| 13d | 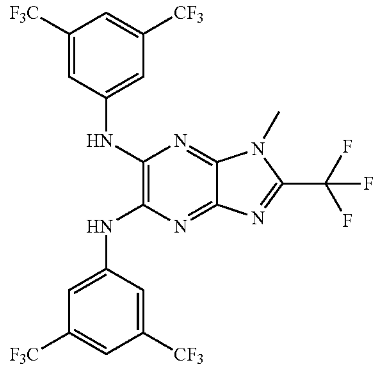 [SMILES: Cn1c(C(F)(F)F)nc2nc(Nc3cc(C(F)(F)F)cc(C(F)(F)F)c3)c(Nc3cc(C(F)(F)F)cc(C(F)(F)F)c3)nc21] |
| 13e | 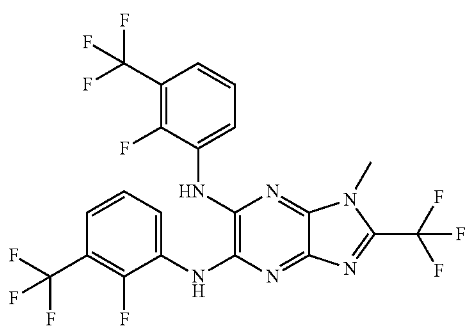 [SMILES: Cn1c(C(F)(F)F)nc2nc(Nc3cccc(C(F)(F)F)c3F)c(Nc3cccc(C(F)(F)F)c3F)nc21] |
| 13f | 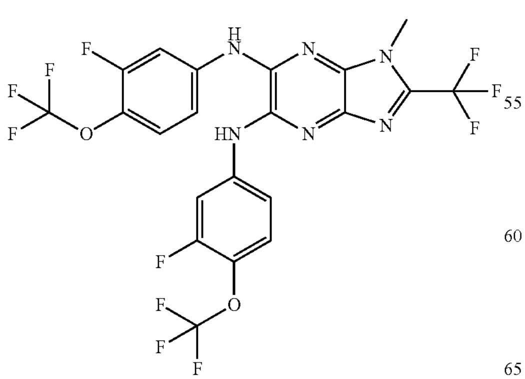 |
| 13g | 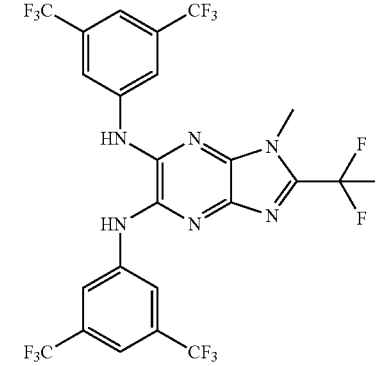 |
| 13h | |
| 13i | |
| 13j | |

TABLE 1-continued

| Compound | Structure |
|---|---|
| 13k | (structure) |
| 13l | (structure) |
| 13m | (structure) |
| 13n | (structure) |
| 13o | (structure) |
| 13p | (structure) |
| 13q | (structure) |
| 13r | (structure) |
| 13s | (structure) |
| 13t | (structure) |

TABLE 1-continued

| Compound | Structure |
|---|---|
| 13u | (structure) |
| 13v | (structure) |
| 13w | (structure) |
| 13x | (structure) |
| 14a | (structure) |
| 14b | (structure) |
| 14c | (structure) |
| 16a | (structure) |
| 16c | (structure) |

TABLE 1-continued

| Compound | Structure |
|---|---|
| 16d | |
| 16e | |
| 16f | |
| 16g | |
| 16h | 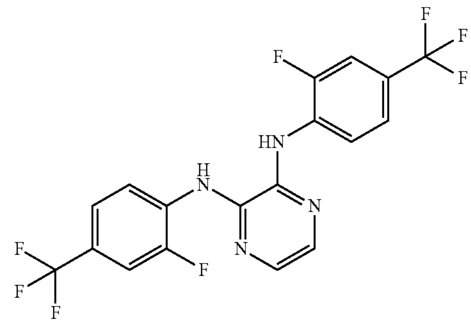 [SMILES: Fc1cc(C(F)(F)F)ccc1Nc1nccnc1Nc1ccc(C(F)(F)F)cc1F] |
| 16i | 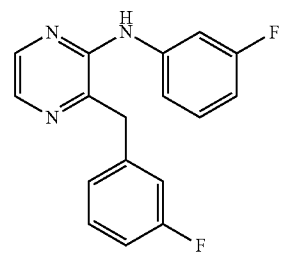 [SMILES: Fc1cccc(Cc2nccnc2Nc2cccc(F)c2)c1] |
| 16j | 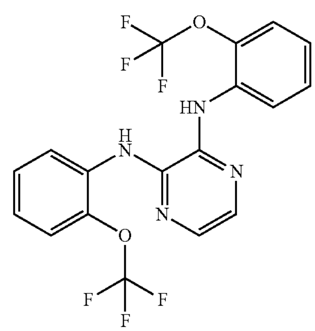 [SMILES: FC(F)(F)Oc1ccccc1Nc1nccnc1Nc1ccccc1OC(F)(F)F] |
| 16k | 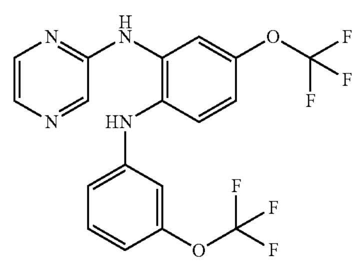 [SMILES: FC(F)(F)Oc1cccc(Nc2ccc(OC(F)(F)F)cc2Nc2cnccn2)c1] |
| 16l | 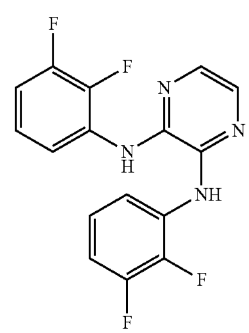 [SMILES: Fc1cccc(Nc2nccnc2Nc2cccc(F)c2F)c1F] |

TABLE 1-continued

| Compound | Structure |
|---|---|
| 16m | (structure: pyrazine with two NH-(2,4-difluorophenyl) substituents) |
| 16n | (structure: pyrazine with two NH-(4-trifluoromethoxyphenyl) substituents) |

Synthesis and characterization of the compounds listed in Table 1. A brief synthetic protocol is provided below for each compound shown in Table 1. Each compound is identified by its chemical name, followed in parenthesis by the compound number from Table 1.

Note on the NMR spectra. These compounds contain many heteroatoms and are prone to form a mixture of tautomers (Konstandaras, N. et al., *ChemistrySelect* 2017, 2, 7018-7023), many peaks in the NMR are broad, including aromatic C—H peaks, with no defined splitting pattern. These peaks are labeled as broad singlets (brs) or broad multiplets (brm). In cases where one tautomer is significantly favored, the characterization for the main tautomer is presented for simplicity.

5,6-dichloro-[1,2,5]oxadiazolo[3,4-b]pyrazine (2). 1,2,5-oxadiazole-3,4-diamine (1 equiv.) was dissolved in 10% HCl (6 M solution). Oxalic acid (1.5 equiv.) was added to the solution, and the mixture was heated to reflux for 3 h. After which, the mixture was cooled to rt, filtered, and dried. The resulting dihydroxy white solid was then carried forward crude (1 equiv.) by adding phosphorous pentachloride (6 equiv.) and phosphorous oxychloride (2 M solution). The resulting mixture was heated to 95° C. for 2 h, and excess phosphorous oxychloride was removed via vacuum distillation. The mixture was cooled to 0° C., and cold water was added (15-20 mL), causing the title compound to precipitate out of solution. The precipitate was purified via recrystallization using an acetone/water mixture, producing the title compound 2 as a white solid, 23%. Analytical data matches with the literature (Thottempudi, V.; et al., *Chem. Eur. J.* 2014, 20, 542-548).

$N^5,N^6$-di-o-tolyl-[1,2,5]oxadiazolo[3,4-b]pyrazine-5,6-diamine (3a). Synthesized by general procedure A. 35%, yellow solid. $^1$H NMR (400 MHz, Acetone-$d_6$) δ 9.36 (s, 2H), 7.58-7.52 (m, 2H), 7.40-7.25 (m, 6H), 2.34 (s, 6H); HRMS (ESI$^+$): Calcd for $C_{18}H_{17}N_6O^+$ [M+H]$^+$: 333.1464, Found: 333.1470.

$N^5,N^6$-di-m-tolyl-[1,2,5]oxadiazolo[3,4-b]pyrazine-5,6-diamine (3b). Synthesized by general procedure A. 60%, yellow solid. $^1$H NMR (400 MHz, Acetone-$d_6$) δ 9.64 (brs, 2H), 7.80-7.36 (brm, 4H), 7.32 (t, J=7.7 Hz, 2H), 7.03 (d, J=7.5 Hz, 2H), 2.37 (s, 6H); HRMS (ESI$^+$): Calcd for $C_{18}H_{17}N_6O^+$[M+H]$^+$: 333.1464, Found: 333.1464.

$N^5,N^6$-di-p-tolyl-[1,2,5]oxadiazolo[3,4-b]pyrazine-5,6-diamine (3c). Synthesized by general procedure A. 69%, off-white solid. $^1$H NMR (400 MHz, Acetone-$d_6$) δ 9.56 (brs, 2H), 7.82-7.42 (brm, 4H), 7.25 (d, J=8.1 Hz, 4H), 2.34 (s, 6H); HRMS (ESI$^+$): Calcd for $C_{18}H_{17}N_6O^+$[M+H]$^+$: 333.1464, Found: 333.1441.

$N^5,N^6$-bis(2-methoxyphenyl)-[1,2,5]oxadiazolo[3,4-b]pyrazine-5,6-diamine (3d). Synthesized by general procedure A. 16%, yellow solid. $^1$H NMR (400 MHz, Acetone-$d_6$) δ 9.03-8.64 (m, 2H), 7.28-6.97 (m, 8H), 3.92 (s, 6H); HRMS (ESI$^+$): Calcd for $C_{18}H_{17}N_6O_3^+$[M+H]$^+$: 365.1362, Found: 365.1345.

$N^5,N^6$-bis(3-methoxyphenyl)-[1,2,5]oxadiazolo[3,4-b]pyrazine-5,6-diamine (3e). Synthesized by general procedure A. 32%, off-white solid. $^1$H NMR (400 MHz, Acetone-$d_6$) δ 9.64 (brs, 2H), 7.80-7.03 (brm, 4H), 7.34 (t, J=8.1 Hz, 2H), 6.80-6.75 (m, 2H), 3.82 (s, 6H); HRMS (ESI$^+$): Calcd for $C_{18}H_{17}N_6O_3^+$[M+H]$^+$: 365.1362, Found: 365.1370.

$N^5,N^6$-bis(4-methoxyphenyl)-[1,2,5]oxadiazolo[3,4-b]pyrazine-5,6-diamine (3f). Synthesized by general procedure A. 47%, yellow solid. $^1$H NMR (400 MHz, Acetone-$d_6$) δ 9.35 (s, 2H), 7.91-7.43 (brm, 4H), 7.05-6.95 (m, 4H), 3.83 (s, 6H); HRMS (ESI$^+$): Calcd for $C_{18}H_{17}N_6O_3^+$[M+H]$^+$: 365.1362, Found: 365.1367.

$N^5,N^6$-bis(2-ethoxyphenyl)-[1,2,5]oxadiazolo[3,4-b]pyrazine-5,6-diamine (3g). Synthesized by general procedure A. 54%, light yellow solid. $^1$H NMR (400 MHz, Acetone-$d_6$) δ 9.61 (brs, 2H), 7.95-7.06 (brm, 4H), 7.32 (t, J=8.1 Hz, 2H), 6.80-6.71 (m, 2H) 4.08 (q, J=7.0 Hz, 2H), 1.38 (t, J=7.0 Hz, 9H); HRMS (ESI$^+$): Calcd for $C_{20}H_{21}N_6O_3^+$[M+H]$^+$: 393.1675, Found: 393.1674.

$N^5,N^6$-bis(3-ethoxyphenyl)-[1,2,5]oxadiazolo[3,4-b]pyrazine-5,6-diamine (3h). Synthesized by general procedure A. 27%, yellow solid. $^1$H NMR (400 MHz, Acetone-$d_6$) δ 9.86-8.96 (brm, 1H), 7.94-7.13 (brm, 5H), 6.84-6.44 (brm, 3H), 4.08 (q, J=7.0 Hz, 4H), 1.38 (t, J=7.0 Hz, 6H; HRMS (ESI$^+$): Calcd for $C_{20}H_{21}N_6O_3^+$[M+H]$^+$: 393.1675, Found: 393.1656.

$N^5,N^6$-bis(4-ethoxyphenyl)-[1,2,5]oxadiazolo[3,4-b]pyrazine-5,6-diamine (3i). Synthesized by general procedure A. 73%, yellow solid. $^1$H NMR (400 MHz, Acetone-$d_6$) δ 9.15 (s, 2H), 8.01-7.50 (brm, 4H), 7.04-6.94 (m, 4H), 4.07 (q, J=7.0 Hz, 4H), 1.38 (t, J=6.9 Hz, 6H); HRMS (ESI$^+$): Calcd for $C_{20}H_{21}N_6O_3^+$[M+H]$^+$: 393.1675, Found: 393.1673.

3,3'-([1,2,5]oxadiazolo[3,4-b]pyrazine-5,6-diylbis(azanediyl))diphenol (3j). Synthesized by general procedure A. 43%, light yellow solid. $^1$H NMR (500 MHz, Acetone-$d_6$) δ 8.71 (brs, 2H), 7.93-7.39 (brm, 2H), 7.36-6.86 (m, 4H), 6.74-6.62 (brm, 2H), 6.68 (d, J=7.2 Hz, 2H); HRMS (ESI$^+$): Calcd for $C_6H_{13}N_6O_3^+$[M+H]$^+$: 337.1049, Found: 337.1044.

$N^5,N^6$-bis(2-(trifluoromethoxy)phenyl)-[1,2,5]oxadiazolo[3,4-b]pyrazine-5,6-diamine (3k). Synthesized by general procedure A. 20%, off-white solid. $^1$H NMR (400 MHz, Acetone-$d_6$) δ 10.23 (brs, 2H), 8.12 (brs, 2H), 7.54-7.46 (m, 4H), 7.38-7.29 (m, 2H); $^{19}$F NMR (376 MHz, Acetone-$d_6$) δ–58.69 (s, 6 F); HRMS (ESI$^-$): Calcd for $C_{18}H_9F_6N_6O_3^-$ [M–H]: 471.0646, Found: 471.0657.

$N^5,N^6$-bis(3-(trifluoromethoxy)phenyl)-[1,2,5]oxadiazolo[3,4-b]pyrazine-5,6-diamine (3l). Synthesized by general procedure A. 69%, yellow solid. $^1$H NMR (400 MHz, Acetone-$d_6$) δ 10.00 (s, 2H), 8.01-7.64 (brm, 4H), 7.58 (t, J=8.1 Hz, 2H), 7.21-7.13 (m, 2H); $^{19}$F NMR (376 MHz, Acetone-d$_6$) δ−58.47 (s, 6 F); HRMS (ESI$^+$): Calcd for C$_{18}$H$_{11}$ F$_6$N$_6$O$_3^+$[M+H]$^+$: 473.0797, Found: 473.0773.

N$^5$,N$^6$-bis(4-(trifluoromethoxy)phenyl)-[1,2,5]oxadiazolo[3,4-b]pyrazine-5,6-diamine (3m). Synthesized by general procedure A. 40%, off-white solid. $^1$H NMR (400 MHz, Acetone-d$_6$) δ 9.09 (brs, 2H), 8.03-7.55 (brm, 4H), 7.49 (d, J=8.5 Hz, 4H); $^{19}$F NMR (376 MHz, Acetone-d$_6$) δ−58.78 (s, 6 F); HRMS (ESI$^+$): Calcd for C$_{18}$H$_{11}$ F$_6$N$_6$O$_3^+$ [M+H]$^+$: 473.0797, Found: 473.0792.

N$^5$,N$^6$-bis(3-fluorophenyl)-[1,2,5]oxadiazolo[3,4-b]pyrazine-5,6-diamine (3n). Synthesized by general procedure A. 68%, light yellow solid. $^1$H NMR (400 MHz, Acetone-d$_6$) δ 9.83 (brs, 2H), 8.05-7.20 (brm, 4H), 7.50-7.44 (m, 2H), 7.03-6.93 (m, 2H); $^{19}$F NMR (376 MHz, Acetone-d$_6$) δ−113.16--113.23 (m, 2 F); HRMS (ESI$^+$): Calcd for C$_6$H$_{11}$ F$_2$N$_6$O$^+$ [M+H]$^+$: 341.0957, Found: 341.0943.

N,N'-(([1,2,5]oxadiazolo[3,4-b]pyrazine-5,6-diylbis(azanediyl))bis(4,1-phenylene))bis(2,2,2-trifluoroacetamide) (3o). Synthesized by general procedure A. 22%, yellow solid. $^1$H NMR (400 MHz, Acetone-d$_6$) δ 10.38 (s, 2H), 9.61 (s, 2H), 8.00-7.94 (m, 4H), 7.86-7.81 (m, 4H); $^{19}$F NMR (376 MHz, Acetone-d$_6$) δ−76.58 (s, 6 F); HRMS (ESI$^+$): Calcd for C$_{20}$H$_{13}$ F$_6$N$_8$O$_3^+$[M+H]$^+$: 527.1015, Found: 527.1009.

4,4'-([1,2,5]oxadiazolo[3,4-b]pyrazine-5,6-diylbis(azanediyl))dibenzonitrile (3p). Synthesized by general procedure A. 19%, off-white solid. $^1$H NMR (400 MHz, Acetone-d$_6$) δ 9.78 (s, 2H), 8.25-8.17 (m, 4H), 7.92-7.85 (m, 4H); HRMS (ESI$^+$): Calcd for C$_{18}$H$_{11}$N$_8$O+[M+H]$^+$: 355.1056, Found: 355.1040.

N$^5$,N$^6$-bis(2-(trifluoromethyl)phenyl)-[1,2,5]oxadiazolo[3,4-b]pyrazine-5,6-diamine (3q). Synthesized by general procedure A. 52%, light yellow solid. $^1$H NMR (400 MHz, Acetone-d$_6$) δ 9.40 (s, 2H), 8.03-7.76 (m, 6H), 7.64 (t, J=7.7 Hz, 2H); $^{19}$F NMR (376 MHz, Acetone-d$_6$) δ−61.18 (s, 6 F); HRMS (ESI$^+$): Calcd for C$_{18}$H$_{11}$ F$_6$N$_6$O$^+$[M+H]$^+$: 441.0899, Found: 441.0892.

N$^5$,N$^6$-bis(3-(trifluoromethyl)phenyl)-[1,2,5]oxadiazolo[3,4-b]pyrazine-5,6-diamine (3r). Synthesized by general procedure A. 50%, off-white solid. $^1$H NMR (400 MHz, Acetone-d$_6$) δ 10.11 (brs, 2H), 8.37-7.73 (brm, 4H), 7.70 (t, J=7.9 Hz, 2H), 7.55 (d, J=7.8 Hz, 2H); $^{19}$F NMR (376 MHz, Acetone-d$_6$) δ−63.20 (s, 6 F); HRMS (ESI$^+$): Calcd for C$_{18}$H$_{11}$ F$_6$N$_6$O$^+$[M+H]$^+$: 441.0899, Found: 441.0887.

N$^5$,N$^6$-bis(4-(trifluoromethyl)phenyl)-[1,2,5]oxadiazolo[3,4-b]pyrazine-5,6-diamine (3s). Synthesized by general procedure A. 63%, light yellow solid. $^1$H NMR (400 MHz, Acetone-d$_6$) δ 10.17 (s, 2H), 8.10-7.80 (brm, 4H), 7.80 (d, J=8.3 Hz, 4H); $^{19}$F NMR (376 MHz, Acetone-d$_6$) δ−62.53 (s, 6 F); HRMS (ESI$^+$): Calcd for C$_{18}$H$_{11}$ F$_6$N$_6$O$^+$[M+H]$^+$: 441.0899, Found: 441.0875.

Dimethyl 4,4'-([1,2,5]oxadiazolo[3,4-b]pyrazine-5,6-diylbis(azanediyl))dibenzoate (3t). Synthesized by general procedure A. 23%, yellow solid. $^1$H NMR (400 MHz, Acetonitrile-d$_3$) δ 9.74 (s, 2H), 8.06 (d, J=7.8 Hz, 4H), 8.30-7.73 (brm, 4H), 3.88 (s, 6H); HRMS (ESI$^+$): Calcd for C$_{20}$H$_{17}$N$_6$O$_5^+$[M+H]$^+$: 421.1260, Found: 421.1252.

4,4'-([1,2,5]Oxadiazolo[3,4-b]pyrazine-5,6-diylbis(azanediyl))dibenzoic acid (3u). Synthesized by general procedure A. 38%, off-white solid. $^1$H NMR (400 MHz, Acetone-d$_6$) δ 12.24-10.92 (brs, 2H), 9.72 (s, 2H), 8.31-8.25 (m, 4H), 8.16-8.08 (m, 4H); GCMS (EI): Calcd for C$_{18}$H$_{12}$N$_6$NaO$_5$ [M+Na]: 415.0, Found: 415.1.

2,2'-(([1,2,5]oxadiazolo[3,4-b]pyrazine-5,6-diylbis(azanediyl))bis(4,1-phenylene))bis(ethan-1-ol) (3v). Synthesized by general procedure A. 40%, yellow solid. $^1$H NMR (400 MHz, Acetone-d$_6$) δ 9.47 (s, 2H), 7.83-7.76 (m, 4H), 7.38-7.31 (m, 4H), 3.79 (q, J=6.5 Hz, 4H), 3.70 (t, J=5.3 Hz, 2H), 2.85 (t, J=6.9 Hz, 4H); HRMS (ESI$^+$): Calcd for C$_{20}$H$_{21}$N$_6$O$_3^+$[M+H]$^+$: 393.1675, Found: 393.1700.

N$^5$,N$^6$-bis(2-fluoro-4-(trifluoromethyl)phenyl)-[1,2,5]oxadiazolo[3,4-b]pyrazine-5,6-diamine (3w). Synthesized using General Procedure A. $^1$H NMR ((CD$_3$)$_2$CO, 400 MHz) δ 10.58-10.04 (brm, 2H), 7.93-7.77 (brm, 2H), 7.82 (t, 2H, J=8.5 Hz), 7.72-7.56 (brm, 2H). HRMS (ESI$^+$) m/z calcd for C$_{18}$H$_9$ F$_8$N$_6$O [M+H]$^+$: 477.0705, Found: 477.0701.

N$^5$,N$^6$-bis(3-fluoro-4-(trifluoromethyl)phenyl)-[1,2,5]oxadiazolo[3,4-b]pyrazine-5,6-diamine (3x). Synthesized using General Procedure A. $^1$H NMR ((CD$_3$)$_2$CO, 400 MHz) δ 10.67-10.04 (brm, 2H), 7.92-7.74 (brm, 2H), 7.81 (t, 2H, J=8.4 Hz), 7.70-7.57 (brm, 2H); $^{19}$F ((CD$_3$)$_2$CO, 376 MHz) δ−61.22 (d, 3 F), −114.5--114.73 (m, 1H). HRMS (ESI$^+$) m/z calcd for C$_{18}$H$_9$ F$_8$N$_6$O [M+H]$^+$: 477.0705, Found: 477.0689.

N$^5$,N$^6$-bis(2-fluoro-5-(trifluoromethyl)phenyl)-[1,2,5]oxadiazolo[3,4-b]pyrazine-5,6-diamine (3y). Synthesized using General Procedure A. $^1$H NMR ((CD$_3$)$_2$CO, 400 MHz, asterisk denotes tautomer peaks) δ 11.57-10.94* (brs, 1H), 10.22-9.68* (brs, 1H), 8.86-7.82 (brm, 2H), 7.68-7.62 (m, 2H), 7.55 (t, 2H, J=9.8 Hz). HRMS (ESI$^+$) m/z calcd for C$_{18}$H$_{19}$ F$_8$N$_6$O [M+H]$^+$: 477.0705 Found: 477.0711.

N$^5$,N$^6$-bis(3,5-bis(trifluoromethyl)phenyl)-[1,2,5]oxadiazolo[3,4-b]pyrazine-5,6-diamine (z). Synthesized using Generic Procedure A. $^1$H NMR ((CD$_3$)$_2$CO, 400 MHz, asterisk denotes tautomer peaks) δ 11.45-10.84* (brs, 1H), 10.59-10.10 (brs, 1H), 8.80-7.98 (brm, 4H), 7.87 (s, 2H). HRMS (ESI$^-$) m/z calcd for C$_{20}$H$_7$ F$_{12}$N$_6$O [M−H]$^-$: 575.0495, Found: 575.0509.

N$^5$,N$^6$-bis(2-fluoro-3-(trifluoromethyl)phenyl)-[1,2,5]oxadiazolo[3,4-b]pyrazine-5,6-diamine (3aa). Synthesized using General Procedure A. $^1$H NMR ((CD$_3$)$_2$CO, 400 MHz, asterisk denotes tautomer peaks) δ 11.48-11.12* (brm, 1H), 10.10-9.76 (brm, 2H), 7.67-7.42 (m, 6H). HRMS (ESI$^+$) m/z calcd for C$_8$H$_9$ F$_8$N$_6$O [M+H]$^+$: 477.0705 Found: 477.0736.

N$^5$,N$^6$-bis(3-fluoro-4-(trifluoromethoxy)phenyl)-[1,2,5]oxadiazolo[3,4-b]pyrazine-5,6-diamine (3bb). Synthesized using General Procedure A. $^1$H NMR ((CD$_3$)$_2$CO, 400 MHz) δ 10.44-9.66 (brs, 2H), 8.15-7.58 (brm, 4H), 7.50 (t, 2H, J=9.5 Hz). HRMS (ESI$^+$) m/z calcd for C$_{18}$H$_9$ F$_8$N$_6$O$_3$ [M+H]$^+$: 509.0603, Found: 508.0639.

N$^5$,N$^6$-bis(3,5-difluorophenyl)-[1,2,5]oxadiazolo[3,4-b]pyrazine-5,6-diamine (3cc). Synthesized using General Procedure A. $^1$H NMR ((CD$_3$)$_2$CO, 400 MHz) δ 10.43-9.63 (brm, 2H), 7.82-7.03 (brm, 4H), 6.89-6.81 (m, 2H). HRMS (ESI$^+$) m/z calcd for C$_6$H$_9$ F$_4$N$_6$O [M+H]$^+$: 377.0768, Found: 377.0764.

3,3'-([1,2,5]Oxadiazolo[3,4-b]pyrazine-5,6-diylbis(azanediyl))bis(4-fluorophenol)(3dd). Synthesized by General Procedure A. 21%, light yellow solid. $^1$H NMR (400 MHz, Acetonitrile-d$_3$) δ 8.22 (brs, 4H), 7.48-7.20 (brm, 2H), 7.08 (dd, J=10.6, 8.9 Hz, 2H), 6.72-6.54 (m, 2H); $^{19}$F NMR (376 MHz, Acetonitrile-d$_3$) δ−140.05 (s, 2 F); HRMS (ESI$^+$): Calcd for C$_{16}$H$_{11}$ F$_2$N$_6$O$_3$[M+H]$^+$: 373.0861, Found: 373.0873.

N$^5$,N$^6$-diphenyl-[1,2,5]oxadiazolo[3,4-b]pyrazine-5,6-diamine (3ee). Synthesized by General Procedure A. 98%, light yellow solid. $^1$H NMR (400 MHz, Acetone-d$_6$) δ 9.96-9.33 (brs, 2H), 8.06-7.51 (brm, 4H), 7.47-7.42 (m, 4H), 7.24-7.18 (m, 2H); HRMS (ESI$^+$) Calcd for C$_6$H$_{13}$N$_6$O [M+H]$^+$: 305.1145, Found: 305.1158.

N$^5$-(2-fluorophenyl)-N$^6$-phenyl-[1,2,5]oxadiazolo[3,4-b]pyrazine-5,6-diamine (4a). Synthesized by general procedure B. 44%, yellow solid. $^1$H NMR (400 MHz, Acetone-d$_6$)

δ 11.44-9.05 (brm, 2H), 7.76 (brs, 3H), 7.45 (t, J=7.8 Hz, 2H), 7.35-7.14 (m, 4H); $^{19}$F NMR (376 MHz, Acetonitrile-d$_3$) δ −122.05--130.05 (m, 1 F); HRMS (ESI$^+$): Calcd for C$_{16}$H$_{12}$ FN$_6$O$^+$ [M+H]$^+$: 323.1057, Found: 323.1051.

N$^5$-(2-fluorophenyl)-N$^6$-(pyridin-2-yl)-[1,2,5]oxadiazolo[3,4-b]pyrazine-5,6-diamine (4b). Synthesized by general procedure B. 12%, off-white solid. $^1$H NMR (400 MHz, Acetonitrile-d$_3$) δ 10.16 (s, 1H), 8.65 (t, J=8.0 Hz, 1H), 8.18 (d, J=5.7 Hz, 1H), 8.05-7.99 (m, 1H), 7.44 (d, J=8.7 Hz, 1H), 7.37-7.11 (m, 5H); $^{19}$F NMR (376 MHz, Acetonitrile-d$_3$) δ−129.95--130.15 (m, 1 F); HRMS (ESI$^+$): Calcd for C$_{15}$H$_{11}$ FN$_7$O$^+$[M+H]$^+$: 324.1009, Found: 324.0997.

N$^5$-(2-fluorophenyl)-N$^6$-(3-fluorophenyl)-[1,2,5]oxadiazolo[3,4-b]pyrazine-5,6-diamine (4c). Synthesized by general procedure B. 42%, off-white solid. $^1$H NMR (400 MHz, Acetone-d$_6$) δ 10.84 (brs, 1H), 9.82 (brs, 1H), 8.24-7.51 (brm, 5H), 7.48 (app. q, J=8.2, 6.6 Hz, 1H), 7.35-7.21 (m, 4H), 6.98 (td, J=8.8, 2.5 Hz, 1H); $^{19}$F NMR (376 MHz, Acetone-d$_6$) δ−113.18--113.24 (m, 1 F), −113.24--113.29 (m, 1 F); HRMS (ESI$^+$): Calcd for C$_6$H$_{11}$ F$_2$N$_6$O$^+$ [M+H]$^+$: 341.0962, Found: 341.0956.

N$^5$-(2-fluorophenyl)-N$^6$-(4-fluorophenyl)-[1,2,5]oxadiazolo[3,4-b]pyrazine-5,6-diamine (4d). Synthesized by general procedure B. 28%, off-white solid. $^1$H NMR (500 MHz, Acetone-d$_6$) δ 10.82 (s, 1H), 9.72 (s, 1H), 8.28-7.56 (brm, 4H), 7.36-7.17 (m, 4H); $^{19}$F NMR (376 MHz, Acetone-d$_6$) δ−118.35--120.14 (m, 1 F), −129.66--129.73 (m, 1 F); HRMS (ESI$^+$): Calcd for C$_{16}$H$_{11}$ F$_2$N$_6$O$^+$ [M+H]$^+$: 341.0962, Found: 341.0967.

N$^5$-(2,3-difluorophenyl)-N$^6$-(2-fluorophenyl)-[1,2,5]oxadiazolo[3,4-b]pyrazine-5,6-diamine (4e). Synthesized by general procedure B. 32%, light yellow solid. $^1$H NMR (400 MHz, Acetone-d$_6$) δ 10.91 (s, 1H), 9.75 (s, 1H), 8.64-8.03 (m, 1H), 7.86-7.42 (m, 1H), 7.35-7.22 (m, 4H), 7.22-7.13 (m, 1H); $^{19}$F NMR (376 MHz, Acetone-d$_6$) δ−139.18--139.86 (m, 1 F), −148.96--154.99 (m, 2 F); HRMS (ESI$^+$): Calcd for C$_6$H$_{10}$ F$_3$N$_6$O$^+$ [M+H]$^+$: 359.0868, Found: 359.0858.

N$^5$-(2,4-difluorophenyl)-N$^6$-(2-fluorophenyl)-[1,2,5]oxadiazolo[3,4-b]pyrazine-5,6-diamine (4f). Synthesized by general procedure B. 16%, light yellow solid. $^1$H NMR (400 MHz, Acetone-d$_6$) δ 10.90 (s, 1H), 9.76 (s, 1H), 8.43-7.45 (brm, 2H), 7.34-7.25 (m, 2H), 7.24-7.16 (m, 2H), 7.17-7.08 (m, 2H); $^{19}$F NMR (376 MHz, Acetone-d$_6$) δ−114.32--116.24 (m, 2 F), −119.15--121.61 (m, 1 F); HRMS (ESI$^+$): Calcd for C$_{16}$H$_{10}$ F$_3$N$_6$O$^+$[M+H]$^+$: 359.0868, Found: 359.0862.

N$^5$-(2-fluorophenyl)-N$^6$-(o-tolyl)-[1,2,5]oxadiazolo[3,4-b]pyrazine-5,6-diamine (4g). Synthesized by general procedure B. 17%, off-white solid. $^1$H NMR (500 MHz, Acetone-d$_6$) δ 9.67-9.54 (brm, 1H), 8.63 (brs, 1H), 7.47-7.41 (m, 1H), 7.40-7.36 (m, 2H), 7.35-7.25 (m, 5H), 2.28 (s, 3H); $^{19}$F NMR (376 MHz, Acetonitrile-d$_3$) δ−122.81--123.46 (m, 1 F); HRMS (ESI$^+$): Calcd for C$_{17}$H$_{14}$ FN$_6$O$^+$[M+H]$^+$: 337.1213, Found: 337.1200.

N$^5$-(2-fluorophenyl)-N$^6$-(m-tolyl)-[1,2,5]oxadiazolo[3,4-b]pyrazine-5,6-diamine (4h). Synthesized by general procedure B. 43%, yellow solid. $^1$H NMR (400 MHz, Acetonitrile-d$_3$) δ 9.10 (brs, 2H), 7.70-7.54 (brs, 1H) (s, 1H), 7.52-7.39 (m, 2H), 7.34 (t, J=8.1 Hz, 1H), 7.31-7.24 (m, 3H), 7.07 (d, J=7.5 Hz, 1H), 2.39 (s, 3H); $^{19}$F NMR (376 MHz, Acetone-d$_6$) δ−118.84--127.22 (m, 1 F); HRMS (ESI$^+$): Calcd for C$_{17}$H$_{14}$ FN$_6$O$^+$ [M+H]$^+$: 337.1213, Found: 337.1203.

N$^5$-(2-fluorophenyl)-N$^6$-(p-tolyl)-[1,2,5]oxadiazolo[3,4-b]pyrazine-5,6-diamine (4i). Synthesized by general procedure B. 40%, light yellow solid. $^1$H NMR (400 MHz, Acetone-d$_6$) δ 10.91 (brs, 1H), 9.77 (brs, 1H), 8.09-7.55 (brm, 2H), 7.49-7.18 (m, 6H), 2.35 (s, 3H); $^{19}$F NMR (376 MHz, Acetone-d$_6$) δ−120.34--128.87 (m, 1 F); HRMS (ESI$^+$): Calcd for C$_{17}$H$_{14}$ FN$_6$O$^+$[M+H]$^+$: 337.1213, Found: 337.1201.

N$^5$-(2-fluorophenyl)-N$^6$-(2-methoxyphenyl)-[1,2,5]oxadiazolo[3,4-b]pyrazine-5,6-diamine (4j). Synthesized by general procedure B. 55%, yellow solid. $^1$H NMR (400 MHz, Acetone-d$_6$) δ 10.05 (s, 1H), 8.78 (s, 1H), 7.33-7.22 (m, 5H), 7.22-7.12 (m, 2H), 7.08 (app. t, J=7.5 Hz, 1H), 3.97 (s, 3H); $^{19}$F NMR (376 MHz, Acetone-d$_6$) δ−124.053--125.57 (m, 1 F); HRMS (ESI$^-$): Calcd for C$_{17}$H$_{12}$ FN$_6$O$_2^-$ [M−H]$^-$: 351.1011, Found: 351.1015.

N$^5$-(2-fluorophenyl)-N$^6$-(3-methoxyphenyl)-[1,2,5]oxadiazolo[3,4-b]pyrazine-5,6-diamine (4k). Synthesized by general procedure B. 50%, yellow solid. $^1$H NMR (400 MHz, Acetone-d$_6$) δ 10.80 (s, 1H), 9.71 (s, 1H), 7.86-7.40 (brm, 2H), 7.35 (t, J=8.1 Hz, 1H), 7.31-7.22 (m, 4H), 3.83 (s, 3H); $^{19}$F NMR (376 MHz, Acetone-d$_6$) δ−124.34--126.26 (brm, 1 F); HRMS (ESI$^-$): Calcd for C$_{17}$H$_{12}$ FN$_6$O$_2^-$ [M−H]$^-$: 351.1011, Found: 351.1003.

N$^5$-(2-fluorophenyl)-N$^6$-(4-methoxyphenyl)-[1,2,5]oxadiazolo[3,4-b]pyrazine-5,6-diamine (4l). Synthesized by general procedure B. 38%, yellow solid. $^1$H NMR (400 MHz, Acetone-d$_6$) δ 10.65 (brs, 1H), 9.65 (s, 1H), 8.20-7.46 (brm, 3H), 7.31-7.22 (m, 3H), 7.16-6.90 (m, 2H), 3.83 (s, 3H); $^{19}$F NMR (376 MHz, Acetone-d$_6$) δ−124.80 (s, 1 F); HRMS (ESI$^+$): Calcd for C$_{17}$H$_{14}$ FN$_6$O$_2^+$[M+H]$^+$: 353.1162, Found: 353.1177.

N$^5$-(2-ethoxyphenyl)-N$^6$-(2-fluorophenyl)-[1,2,5]oxadiazolo[3,4-b]pyrazine-5,6-diamine (4m). Synthesized by general procedure B. 39%, yellow solid. $^1$H NMR (400 MHz, Acetone-d$_6$) δ 10.81 (s, 1H), 10.20 (s, 1H), 8.76 (s, 1H), 7.36 (brs, 1H), 7.31-7.20 (m, 3H), 7.20-7.04 (m, 3H), 4.22 (q, J=7.0 Hz, 2H), 1.42 (t, J=6.9 Hz, 3H); $^{19}$F NMR (376 MHz, Acetone-d$_6$) δ−123.40--126.20 (brm, 1 F); HRMS (ESI$^+$): Calcd for C$_8$H$_{16}$ FN$_6$O$_2^+$[M+H]$^+$: 367.1319, Found: 367.1322.

N$^5$-(3-ethoxyphenyl)-N$^6$-(2-fluorophenyl)-[1,2,5]oxadiazolo[3,4-b]pyrazine-5,6-diamine (4n). Synthesized by general procedure B. 22%, yellow solid. $^1$H NMR (400 MHz, Acetone-d$_6$) δ 10.76 (brs, 1H), 9.77 (brs, 1H), 7.95-7.41 (brm, 2H), 7.33 (t, J=8.0 Hz, 1H), 7.31-7.23 (m, 4H), 6.77 (app d, J=6.9 Hz, 1H), 4.09 (q, J=7.0 Hz, 2H), 1.39 (t, J=7.0 Hz, 3H); $^{19}$F NMR (376 MHz, Acetonitrile-d$_3$) δ−122.42--130.56 (brm, 1 F); HRMS (ESI$^+$): Calcd for C$_8$H$_{16}$ FN$_6$O$_2^+$ [M+H]$^+$: 367.1319, Found: 367.1324.

N$^5$-(4-ethoxyphenyl)-N$^6$-(2-fluorophenyl)-[1,2,5]oxadiazolo[3,4-b]pyrazine-5,6-diamine (4o). Synthesized by general procedure B. 55%, yellow solid. $^1$H NMR (400 MHz, Acetone-d$_6$) δ 9.64 (brs, 2H), 7.80 (brs, 3H), 7.32-7.22 (m, 3H), 7.03-6.96 (m, 2H), 4.08 (q, J=7.0 Hz, 2H), 1.38 (t, J=7.0 Hz, 3H); $^{19}$F NMR (376 MHz, Acetone-d$_6$) δ−124.93--127.24 (brm, 1 F); HRMS (ESI$^+$): Calcd for C$_{18}$H$_{16}$ FN$_6$O$_2^+$[M+H]$^+$: 367.1319, Found: 367.1313.

3-((6-((2-fluorophenyl)amino)-[1,2,5]oxadiazolo[3,4-b]pyrazin-5-yl)amino)phenol (4p). Synthesized by general procedure B. 33%, yellow solid. $^1$H NMR (400 MHz, Acetone-d$_6$) δ 9.42 (s, 1H), 8.27-8.17 (m, 1H), 7.42-7.27 (m, 3H), 7.19 (t, J=8.1 Hz, 1H), 6.73 (t, J=2.2 Hz, 1H), 6.71-6.66 (m, 1H), 6.65-6.60 (m, 1H), 5.00 (s, 2H); $^{19}$F NMR (376 MHz, Acetone-d$_6$) δ−124.79--124.95 (m, 1 F); HRMS (ESI$^+$): Calcd for C$_6$H$_{12}$ FN$_6$O$_2^+$[M+H]$^+$: 339.1006, Found: 339.1004.

N$^5$-(2-fluorophenyl)-N$^6$-(2-(trifluoromethoxy)phenyl)-[1,2,5]oxadiazolo[3,4-b]pyrazine-5,6-diamine (4q). Synthesized by general procedure B. 14%, off-white solid. $^1$H NMR (400 MHz, Acetone-d$_6$) δ 11.10 (brs, 1H), 9.88 (brs, 1H), 7.56-7.40 (m, 2H), 7.39-7.23 (m, 6H); $^{19}$F NMR (376 MHz, Acetone-d$_6$) δ−58.48 (s, 3 F), −123.69-−131.84 (brd, 1 F); HRMS (ESI$^+$): Calcd for C$_{17}$H$_{11}$ F$_4$N$_6$O$_2^+$[M+H]$^+$: 407.0880, Found: 407.0897.

N$^5$-(2-fluorophenyl)-N$^6$-(3-(trifluoromethoxy)phenyl)-[1,2,5]oxadiazolo[3,4-b]pyrazine-5,6-diamine (4r). Synthesized by general procedure B. 59%, yellow solid. $^1$H NMR (400 MHz, Acetone-d$_6$) δ 10.02 (brs, 2H), 8.21-7.65 (brm, 3H), 7.58 (t, J=8.2 Hz, 1H), 7.33-7.22 (m, 3H), 7.17 (d, J=8.1 Hz, 1H); $^{19}$F NMR (376 MHz, Acetone-d$_6$) δ−58.45 (s, 3 F), −120.56-−130.21 (m, 1 F); HRMS (ESI$^+$): Calcd for C$_{17}$H$_{11}$ F$_4$N$_6$O$_2^+$[M+H]$^+$: 407.0880, Found: 407.0887.

N$^5$-(2-fluorophenyl)-N$^6$-(4-(trifluoromethoxy)phenyl)-[1,2,5]oxadiazolo[3,4-b]pyrazine-5,6-diamine (4s). Synthesized by general procedure B. 28%, light yellow solid. $^1$H NMR (400 MHz, Acetone-d$_6$) δ 10.96 (brs, 1H), 9.80 (brs, 1H), 8.36-7.53 (brm, 3H), 7.43 (d, J=7.9 Hz, 2H), 7.34-7.11 (m, 3H); $^{19}$F NMR (376 MHz, Acetone-d$_6$) δ−59.45 (s, 3 F), −122.88-−126.12 (brd, 1 F); HRMS (ESI$^+$): Calcd for C$_{17}$H$_{11}$ F$_4$N$_6$O$_2^+$[M+H]$^+$: 407.0880, Found: 407.0872.

2,2,2-Trifluoro-N-(4-((6-((2-fluorophenyl)amino)-[1,2,5]oxadiazolo[3,4-b]pyrazin-5-yl)amino)phenyl)acetamide (4t). Synthesized by general procedure B. 18%, yellow solid. $^1$H NMR (400 MHz, Acetonitrile-d$_3$) δ 9.23 (brs, 2H), 7.87-7.46 (brm, 6H), 7.36-7.21 (m, 3H); $^{19}$F NMR (376 MHz, Acetonitrile-d$_3$) δ−76.46-−76.75 (m, 3 F), −125.89 (s, 1 F); HRMS (ESI$^+$): Calcd for C$_8$H$_{12}$ F$_4$N$_7$O$_2^+$[M+H]$^+$: 434.0989, Found: 434.0988.

N$^5$-(2-fluorophenyl)-N$^6$-(2-(trifluoromethyl)phenyl)-[1,2,5]oxadiazolo[3,4-b]pyrazine-5,6-diamine (4u). Synthesized by general procedure B. 27%, off-white solid. $^1$H NMR (400 MHz, Acetone-d$_6$) δ 11.13 (s, 1H), 9.82 (s, 1H), 8.67 (s, 1H), 7.79 (d, J=7.9 Hz, 1H), 7.71 (t, J=7.7 Hz, 1H), 7.51-7.19 (m, 5H); $^{19}$F NMR (376 MHz, Acetone-d$_6$) δ−62.71 (s, 3 F), −131.01-−131.82 (m, 1 F); HRMS (ESI$^+$): Calcd for C$_{17}$H$_{11}$ F$_4$N$_6$O$^+$ [M+H]$^+$: 391.0930, Found: 391.0932.

N$^5$-(2-fluorophenyl)-N$^6$-(3-(trifluoromethyl)phenyl)-[1,2,5]oxadiazolo[3,4-b]pyrazine-5,6-diamine (4v). Synthesized by general procedure B. 49%, off-white solid. $^1$H NMR (400 MHz, Acetone-d$_6$) δ 10.82 (brs, 1H), 9.90 (brs, 1H), 8.49-7.92 (brm, 3H), 7.70 (t, J=8.0 Hz, 1H), 7.55 (d, J=7.8 Hz, 1H), 7.36-7.19 (m, 3H); $^{19}$F NMR (376 MHz, Acetone-d$_6$) δ−63.03-−63.34 (m, 3 F), −125.05-−125.39 (m, 1 F); HRMS (ESI$^+$): Calcd for C$_{17}$H$_{11}$ F$_4$N$_6$O$^+$ [M+H]$^+$: 391.0930, Found: 391.0917.

N$^5$-(2-fluorophenyl)-N$^6$-(4-(trifluoromethyl)phenyl)-[1,2,5]oxadiazolo[3,4-b]pyrazine-5,6-diamine (4w). Synthesized by general procedure B. 44%, off-white solid. $^1$H NMR (400 MHz, Acetone-d$_6$) δ 10.97 (brs, 1H), 9.87 (brs, 1H), 8.60-7.85 (brm, 3H), 7.80 (d, J=8.4 Hz, 2H), 7.35-7.22 (m, 3H); $^{19}$F NMR (376 MHz, Acetone-d$_6$) δ−62.52 (s, 3 F), −125.19 (s, 1 F); HRMS (ESI$^+$): Calcd for C$_{17}$H$_{10}$ F$_4$N$_6$NaO [M+Na]$^+$: 413.0750, Found: 413.0740.

N$^5$-(3-(trifluoromethyl)phenyl)-N$^6$-(4-(trifluoromethyl)phenyl)-[1,2,5]oxadiazolo[3,4-b]pyrazine-5,6-diamine (4x). Synthesized by general procedure B. 26%, beige solid. $^1$H NMR (400 MHz, Acetone-d$_6$) δ 10.04 (brs, 2H), 8.34-7.82 (brm, 4H), 7.70 (t, J=7.9 Hz, 2H), 7.55 (d, J=7.7 Hz, 2H); $^{19}$F NMR (376 MHz, Acetone-d$_6$) δ−62.50 (s, 3 F), −63.21 (s, 3 F); HRMS (ESI$^-$): Calcd for C$_{18}$H$_9$ F$_6$N$_6$O$^-$ [M−H]: 439.0748, Found: 439.0759.

Methyl 4-((6-((2-fluorophenyl)amino)-[1,2,5]oxadiazolo[3,4-b]pyrazin-5-yl)amino)benzoate (4y). Synthesized by general procedure B. 13%, yellow solid. $^1$H NMR (400 MHz, Acetone-d$_6$) δ 8.11-8.03 (m, 2H), 7.98 (d, J=8.4 Hz, 2H), 7.84-7.66 (m, 2H), 7.31-7.20 (m, 3H), 6.72-6.62 (m, 1H), 3.89 (s, 3H); $^{19}$F NMR (376 MHz, Acetone-d$_6$) δ−125.73-−127.19 (brm, 1 F); HRMS (ESI$^+$): Calcd for C$_8$H$_{14}$ FN$_6$O$_3^+$[M+H]$^+$: 381.1111, Found: 381.1112.

4-Fluoro-3-((6-((2-fluorophenyl)amino)-[1,2,5]oxadiazolo[3,4-b]pyrazin-5-yl)amino)phenol (4z). Synthesized by general procedure B. 22%, off-white solid. $^1$H NMR (400 MHz, Acetonitrile-d$_3$) δ 8.79 (brs, 1H), 8.05 (td, J=8.1, 2.4 Hz, 1H), 7.41-7.24 (m, 3H), 7.12 (dd, J=11.0, 8.8 Hz, 1H), 6.79 (dd, J=7.6, 2.9 Hz, 1H), 6.62-6.56 (m, 1H), 4.49 (brs, 2H); $^{19}$F NMR (376 MHz, Acetonitrile-d$_3$) δ−124.06-−124.63 (m, 1 F), −138.91-−139.40 (m, 1 F); HRMS (ESI$^+$): Calcd for C$_{16}$H$_{11}$ F$_2$N$_6$O$_2^+$[M+H]$^+$: 357.0912, Found: 357.0878.

N$^5$-(3,5-bis(trifluoromethyl)phenyl)-N$^6$-(2-fluorophenyl)-[1,2,5]oxadiazolo[3,4-b]pyrazine-5,6-diamine (4aa). Synthesized using General Procedure B. $^1$H NMR ((CD$_3$)$_2$CO, 400 MHz, asterisk denotes tautomer peaks) δ 11.29-10.62* (brs, 1H), 10.32-9.54 (brs, 1H), 8.91-8.04 (brm, 3H), 7.85 (s, 1H), 7.34-7.25 (m, 3H). HRMS (ESI$^+$) m/z calcd for C$_8$H$_{10}$ F$_7$N$_6$O [M+H]$^+$: 459.0799 Found: 459.0796.

N$^5$-(2-fluoro-3-(trifluoromethyl)phenyl)-N$^6$-(2-fluorophenyl)-[1,2,5]oxadiazolo[3,4-b]pyrazine-5,6-diamine (4bb). Synthesized using General Procedure B. $^1$H NMR ((CD$_3$)$_2$CO, 400 MHz, asterisk denotes tautomer peaks) δ 11.32-10.84* (brs, 1H), 9.95-9.56 (brs, 1H), 8.57-7.67 (brm, 2H), 7.59 (t, 1H, J=7.7 Hz), 7.50 (t, 1H, J=7.7 Hz), 7.35-7.24 (m, 3H). HRMS (ESI$^+$) m/z calcd for C$_{17}$H$_{10}$ F$_8$N$_6$O [M+H]$^+$: 409.0831 Found: 409.0833.

N$^5$,N$^6$-bis(2-fluorophenyl)-N$^5$-methyl-[1,2,5]oxadiazolo[3,4-b]pyrazine-5,6-diamine (6a). N$^6$-bis(2-fluorophenyl)-[1,2,5]oxadiazolo[3,4-b]pyrazine-5,6-diamine (10 mg, 0.029 mmol) was dissolved in acetone (0.150 mL) with K$_2$CO$_3$ (4.1 mg, 0.029 mmol) and methyliodide (0.100 mL, 0.117 mmol). The reaction mixture was refluxed for 17 h. The resulting reaction mixture was then concentrated via vacuum, and the residue was purified by silica gel column chromatography (0%-10% ethyl acetate/hexanes) to yield the title compound (5 mg, 50%) as an off-white solid. $^1$H NMR (400 MHz, Acetone-d$_6$) δ 9.93 (s, 1H), 8.60 (t, J=8.1 Hz, 1H), 7.38-7.18 (m, 7H), 3.30 (s, 3H); $^{19}$F NMR (376 MHz, Acetone-d$_6$) δ−125.95-−126.15 (m, 1 F), −129.66-−129.88 (m, 1 F); HRMS (ESI$^+$): Calcd for C$_{17}$H$_{13}$ F$_2$N$_6$O [M+H+]$^+$: 355.1119, Found: 355.1112.

N$^5$,N$^6$-bis(2-fluorophenyl)-N$^5$,N$^6$-dimethyl-[1,2,5]oxadiazolo[3,4-b]pyrazine-5,6-diamine (6b). N$^6$-bis(2-fluorophenyl)-[1,2,5]oxadiazolo[3,4-b]pyrazine-5,6-diamine (10 mg, 0.029 mmol) was dissolved in acetone (0.150 mL) with K$_2$CO$_3$ (4.1 mg, 0.029 mmol) and methyliodide (0.200 mL, 0.234 mmol). The reaction mixture was refluxed for 17 h. The resulting reaction mixture was then concentrated via vacuum, and the residue was purified by silica gel column chromatography (0%-10% ethyl acetate/hexanes) to yield the title compound (10 mg, 91%) as an off-white solid. $^1$H NMR (400 MHz, Acetone-d$_6$) δ 7.01-6.77 (m, 6H), 6.49 (brt, J=8.0 Hz, 2H), 3.49 (s, 6H); $^{19}$F NMR (376 MHz, Acetone-d$_6$) δ−124.29-−130.12 (brm, 2 F); HRMS (ESI$^+$): Calcd for C$_{18}$H$_5$ F$_2$N$_6$O$^+$[M+H+]$^+$: 369.1275, Found: 369.1275.

N$^5$-(2-fluorophenyl)-N$^6$-methyl-[1,2,5]oxadiazolo[3,4-b]pyrazine-5,6-diamine (7a). Synthesized using General Procedure C. $^1$H NMR (CDCl$_3$, 400 MHz) δ 8.19-7.85 (m, 1H), 7.77-7.37 (m, 1H), 7.30-7.19 (m, 1H), 3.15 (s, 3H). HRMS (ESI$^+$) m/z calcd for C$_1$H$_{10}$ FN$_6$O [M+H]$^+$: 261.0895 Found: 261.0893.

N$^5$-ethyl-N$^6$-(2-fluorophenyl)-[1,2,5]oxadiazolo[3,4-b]pyrazine-5,6-diamine (7b). Synthesized using General Procedure C. $^1$H NMR (CDCl$_3$, 400 MHz) δ 8.57 (bs, 1H), 7.45-7.35 (m, 1H), 7.23-7.14 (m, 2H), 7.05-6.96 (m, 1H), 3.65 (q, 2H, J=6.7 Hz), 1.69 (brs, 1H), 1.35 (t, 3H, J=7.3 Hz); $^{13}$C NMR (CDCl$_3$, 100 MHz) δ 153.1, 152.1, 149.9, 142.3, 136.8, 132.2, 126.8, 125.5, 123.3, 117.2, 36.6, 13.9. HRMS (ESI$^+$) m/z calcd for C$_{12}$H$_{12}$FN$_6$O [M+H]$^+$: 275.1051 Found: 275.1051.

N$^5$-(2-fluorophenyl)-N$^6$-propyl-[1,2,5]oxadiazolo[3,4-b]pyrazine-5,6-diamine (7c). Synthesized using General Procedure C. $^1$H NMR ((CD$_3$)$_2$CO, 400 MHz) δ 9.03-8.55 (brs, 1H), 7.96-7.64 (brm, 1H), 7.31-7.19 (m, 3H), 3.60 (q, 2H, J=6.6 Hz), 1.78 (sextet, 2H, J=7.2 Hz), 1.02 (t, 3H, J=7.4 Hz). $^{19}$F NMR ((CD$_3$)$_2$CO, 376 MHz) δ−123.54 (s, 1 F). HRMS (ESI$^+$) m/z calcd for C$_{13}$H$_{14}$FN$_6$O [M+H]$^+$: 289.1208 Found: 289.1200.

N$^5$-(2-fluorophenyl)-N$^6$-(3,3,3-trifluoropropyl)-[1,2,5]oxadiazolo[3,4-b]pyrazine-5,6-diamine (7d). Synthesized using General Procedure C. $^1$H NMR (CD$_3$OD, 400 MHz) δ 7.89-7.39 (brm, 1H), 7.32-7.17 (m, 3H), 3.84 (t, 2H, J=7.1 Hz), 2.75-2.62 (m, 2H). HRMS (ESI$^+$) m/z calcd for C$_{13}$H$_{11}$F$_4$N$_6$O [M+H]$^+$: 343.0925 Found: 343.0936.

N$^5$-(2-fluorophenyl)-N$^6$-(1-methylpiperidin-4-yl)-[1,2,5]oxadiazolo[3,4-b]pyrazine-5,6-diamine (7e). Synthesized using General Procedure C. $^1$H NMR ((CD$_3$)$_2$CO, 400 MHz) δ 7.87-7.58 (brs, 1H), 7.51 (t, 1H, J=7.8 Hz), 7.28-7.17 (m, 3H), 4.21-4.11 (m, 1H), 2.92 (d, 2H, J=10.9 Hz), 2.31 (s, 3H), 2.24 (t, 2H, J=11.8 Hz), 2.11 (d, 2H, J=12.8 Hz), 1.76 (q, 2H, J=11.7 Hz); $^{19}$F NMR ((CD$_3$)$_2$CO, 376 MHz) δ−123.27 (s, 1 F). HRMS (ESI$^+$) m/z calcd for C$_6$H$_{19}$FN$_7$O [M+H]$^+$: 344.1630 Found: 344.1642.

N$^5$-cyclohexyl-N$^6$-(2-fluorophenyl)-[1,2,5]oxadiazolo[3,4-b]pyrazine-5,6-diamine (7f). Synthesized using General Procedure C. $^1$H NMR ((CD$_3$)$_2$CO, 400 MHz) δ 9.05-8.58 (brm, H), 7.67-7.34 (brm, 1H), 7.32-7.19 (m, 3H), 4.25-4.11 (brm, 1H), 2.20-2.09 (m, 2H), 1.87-1.75 (m, 2H), 1.74-1.65 (m, 1H), 1.54-1.38 (m, 4H), 1.32-1.22 (m, 1H); $^{19}$F NMR ((CD$_3$)$_2$CO, 3.76 MHz) δ−123.13 (s, 1 F). HRMS (ESI$^+$) m/z calcd for C$_{16}$H$_{18}$FN$_6$O [M+H]$^+$: 329.1521 Found: 329.1526.

2-((6-((4-Trifluoromethoxy)phenyl)amino)-[1,2,5]oxadiazolo[3,4-b]pyrazin-5-yl)amino)ethan-1-ol (7g). Synthesized using General Procedure C. 89%, pale yellow solid. $^1$H NMR (400 MHz, Acetone-d$_6$) δ 9.32 (s, 1H), 8.08-7.52 (brm, 3H), 7.43-7.38 (m, 2H), 4.08 (s, 1H), 3.86-3.83 (m, 2H), 3.76-3.74 (m, 2H); $^{19}$F NMR (376 MHz, acetone) δ−58.79 (s, 3 F); HRMS (ESI$^+$): Calcd for C$_{13}$H$_{12}$F$_3$N$_6$O$_3^+$ [M+H]$^+$: 357.0917, Found: 357.0925.

3-((6-((4-(Trifluoromethoxy)phenyl)amino)-[1,2,5]oxadiazolo[3,4-b]pyrazin-5-yl)amino)propan-1-ol (7h). A round-bottom flask containing 5,6-dichloro-[1,2,5]oxadiazolo[3,4-b]pyrazine (2, 0.200 g, 1.05 mmol) was evacuated and refilled with N$_2$ (3x). The flask was placed in an ice bath and the solid was diluted sequentially with anhydrous THF (2 mL), 4-(trifluoromethoxy)aniline (0.13 mL, 0.97 mmol), and Et$_3$N (0.15 mL, 1.1 mmol). The mixture was stirred for 2 h while slowly warming to room temperature. Then, 3-aminopropan-1-ol (0.16 mL, 2.2 mmol) was added and stirring was continued for 2 h. The mixture was concentrated and purified by chromatography on SiO$_2$ (gradient: 0-5% MeOH/CH$_2$Cl$_2$) to yield the title compound (0.247 g, 69%) as a crust-like yellow solid. $^1$H NMR (400 MHz, Acetone-d$_6$) δ 9.15 (s, 1H), 8.07-7.56 (brm, 3H), 7.40 (d, J=8.5 Hz, 2H), 3.82 (s, 1H), 3.75 (t, J=6.8 Hz, 2H), 3.71 (t, J=6.0 Hz, 2H), 1.97-1.90 (m, 2H); $^{19}$F NMR (376 MHz, acetone) δ−58.80 (s, 3 F); HRMS (ESI$^+$): Calcd for C$_{14}$H$_{14}$F$_3$N$_6$O$_3^+$ [M+H]$^+$: 371.1074, Found: 371.1090.

N$^5$-(2-fluorophenyl)-[1,2,5]oxadiazolo[3,4-b]pyrazine-5,6-diamine (7i). At 0° C., the desired 14 derivative (1 equiv.) was dissolved in acetonitrile (0.125 M). While stirring, 4 mL of 14.5 M ammonium hydroxide were slowly added. The mixture was stirred for 16 h. Afterwards, the resulting mixture was concentrated under vacuum to obtain the desired product quantitatively. $^1$H NMR (CD$_3$OD, 400 MHz) δ 7.76-7.65 (bm, 1H), 7.35-7.21 (m, 3H); $^{19}$F (CD$_3$OD, 376 MHz) δ−123.91 (s, 1 F). HRMS (ESI$^+$) m/z calcd for C$_{10}$H$_8$N$_6$OF [M+H]$^+$: 247.0738 Found: 247.0738.

5,6-dichloro-[1,2,5]thiadiazolo[3,4-b]pyrazine (9). 1,2,5-thiadiazole-3,4-diamine (1 equiv.) was dissolved in 10% HCl (6 M solution). Oxalic acid (1.5 equiv.) was added to the solution, and the mixture was heated to reflux for 3 h. After which, the mixture was cooled to rt, filtered, and dried. The resulting dihydroxy white solid was then carried forward crude (1 equiv.) by adding phosphorous pentachloride (6 equiv.) and phosphorous oxychloride (2 M solution). The resulting mixture was heated to 95° C. for 1 h, and excess phosphorous oxychloride was removed via vacuum distillation. The mixture was cooled to 0° C. and washed with water. The title compound was extracted with EtOAc, dried with Na$_2$SO$_4$, and dried via vacuum. The resulting compound was then purified by silica gel column chromatography (0-10% ethyl acetate/hexanes) to yield the title compound (4 mg, 4%) as an off-white solid. $^{13}$C NMR (101 MHz, Acetone-d$_6$) δ 131.13, 128.74. GCMS (EI): Calcd for C$_4$Cl$_2$N$_4$S [M*]: 205.9, Found: 205.9.

N$^5$,N$^6$-bis(2-fluorophenyl)-[1,2,5]thiadiazolo[3,4-b]pyrazine-5,6-diamine (10). Synthesized by general procedure A using 5,6-dichloro-[1,2,5]thiadiazolo[3,4-b]pyrazine. 5%, yellow solid. $^1$H NMR (400 MHz, Acetone-d$_6$) δ 8.87 (s, 2H), 8.13 (dd, J=8.0 Hz, 2H), 7.36-7.25 (m, 6H); $^{19}$F NMR (376 MHz, Acetone-d$_6$) δ−124.74−−124.97 (m); HRMS (ESI$^+$): Calcd for C$_6$H$_{11}$F$_2$N$_6$S$^+$[M+H$^+$]: 357.0734, Found: 357.0727.

N$^5$,N$^6$-bis(2-fluorophenyl)-1H-imidazo[4,5-b]pyrazine-5,6-diamine (11a). Synthesized by general procedure E, and triethylorthoformate was used as the ring closure reagent. 72%, as a yellow solid. $^1$H NMR (500 MHz, DMSO-d$_6$) δ 12.75 (s, 1H), 8.27 (s, 2H), 8.08 (t, 2H, J=8.1 Hz), 7.74 (t, 2H, J=7.7 Hz), 7.27 (ddd, 2H, J=11.4, 8.1, 1.3 Hz), 7.20 (dd, 2H, J=7.7, 1.3 Hz), 7.10 (q, 2H, J=6.8 Hz); $^{13}$C NMR (125 MHz, DMSO-d$_6$) δ 155.0 (d, J=256.9 Hz), 139.9, 139.0, 129.5, 124.9, 124.1, 124.0, 123.6, 116.0 (d, J=19.3 Hz); $^{19}$F NMR (376 MHz, DMSO-d$_6$) δ−122.87 (m, 1 F), −123.95 (m, 1 F); HRMS (ESI$^+$): Calcd for C$_{17}$H$_{12}$F$_2$N$_6$Na$^+$[M+Na]$^+$: 361.0984, Observed: 361.0975.

N$^5$,N$^6$-bis(2-fluorophenyl)-2-methyl-1H-imidazo[4,5-b]pyrazine-5,6-diamine (11b). Synthesized by general procedure E, and triethylorthoacetate was used as the ring closure reagent. 42%, as a yellow solid. $^1$H NMR (500 MHz, DMSO-d$_6$) δ 12.54 (s, 1H), 8.27 (s, 2H), 8.23 (brs, 1H), 8.05 (brs, 1H), 7.70 (brs, 2H), 7.24 (dd, 2H, J=11.3, 8.3 Hz), 7.16 (t, 2H, J=7.6 Hz), 7.05 (brs, 2H), 2.41 (s, 3H); $^{13}$C NMR (125 MHz, DMSO-d$_6$) δ 154.4 (d, J=230.8 Hz), 149.6, 137.5, 129.7, 124.4, 123.1, 122.5, 122.1, 115.5 (d, J=23.3 Hz), 15.3; $^{19}$F NMR (376 MHz, DMSO-d$_6$) δ−123.54 (m, 1 F), −124.98 (m, 1 F); HRMS (ESI$^+$): Calcd for C$_8$H$_{15}$F$_2$N$_6^+$ [M+H]$^+$: 353.1302, Observed: 353.1321.

N$^5$,N$^6$-bis(2-fluorophenyl)-2-phenyl-1H-imidazo[4,5-b]pyrazine-5,6-diamine (tic). Synthesized by general procedure E, and triethylorthobenzoate was used as the ring closure reagent. 57%, as a yellow solid. $^1$H NMR (500 MHz, CDCl$_3$) δ 10.45 (s, 1H), 8.27 (s, 2H), 8.03 (dd, 2H, J=6.6, 2.9 Hz), 7.43 (m, 3H), 7.09 (dd, 2H, J=11.7, 8.8 Hz), 7.04 (t, 2H, J=7.7 Hz), 6.94 (q, 2H, J=6.4 Hz), 6.58 (d, 2H, J=3.4 Hz); $^{13}$C NMR (125 MHz, CDCl$_3$) δ 153.1 (d, J=243.1 Hz), 150.6, 139.5, 130.5, 129.4, 129.2, 129.1, 126.3, 124.5, 122.6, 122.3, 120.2, 115.2; $^{19}$F NMR (376 MHz, CDCl$_3$) δ −130.71 (m, 1 F), −132.48 (m, 1 F); HRMS (ESI$^+$): Calcd for C$_{23}$H$_{17}$ F$_2$N$_6{}^+$[M+H]$^+$: 415.1477, Observed: 415.1470.

N$^5$,N$^6$-bis(2-fluorophenyl)-2-(trifluoromethyl)-1H-imidazo[4,5-b]pyrazine-5,6-diamine (12a). Synthesized by general procedure F. 39%, as a yellow solid. $^1$H NMR (500 MHz, CDCl$_3$) δ 9.89 (s, 1H), 8.08 (t, 1H, J=8.1 Hz), 7.94 (t, 1H, J=8.1 Hz), 7.16-7.02 (m, 6H), 6.75 (s, 1H), 6.57 (s, 1H); $^{13}$C NMR (125 MHz, CDCl$_3$) δ 153.8 (d, J=243.8 Hz), 153.2 (d, J=243.8 Hz), 141.8, 140.8, 138.7, 137.4 (q, J=41.7 Hz), 131.7, 128.4 (d, J=10.2 Hz), 127.7 (d, J=10.2 Hz), 124.7 (d, J=3.5 Hz), 124.5 (d, J=3.5 Hz), 124.3 (d, J=7.5 Hz), 123.3 (d, J=7.5 Hz), 121.8, 121.0, 118.5 (q, J=268.6 Hz), 115.6 (d, J=19.3 Hz), 115.2 (d, J=19.1 Hz); $^{19}$F NMR (376 MHz, CDCl$_3$) δ −68.38 (s, 3 F), −133.33 (m, 1 F), −135.57 (m, 1 F); HRMS (ESI$^+$): Calcd for C$_8$H$_{12}$ F$_5$N$_6{}^+$[M+H]$^+$: 407.1038, Observed: 407.1026.

N$^5$,N$^6$-bis(2-fluoro-5-(trifluoromethyl)phenyl)-2-(trifluoromethyl)-1H-imidazo[4,5-b]pyrazine-5,6-diamine (12b). Synthesized by general procedure F. 57%, as a yellow solid. $^1$H NMR (500 MHz, CDCl$_3$) δ 11.17 (brs, 1H), 8.45 (brs, 1H), 8.08 (brs, 1H), 7.31-7.19 (m, 4H), 7.07 (s, 1H), 6.56 (s, 1H); $^{13}$C NMR (125 MHz, CDCl$_3$) δ 154.8 (d, J=248.9 Hz), 141.3, 139.5, 138.95, 138.92 (q, J=42.0 Hz), 132.6, 129.3, 128.5, 127.2 (q, J=13.5 Hz), 123.8 (q, J=269.4 Hz), 120.1 (d, J=41.5 Hz), 118.5 (q, J=270.5 Hz), 118.1 (d, J=50.9 Hz), 115.8 (d, J=20.7 Hz); $^{19}$F NMR (376 MHz, CDCl$_3$) δ −62.21 (s, 3 F), −64.55 (s, 6 F), −125.29 (m, 1 F), −125.66 (m, 1 F); HRMS (ESI$^+$): Calcd for C$_{20}$H$_{10}$ F$_{11}$N$_6{}^+$ [M+H]$^+$: 543.0786, Observed: 543.0801.

N$^5$,N$^6$-bis(2-fluorophenyl)-2-(trifluoromethyl)-1H-imidazo[4,5-b]pyrazine-5,6-diamine (12c). Synthesized by general procedure F. 41%, as a yellow solid. $^1$H NMR (500 MHz, CDCl$_3$) δ 7.81 (d, 2H, J=8.3 Hz), 7.64 (d, 2H, J=7.8 Hz), 7.50 (t, 2H, J=7.8 Hz), 7.17 (t, 2H, J=7.6 Hz), 6.86 (s, 2H); $^{13}$C NMR (125 MHz, CDCl$_3$) δ 141.5, 138.7 (q, J=41.7 Hz), 138.02, 137.96, 132.9, 126.8, 125.4 (q, J=271.1 Hz), 123.3, 121.7, 120.1, 119.8, 117.4 (q, J=268.9 Hz); $^{19}$F NMR (376 MHz, CDCl$_3$) δ −61.38 (s, 3 F), −64.55 (s, 6 F); HRMS (ESI$^+$): Calcd for C$_{20}$H$_{12}$ F$_9$N$_6{}^+$[M+H]$^+$: 507.0974, Observed: 507.0992.

N$^5$,N$^6$-bis(3,5-bis(trifluoromethyl)phenyl)-2-(trifluoromethyl)-1H-imidazo[4,5-b]pyrazine-5,6-diamine (12d). Synthesized by general procedure F. 33%, as a yellow solid. $^1$H NMR (500 MHz, Acetone-d$_6$) δ 13.27 (s, 1H), 8.91 (s, 2H), 8.40 (s, 4H), 7.64 (s, 2H); $^{13}$C NMR (125 MHz, Acetone-d$_6$) δ 143.9, 141.2, 140.7, 139.1 (q, J=41.0 Hz), 132.6 (q, J=32.9 Hz), 124.7 (q, J=272.0 Hz), 123.3, 121.2, 120.7, 119.5, 119.1, 116.9, 115.3; $^{19}$F NMR (376 MHz, CDCl$_3$) δ −63.10 (s, 12 F), −64.52 (s, 3 F); HRMS (ESI$^+$): Calcd for C$_{22}$H$_{10}$ F$_{11}$N$_6{}^+$[M+H]$^+$: 643.0722, Observed: 643.0747.

N$^5$,N$^6$-bis(2-fluoro-3-(trifluoromethyl)phenyl)-2-(trifluoromethyl)-1H-imidazo[4,5-b]pyrazine-5,6-diamine (12e). Synthesized by general procedure F. 40%, as a yellow solid. $^1$H NMR (500 MHz, Acetone-d$_6$) δ 8.24 (t, 2H, J=8.0 Hz), 8.22 (brs, 2H), 7.45 (m, 4H); $^{13}$C NMR (125 MHz, Acetone-d$_6$) δ 151.2 (d, J=256.4 Hz), 147.1, 140.8, 138.6 (q, J=39.6 Hz), 130.24 (d, J=10. Hz), 127.0, 124.5, 123.0 (q, J=271.4 Hz), 119.2 (q, J=268.9 Hz), 120.2, 118.0 (d, J=10.8 Hz), 117.8 (q, J=10.8 Hz); $^{19}$F NMR (376 MHz, Acetone-d$_6$) δ −60.42 (s, 3 F), −60.46 (s, 3 F), −63.6 (s, 3 F), −128.35 (s, 2 F); HRMS (ESI$^+$): Calcd for C$_{20}$H$_{10}$ F$_{11}$N$_6{}^+$ [M+H]$^+$: 543.0786, Observed: 543.0768.

N$^5$,N$^6$-bis(3-fluoro-4-(trifluoromethoxy)phenyl)-2-(trifluoromethyl)-1H-imidazo[4,5-b]pyrazine-5,6-diamine (12f). Synthesized by general procedure F. 33%) as a yellow solid. $^1$H NMR (500 MHz, Acetone-d$_6$) δ 12.93 (brs, 1H), 8.43 (m, 2H), 7.84 (s, 1H), 7.81 (m, 1H), 7.35 (d, 2H, J=8.7 Hz), 7.29 (t, 2H, 8.7); $^{13}$C NMR (125 MHz, CDCl$_3$) δ 154.3 (d, J=247.2 Hz), 141.7, 140.4, 139.8, 139.4, 137.2 (q, J=41.1 Hz), 129.8 (d, J=13.8 Hz), 124.0, 123.8, 120.7 (q, J=256.3 Hz), 119.18 (q, J=268.9 Hz), 115.2, 107.3 (d, J=23.6 Hz); $^{19}$F NMR (376 MHz, Acetone-d$_6$) δ−54.89 (d, 6 F, J=5.1 Hz), −59.56 (s, 3 F), −124.65 (s, 2 F); HRMS (ESI$^+$): Calcd for C$_{20}$H$_{10}$ F$_{11}$N$_6$O$_2{}^+$ [M+H]$^+$: 575.0684, Observed: 575.0671.

N$^5$,N$^6$-bis(2-fluoro-4-(trifluoromethyl)phenyl)-2-(trifluoromethyl)-1H-imidazo[4,5-b]pyrazine-5,6-diamine (12g). Synthesized by general procedure F. 53%, as a yellow solid. $^1$H NMR (500 MHz, CDCl$_3$) δ 9.91 (brs, 1H), 8.24 (m, 1H), 8.15 (m, 1H), 7.45 (m, 4H), 6.94 (brs, 1H), 6.73 (brs, 1H); $^{13}$C NMR (125 MHz, CDCl$_3$) δ 152.3 (d, J=245.4 Hz), 152.0 (d, J=245.4 Hz), 140.6, 139.8, 139.4, 138.9 (q, J=42.3 Hz), 132.1, 131.7 (d, J=10.8 Hz), 131.0 (d, J=10.8 Hz), 123.6 (q, J=271.1 Hz), 122.0 (q, J=4.6 Hz), 121.8 (q, J=4.6 Hz), 120.5, 120.0, 118.2 (q, J=270.6 Hz), 113.1 (q, J=3.6 Hz), 112.9 (q, J=3.6 Hz), 112.7 (q, J=3.6 Hz), 112.5 (q, J=3.6 Hz); $^{19}$F NMR (376 MHz, CDCl$_3$) δ −62.02 (s, 3 F), −62.12 (s, 3 F), −64.62 (s, 3 F), −128.52 (m, 1 F), −130.33 (m, 1 F); HRMS (ESI$^+$): Calcd for C$_{20}$H$_{10}$ F$_{11}$N$_6{}^+$ [M+H]$^+$: 543.0786, Observed: 543.0810.

N$^5$,N$^6$-bis(3-fluoro-4-(trifluoromethyl)phenyl)-2-(trifluoromethyl)-1H-imidazo[4,5-b]pyrazine-5,6-diamine (12h). Synthesized by general procedure F. 56%, as a yellow solid. $^1$H NMR (500 MHz, Acetone-d$_6$) δ 13.06 (brs, 1H), 8.82 (brs, 2H), 7.91 (d, 2H, J=13.9 Hz), 7.63 (t, 2H, J=8.7 Hz), 7.51 (dd, 2H, J=8.7, 2.0 Hz); $^{19}$F NMR (376 MHz, Acetone-d$_6$) δ−64.89 (s, 3 F), −60.70 (d, 3 F, J=12.1 Hz), −115.56 (m, 2 F); HRMS (ESI$^+$): Calcd for C$_{20}$H$_{10}$ F$_{11}$N$_6{}^+$[M+H]$^+$: 543.0786, Observed: 543.0807.

N$^5$,N$^6$-bis(3,5-difluorophenyl)-2-(trifluoromethyl)-1H-imidazo[4,5-b]pyrazine-5,6-diamine (12i). Synthesized by general procedure F. 40%, as a yellow solid. $^1$H NMR (500 MHz, CDCl$_3$) (10.71 (brs, 1H), 7.16 (s, 1H), 7.04 (s, 2H), 6.82 (s, 1H), 6.73 (s, 2H), 6.51 (s, 1H), 6.38 (s, 1H); $^{13}$C NMR (125 MHz, CDCl$_3$) δ 163.4 (d, J=246.8 Hz), 163.3 (d, J=246.8 Hz), 142.7, 141.8, 141.4, 138.9, 138.4 (q, J=42.2 Hz), 138.3, 132.5, 118.3 (q, J=270.6 Hz), 102.5 (d, J=28.3 Hz), 101.4 (d, J=28.3 Hz), 98.7 (d, J=29.7 Hz), 98.3 (d, J=32.6 Hz), 97.8 (d, J=29.7 Hz); $^{19}$F NMR (376 MHz, CDCl$_3$) δ−64.45 (s, 3 F), −108.85 (m, 2 F), −108.94 (m, 2 F); HRMS (ESI$^+$): Calcd for C$_8$H$_{10}$ F$_7$N$_6{}^+$ [M+H]$^+$: 443.0850, Observed: 443.0884.

N$^5$,N$^6$-bis(2,3-difluorophenyl)-2-(trifluoromethyl)-1H-imidazo[4,5-b]pyrazine-5,6-diamine (12j). Synthesized by general procedure F. 47%, as a yellow solid. $^1$H NMR (500 MHz, Acetone-d$_6$) δ 12.96 (brs, 1H), 8.11 (brs, 2H), 7.68 (t, 2H, J=7.4 Hz), 7.19 (m, 2H), 7.06 (q, 2H, J=8.4 Hz); $^{19}$F NMR (376 MHz, Acetone-d$_6$) δ−64.80 (s, 3 F), −140.55 (m, 2 F), −149.44 (m, 1 F), −151.89 (m, 1 F); HRMS (ESI$^+$): Calcd for C$_8$H$_{10}$ F$_7$N$_6{}^+$[M+H]$^+$: 443.0850, Observed: 443.0848.

N$^5$,N$^6$-di-p-tolyl-2-(trifluoromethyl)-1H-imidazo[4,5-b]pyrazine-5,6-diamine (12k). Synthesized by general procedure F. 19%, as a yellow solid. $^1$H NMR (500 MHz, Acetone-d$_6$) δ 12.73 (brs, 1H), 8.09 (brs, 1H), 7.87 (brs, 1H), 7.59 (d, 4H, J=8.0 Hz), 7.15 (d, 4H, J=8.0 Hz), 2.31 (s, 6H); $^{19}$F NMR (376 MHz, Acetone-d$_6$) δ−64.36 (s, 3 F); HRMS (ESI$^+$): Calcd for C$_{20}$H$_{18}$ F$_3$N$_6{}^+$[M+H]$^+$: 399.1540, Observed: 399.1549.

N$^5$,N$^6$-diphenyl-2-(trifluoromethyl)-1H-imidazo[4,5-b]pyrazine-5,6-diamine (12l). Synthesized by general procedure F. 18%, as a yellow solid. $^1$H NMR (500 MHz, Acetone-d$_6$) δ 12.81 (brs, 1H), 8.18 (brs, 1H), 7.96 (brs, 1H), 7.71 (d, 4H, J=8.0 Hz), 7.34 (t, 4H, J=8.0 Hz), 7.03 (brs, 2H); $^{19}$F NMR (376 MHz, Acetone-d$_6$) δ−64.47 (s, 3 F); HRMS (ESI$^+$): Calcd for C$_8$H$_4$ F$_3$N$_6$$^+$[M+H]$^+$: 371.1227, Observed: 371.1226.

N$^5$,N$^6$-bis(4-(trifluoromethoxy)phenyl)-2-(trifluoromethyl)-1H-imidazo[4,5-b]pyrazine-5,6-diamine (12m). Synthesized by general procedure F. 23%, as a yellow solid. $^1$H NMR (500 MHz, Acetone-d$_6$) δ 12.93 (brs, 1H), 8.31 (brs, 2H), 7.82 (d, 4H, J=8.3 Hz), 7.31 (d, 4H, J=8.3 Hz); $^{19}$F NMR (376 MHz, Acetone-d$_6$) δ−58.93 (s, 6 F), −64.61 (s, 3 F); HRMS (ESI$^+$): Calcd for C$_{20}$H$_{12}$ F$_9$N$_6$O$_2$$^+$[M+H]$^+$: 539.0873, Observed: 539.0864.

N$^5$,N$^6$-bis(4-methoxyphenyl)-2-(trifluoromethyl)-1H-imidazo[4,5-b]pyrazine-5,6-diamine (12n). Synthesized by general procedure F. 8%, as a yellow solid. $^1$H NMR (500 MHz, Acetone-d$_6$) δ 12.68 (brs, 1H), 8.31 (brs, 2H), 7.62 (d, 4H, J=8.7 Hz), 6.93 (d, 4H, J=8.7 Hz), 3.80 (s, 6H); $^{19}$F NMR (376 MHz, Acetone-d$_6$) δ−64.27 (s, 3 F); HRMS (ESI$^+$): Calcd for C$_{20}$H$_{18}$ F$_3$N$_6$O$_2$$^+$[M+H]$^+$: 431.1438, Observed: 431.1419.

N$^5$-(2-fluorophenyl)-N$^6$-(3-fluorophenyl)-2-(trifluoromethyl)-1H-imidazo[4,5-b]pyrazine-5,6-diamine (12o). Synthesized by general procedure F. 43%, as a yellow solid. $^1$H NMR (500 MHz, Acetone-d$_6$) δ 12.89 (brs, 1H), 8.43 (brs, 2H), 7.83 (m, 1H), 7.80 (dt, 1H, J=12.0, 2.3 Hz), 7.45 (dd, 1H, J=8.2, 2.0, 0.9 Hz), 7.34 (td, 1H, J=8.2, 6.7 Hz), 7.22 (dd, 1H, J=9.3, 4.8 Hz), 7.14 (m, 2H), 6.78 (td, 1H, J=8.5, 2.6 Hz); $^{19}$F NMR (376 MHz, Acetone-d$_6$) δ−64.65 (s, 3 F), −126.34 (s, 1 F), −114.08 (s, 1 F); HRMS (ESI$^+$): Calcd for C$_{18}$H$_{12}$ F$_5$N$_6$$^+$ [M+H]$^+$: 407.1038, Observed: 407.1020.

N$^5$-(2-fluorophenyl)-N$^6$-(4-(trifluoromethoxy)phenyl)-2-(trifluoromethyl)-1H-imidazo[4,5-b]pyrazine-5,6-diamine (12p). Synthesized by general procedure F. 36%, as a yellow solid. $^1$H NMR (500 MHz, Acetone-d$_6$) δ 12.91 (brs, 1H), 8.42 (brs, 1H), 7.89 (m, 1H), 7.86 (d, 2H, J=8.9 Hz), 7.78 (brs, 1H), 7.31 (d, 2H, J=8.9 Hz), 7.20 (m, 2H), 7.14 (m, 1H); $^{19}$F NMR (376 MHz, Acetone-d$_6$) δ−58.91 (s, 3 F), −64.65 (s, 3 F), −126.38 (s, 1 F); HRMS (ESI$^+$): Calcd for C$_{19}$H$_{12}$ F$_7$N$_6$O$^+$[M+H]$^+$: 473.0955, Observed: 473.0935.

N$^5$-(2-fluorophenyl)-N$^6$-(3,5-bis(trifluoromethyl)phenyl)-2-(trifluoromethyl)-1H-imidazo[4,5-b]pyrazine-5,6-diamine (12q). Synthesized by general procedure F. 33%, as a yellow solid. $^1$H NMR (500 MHz, Acetone-d$_6$) δ 13.10 (brs, 1H), 8.84 (brs, 1H), 8.47 (s, 2H), 8.05 (m, 1H), 7.82 (brs, 1H), 7.61 (s, 1H), 7.21 (m, 3H); $^{19}$F NMR (376 MHz, Acetone-d$_6$) δ−63.52 (s, 6 F), −64.77 (s, 3 F), −125.13 (s, 0.5 F), −127.11 (s, 0.5 F); HRMS (ESI$^+$): Calcd for C$_{20}$H$_{11}$ F$_{10}$N$_6$$^+$ [M+H]$^+$: 525.0880, Observed: 525.0841.

N$^5$-(2-fluorophenyl)-N$^6$-(4-methoxyphenyl)-2-(trifluoromethyl)-1H-imidazo[4,5-b]pyrazine-5,6-diamine (12r). Synthesized by general procedure F. 27%, as a yellow solid. $^1$H NMR (500 MHz, Acetone-d$_6$) δ 12.78 (brs, 1H), 8.24 (brs, 1H), 8.03 (brs, 1H), 7.90 (brs, 1H), 7.64 (d, 2H, J=8.9 Hz), 7.21 (m, 1H), 7.19 (m, 1H), 7.12 (m, 1H), 6.94 (d, 2H, J=8.9 Hz), 3.80 (s, 3H); $^{19}$F NMR (376 MHz, Acetone-d$_6$) δ−64.49 (s, 3 F), −125.93 (s, 0.5 F), −127.84 (s, 0.5 F); HRMS (ESI$^+$): Calcd for C$_{19}$H$_{15}$ F$_4$N$_6$O$^+$[M+H]$^+$: 419.1228, Observed: 419.1229.

N$^5$-(2-fluorophenyl)-N$^6$-phenyl-2-(trifluoromethyl)-1H-imidazo[4,5-b]pyrazine-5,6-diamine (12s). Synthesized by general procedure F. 33%, as a yellow solid. $^1$H NMR (500 MHz, Acetone-d$_6$) δ 12.87 (brs, 1H), 8.27 (brs, 1H), 7.88 (brs, 1H), 7.74 (d, 2H, J=7.9 Hz), 7.34 (t, 2H, J=7.9 Hz), 7.20 (m, 2H), 7.13 (m, 1H), 7.04 (t, 1H, J=7.9 Hz); $^{19}$F NMR (376 MHz, Acetone-d$_6$) δ−64.57 (s, 3 F), −125.68 (s, 0.5 F), −127.59 (s, 0.5 F); HRMS (ESI$^+$): Calcd for C$_{18}$H$_{13}$ F$_4$N$_6$$^+$[M+H]$^+$: 389.1157, Observed: 389.1132.

N$^5$-(2-fluorophenyl)-N$^6$-(2-fluoro-3-(trifluoromethyl)phenyl)-2-(trifluoromethyl)-1H-imidazo[4,5-b]pyrazine-5,6-diamine (12t). Synthesized by general procedure F. 38%, as a yellow solid. $^1$H NMR (500 MHz, Acetone-d$_6$) δ 12.97 (brs, 1H), 8.24 (t, 1H, J=7.3 Hz), 8.11 (brs, 1H), 7.41 (m, 2H), 7.21 (m, 2H), 7.16 (t, 1H, J=7.9 Hz); $^{19}$F NMR (376 MHz, Acetone-d$_6$) δ−61.69 (d, 3 F, J=12.9 Hz), −64.78 (s, 3 F), −125.88 (s, 0.5 F), −127.72 (s, 0.5 F), −128.62 (s, 0.5 F), −130.78 (s, 0.5 F); HRMS (ESI$^+$): Calcd for C$_{19}$H$_{11}$ F$_8$N$_6$$^+$ [M+H]$^+$: 475.0912, Observed: 475.0891.

N$^5$-(2-fluorophenyl)-N$^6$-(p-tolyl)-2-(trifluoromethyl)-1H-imidazo[4,5-b]pyrazine-5,6-diamine (12u). Synthesized by general procedure F. 31%, as a yellow solid. $^1$H NMR (500 MHz, Acetone-d$_6$) δ 12.82 (brs, 1H), 8.16 (brs, 1H), 7.88 (t, 1H, J=7.3 Hz), 7.71 (brs, 1H), 7.63 (d, 2H, J=8.3 Hz), 7.20 (m, 2H), 7.16 (d, 2H, J=8.3 Hz), 7.12 (m, 1H), 2.31 (s, 3H); $^{19}$F NMR (376 MHz, Acetone-d$_6$) δ−64.52 (s, 3 F), −125.91 (s, 0.5 F), −127.60 (s, 0.5 F); HRMS (ESI$^+$): Calcd for C$_{19}$H$_{15}$ F$_4$N$_6$$^+$[M+H]$^+$: 403.1289, Observed: 403.1308.

N$^5$-(2-fluorophenyl)-N$^6$-cyclohexyl-2-(trifluoromethyl)-1H-imidazo[4,5-b]pyrazine-5,6-diamine (12v). Synthesized by general procedure F. It is a mixture of two compounds, with the ratio of isomer 1:isomer 2=3:2.5%, as a yellow solid. Isomer 1: $^1$H NMR (500 MHz, CDCl$_3$) δ 9.84 (brs, 1H), 8.00 (t, 1H, J=8.4 Hz), 7.11 (m, 2H), 6.96 (m, 1H), 6.19 (brs, 1H), 4.59 (d, 1H, J=6.5 Hz), 3.89 (m, 1H), 2.12 (m, 2H), 1.72 (m, 2H), 1.45 (m, 2H), 1.26 (m, 4H); $^{19}$F NMR (376 MHz, CDCl$_3$) δ−64.09 (s, 3 F), −132.43 (s, 1 F); Isomer 2: $^1$H NMR (500 MHz, CDCl$_3$) δ 9.84 (brs, 1H), 7.92 (t, 1H, J=8.4 Hz), 7.11 (m, 2H), 7.04 (m, 1H), 6.42 (brs, 1H), 4.20 (d, 1H, J=6.5 Hz), 4.05 (m, 1H), 2.20 (m, 2H), 1.72 (m, 2H), 1.45 (m, 2H), 1.26 (m, 4H); $^{19}$F NMR (376 MHz, CDCl$_3$) δ−64.22 (s, 3 F), −130.37 (s, 1 F); HRMS (ESI$^+$): Calcd for C$_{18}$H$_{19}$ F$_4$N$_6$$^+$[M+H]$^+$: 395.1602, Observed: 395.1613.

N$^5$-(2-fluorophenyl)-N$^6$-propyl-2-(trifluoromethyl)-1H-imidazo[4,5-b]pyrazine-5,6-diamine (12w). Synthesized by general procedure F. It is a mixture of two compounds, with the ratio of isomer 1:isomer 2=5:3.7%, as a yellow solid. Isomer 1: $^1$H NMR (500 MHz, CDCl$_3$) δ 10.25 (brs, 1H), 7.99 (brs, 1H), 7.08 (m, 2H), 6.97 (m, 1H), 6.37 (brs, 1H), 4.94 (brs, 1H), 3.46 (brs, 2H), 1.74 (q, 2H, J=7.2 Hz), 1.02 (t, 3H, J=7.2 Hz); $^{19}$F NMR (376 MHz, CDCl$_3$) δ−63.99 (s, 3 F), −131.80 (s, 1 F); Isomer 2: $^1$H NMR (500 MHz, CDCl$_3$) δ 10.25 (brs, 1H), 7.99 (brs, 1H), 7.08 (m, 2H), 6.97 (m, 1H), 6.61 (brs, 1H), 4.58 (brs, 1H), 3.08 (brs, 2H), 1.74 (q, 2H, J=7.2 Hz), 1.02 (t, 3H, J=7.2 Hz); $^{19}$F NMR (376 MHz, CDCl$_3$) δ−63.99 (s, 3 F), −129.90 (s, 1 F); HRMS (ESI$^+$): Calcd for C$_{15}$H$_{15}$ F$_4$N$_6$$^+$[M+H]$^+$: 355.1289, Observed: 355.1323.

N$^5$-(2-fluorophenyl)-N$^6$-3,3,3-trifluoropropyl-2-(trifluoromethyl)-1H-imidazo[4,5-b]pyrazine-5,6-diamine (12x). Synthesized by general procedure F. 17%, as a yellow solid. $^1$H NMR (500 MHz, Acetone-d$_6$) δ 12.80 (brs, 1H), 7.95 (t, 1H, J=7.7 Hz), 7.40 (brs, 1H), 7.18 (m, 2H), 7.10 (m, 1H), 6.66 (brs, 1H), 3.82 (td, 2H, J=7.2, 5.6 Hz), 2.72 (qt, 2H, J=11.3, 7.2 Hz); $^{19}$F NMR (376 MHz, Acetone-d$_6$) δ−64.35 (s, 3 F), −65.77 (t, 3 F, J=11.3 Hz), −127.03 (s, 0.5 F), −128.50 (s, 0.5 F); HRMS (ESI$^+$): Calcd for C$_{15}$H$_{12}$ F$_7$N$_6$$^+$ [M+H]$^+$: 409.1006, Observed: 409.0981.

N$^5$,N$^6$-bis(2-fluorophenyl)-1-methyl-2-(trifluoromethyl)-imidazo[4,5-b]pyrazine-5,6-diamine (13a). Synthesized by general procedure G. 60%, as a yellow solid. $^1$H NMR (500 MHz, CDCl$_3$) δ 8.09 (t, 1H, J=8.3 Hz), 8.09 (t, 1H, J=8.3 Hz), 7.21-6.98 (m, 6H), 6.87 (s, 1H), 6.52 (s, 1H), 3.95 (s, 3H); $^{13}$C NMR (125 MHz, CDCl$_3$) δ 153.4 (d, J=242.0 Hz), 153.2 (d, J=242.0 Hz), 141.4, 140.6, 138.2 (q, J=39.7 Hz), 137.7, 133.7, 128.7 (d, J=10.4 Hz), 128.0 (d, J=10.4 Hz), 124.7 (d, J=3.6 Hz), 124.5 (d, J=3.6 Hz), 123.7 (d, J=7.5 Hz); 123.1 (d, J=7.5 Hz), 121.0, 120.8, 119.1 (q, J=270.6 Hz), 115.5 (d, J=19.3 Hz), 115.1 (d, J=19.3 Hz), 29.9; $^{19}$F NMR (376 MHz, CDCl$_3$) δ −62.88 (s, 3 F), −130.22 (m, 1 F), −131.80 (m, 1 F); HRMS (ESI$^+$): Calcd for C$_{19}$H$_{14}$F$_5$N$_6^+$ [M+H]$^+$: 421.1195, Observed: 421.1198.

N$^5$,N$^6$-bis(2-fluoro-5-(trifluoromethyl)phenyl)-1-methyl-2-(trifluoromethyl)-imidazo[4,5-b]pyrazine-5,6-diamine (13b). Synthesized by general procedure G. 66%, as a yellow solid. $^1$H NMR (500 MHz, CDCl$_3$) δ 8.09 (t, 1H, J=8.3 Hz), 8.09 (t, 1H, J=8.3 Hz), 7.21-6.98 (m, 6H), 6.87 (s, 1H), 6.52 (s, 1H), 3.95 (s, 3H); $^{13}$C NMR (125 MHz, CDCl$_3$) δ 154.8 (d, J=248.2 Hz), 154.6 (d, J=248.2 Hz), 141.2, 140.6, 139.5 (q, J=40.0 Hz), 139.3, 138.1, 134.3, 129.6 (d, J=11.4 Hz), 128.5 (d, J=11.4 Hz), 127.5 (q, J=32.9 Hz), 127.4 (q, J=32.9 Hz), 123.8 (q, J=272.1 Hz), 123.7 (q, J=272.1 Hz); 120.6 (dq, J=8.0, 3.4 Hz), 120.4 (dq, J=8.0, 3.4 Hz), 118.9 (q, J=270.9 Hz), 118.2 (q, J=3.8 Hz), 117.7 (q, J=3.8 Hz), 115.9 (d, J=20.7 Hz), 115.8 (d, J=20.7 Hz), 29.9; $^{19}$F NMR (376 MHz, CDCl$_3$) δ −62.00 (s, 3 F), −62.34 (s, 3 F), −63.03 (s, 3 F), −125.82 (m, 1 F), −125.89 (m, 1 F); HRMS (ESI$^+$): Calcd for C$_{21}$H$_{12}$F$_{11}$N$_6^+$ [M+H]$^+$: 557.0942, Observed: 557.0925.

N$^5$,N$^6$-bis(2-(trifluoromethyl)phenyl)-1-methyl-2-(trifluoromethyl)-imidazo[4,5-b]pyrazine-5,6-diamine (13c). Synthesized by general procedure G. 79%, as a yellow solid. $^1$H NMR (500 MHz, CDCl$_3$) δ 7.89 (d, 1H, J=8.3 Hz), 7.78 (d, 1H, J=8.3 Hz), 7.66 (d, 1H, J=7.9 Hz), 7.62 (d, 1H, J=7.8 Hz), 7.53 (t, 1H, J=7.8 Hz), 7.46 (t, 1H, J=7.8 Hz), 7.19 (t, 1H, J=7.6 Hz), 7.12 (t, 1H, J=7.6 Hz), 7.07 (s, 1H), 6.76 (s, 1H), 3.95 (s, 3H); $^{13}$C NMR (125 MHz, CDCl$_3$) δ 141.8, 140.6, 139.3 (q, J=40.0 Hz), 138.8, 138.7, 137.8, 134.5, 133.1, 132.8, 126.8 (q, J=5.4 Hz), 126.7 (q, J=5.4 Hz), 124.5 (q, J=272.9 Hz), 124.2 (q, J=272.9 Hz), 123.4, 122.6, 121.6, 120.7, 120.0 (q, J=30.2 Hz); 119.1 (q, J=30.5 Hz), 119.0 (q, J=270.9 Hz), 29.9; $^{19}$F NMR (376 MHz, CDCl$_3$) δ−61.47 (s, 6 F), −63.04 (s, 3 F); HRMS (ESI$^+$): Calcd for C$_{21}$H$_{14}$F$_9$N$_6^+$[M+H]$^+$: 521.1131, Observed: 521.1139.

N$^5$,N$^6$-bis(3,5-bis(trifluoromethyl)phenyl)-1-methyl-2-(trifluoromethyl)-imidazo[4,5-b]pyrazine-5,6-diamine (13d). Synthesized by general procedure G. 76%, as a yellow solid. $^1$H NMR (500 MHz, CDCl$_3$) δ 8.08 (s, 2H), 7.71 (s, 2H), 7.61 (s, 1H), 7.52 (s, 1H), 7.29 (s, 1H), 6.70 (s, 1H), 3.97 (s, 3H); $^{13}$C NMR (125 MHz, CDCl$_3$) δ 141.9, 140.8, 140.6, 138.8 (q, J=40.0 Hz), 138.7, 137.7, 137.6, 133.9, 132.6 (d, J=8.1 Hz), 132.3 (d, J=8.1 Hz), 123.2 (q, J=272.7 Hz), 123.1 (q, J=272.7 Hz), 118.7 (q, J=271.4 Hz), 119.2, 118.1, 116.4, 115.9, 29.7; $^{19}$F NMR (376 MHz, CDCl$_3$) δ−63.19 (s, 6 F), −63.06 (s, 6 F), −63.03 (s, 3 F); HRMS (ESI$^+$): Calcd for C$_{23}$H$_{12}$F$_{15}$N$_6^+$ [M+H]$^+$: 657.0878, Observed: 657.0906.

N$^5$,N$^6$-bis(2-fluoro-3-(trifluoromethyl)phenyl)-1-methyl-2-(trifluoromethyl)-imidazo[4,5-b]pyrazine-5,6-diamine (13e). Synthesized by general procedure G. 64%, as a yellow solid. $^1$H NMR (500 MHz, CDCl$_3$) δ 8.31 (d, 1H, J=7.5 Hz), 8.20 (d, 1H, J=7.5 Hz), 7.36 (t, 1H, J=6.9 Hz), 7.30 (m, 1H), 7.27 (m, 1H), 7.22 (t, 1H, J=8.0 Hz), 6.92 (d, 1H, J=3.9 Hz), 6.67 (d, 1H, J=3.9 Hz), 3.95 (s, 3H); $^{13}$C NMR (125 MHz, CDCl$_3$) δ 150.6 (dq, J=249.6, 5.0 Hz), 149.86 (dq, J=249.6, 5.0), 140.6, 140.0, 139.2 (q, J=39.6 Hz), 138.1, 133.8, 129.6 (d, J=9.3 Hz), 129.0 (d, J=9.3 Hz), 124.4, 124.3 (d, J=4.7 Hz), 124.2 (d, J=4.7 Hz), 122.5 (q, J=272.3 Hz), 122.4 (q, J=272.2 Hz), 120.6 (q, J=4.6 Hz), 119.8 (q, J=4.6 Hz), 119.0 (d, J=10.8 Hz); 118.8 (q, J=271.0 Hz), 118.7 (q, J=10.8 Hz), 118.5 (q, J=10.8 Hz), 118.3 (q, J=10.8 Hz), 29.7; $^{19}$F NMR (376 MHz, CDCl$_3$) δ−61.29 (d, 3 F, J=12.9 Hz), 61.21 (d, 3 F, J=12.9 Hz), −63.05 (s, 3 F), −131.62 (m, 1 F), −134.31 (m, 1 F); HRMS (ESI$^+$): Calcd for C$_{21}$H$_{12}$F$_{11}$N$_6^+$ [M+H]$^+$: 557.0942, Observed: 557.0934.

N$^5$,N$^6$-bis(3-fluoro-4-(trifluoromethoxy)phenyl)-1-methyl-2-(trifluoromethyl)-imidazo[4,5-b]pyrazine-5,6-diamine (13f). Synthesized by general procedure G. 80%, as a yellow solid. $^1$H NMR (500 MHz, CDCl$_3$) δ 7.64 (dd, 1H, J=12.0, 2.4 Hz), 7.32 (d, 1H, J=11.0 Hz), 7.28 (d, 1H, J=9.4 Hz), 7.20 (t, 1H, J=8.5 Hz), 7.10 (d, 1H, J=9.0 Hz), 6.98 (d, 1H, J=9.3 Hz), 6.93 (s, 1H), 6.46 (s, 1H), 3.98 (s, 3H); $^{13}$C NMR (125 MHz, CDCl$_3$) δ 154.9 (d, J=251.8 Hz), 154.8 (d, J=251.8), 141.2, 140.6, 139.6, 139.4, 138.5 (q, J=40.3 Hz), 137.9, 136.6, 134.2, 131.7 (d, J=32.7 Hz), 131.2 (d, J=32.7 Hz), 124.4, 122.6 (q, J=257.2 Hz); 118.8 (q, J=270.7 Hz), 114.8, 114.1, 108.1 (q, J=23.4 Hz), 107.5 (d, J=23.4 Hz), 29.7; $^{19}$F NMR (376 MHz, Acetone-d$_6$) δ−56.16 (d, 3 F, J=5.1 Hz), −59.23 (d, 3 F, J=5.1 Hz), −63.03 (s, 3 F), −126.11 (s, 1 F), −126.26 (s, 1 F); HRMS (ESI$^+$): Calcd for C$_{21}$H$_{12}$F$_{11}$N$_6$O$_2^+$ [M+H]$^+$: 589.0841, Observed: 589.0798.

N$^5$,N$^6$-bis(2-fluoro-4-(trifluoromethyl)phenyl)-1-methyl-2-(trifluoromethyl)-imidazo[4,5-b]pyrazine-5,6-diamine (13g). Synthesized by general procedure G. 37%, as a yellow solid. $^1$H NMR (500 MHz, Acetone-d$_6$) δ 8.44 (t, 1H, J=8.2 Hz), 8.38 (brs, 1H), 8.17 (t, 1H, J=8.2 Hz), 7.59 (m, 4H), 4.00 (s, 3H); $^{19}$F NMR (376 MHz, Acetone-d$_6$) δ−62.27 (s, 3 F), −62.39 (s, 3 F), −63.48 (s, 3 F), −125.74 (s, 1 F), −126.69 (s, 1 F); HRMS (ESI$^+$): Calcd for C$_{21}$H$_{12}$F$_{11}$N$_6^+$ [M+H]$^+$: 557.0942, Observed: 557.0951.

N$^5$,N$^6$-bis(3-fluoro-4-(trifluoromethyl)phenyl)-1-methyl-2-(trifluoromethyl)-imidazo[4,5-b]pyrazine-5,6-diamine (13h). Synthesized by general procedure G. 39%, as a yellow solid. $^1$H NMR (500 MHz, Acetone-d$_6$) δ 8.99 (brs, 1H), 8.71 (brs, 1H), 7.98 (dd, 1H, J=13.9, 1.8 Hz), 7.85 (dd, 1H, J=13.9, 1.8 Hz), 7.67 (m, 3H), 7.52 (dd, 1H, J=8.6, 1.8 Hz), 4.06 (s, 3H); $^{19}$F NMR (376 MHz, Acetone-d$_6$) δ−60.64 (d, 6 F, J=12.1 Hz), −63.08 (s, 3 F), −112.07 (s, 1 F), −112.19 (s, 1 F); HRMS (ESI$^+$): Calcd for C$_{21}$H$_{12}$F$_{11}$N$_6^+$ [M+H]$^+$: 557.0942, Observed: 557.0953.

N$^5$,N$^6$-bis(3,5-difluorophenyl)-1-methyl-2-(trifluoromethyl)-imidazo[4,5-b]pyrazine-5,6-diamine (13i). Synthesized by general procedure G. 36%, as a yellow solid. $^1$H NMR (500 MHz, Acetone-d$_6$) δ 8.92 (brs, 1H), 8.64 (brs, 1H), 7.54 (m, 2H), 7.43 (m, 2H), 6.67 (tt, 1H, J=9.2, 2.3 Hz), 6.60 (tt, 1H, J=9.2, 2.3 Hz), 4.03 (s, 3H); $^{19}$F NMR (376 MHz, Acetone-d$_6$) δ−63.25 (s, 3 F), −111.66 (t, 2 F, J=9.5 Hz), −111.30 (t, 2 F, J=9.5 Hz); HRMS (ESI$^+$): Calcd for C$_{19}$H$_{12}$F$_7$N$_6^+$[M+H]$^+$: 457.1006, Observed: 457.1005.

N$^5$,N$^6$-bis(2,3-difluorophenyl)-1-methyl-2-(trifluoromethyl)-imidazo[4,5-b]pyrazine-5,6-diamine (13j). Synthesized by general procedure G. 47%, as a yellow solid. $^1$H NMR (500 MHz, CDCl$_3$) δ 7.74 (dt, 2H, J=15.5, 7.1 Hz), 7.11 (q, 1H, J=8.2 Hz), 7.03 (q, 1H, J=8.2 Hz), 6.93 (q, 1H, J=8.2 Hz), 6.85 (q, 1H, J=8.2 Hz), 6.88 (brs, 1H), 6.55 (brs, 1H), 3.95 (s, 3H); $^{19}$F NMR (376 MHz, CDCl$_3$) δ−63.01 (s, 3 F), −137.37 (m, 1 F), −138.10 (m, 1 F), −153.69 (m, 1 F), −155.70 (m, 1 F); HRMS (ESI$^+$): Calcd for C$_{19}$H$_{12}$F$_7$N$_6^+$ [M+H]$^+$: 457.1006, Observed: 457.1032.

1-Methyl-N$^5$,N$^6$-di-p-tolyl-2-(trifluoromethyl)-imidazo[4,5-b]pyrazine-5,6-diamine (13k). Synthesized by general procedure G. 32%, as a yellow solid. $^1$H NMR (500 MHz, Acetone-d$_6$) δ 8.20 (brs, 1H), 7.86 (brs, 1H), 7.69 (d, 1H, J=8.4 Hz), 7.60 (d, 1H, J=8.4 Hz), 7.19 (d, 1H, J=8.4 Hz), 7.14 (d, 1H, J=8.4 Hz), 3.94 (s, 3H) 2.32 (s, 3H), 2.30 (s, 3H); $^{19}$F NMR (376 MHz, Acetone-d$_6$) δ−62.84 (s, 3 F); HRMS (ESI$^+$): Calcd for C$_{21}$H$_{20}$F$_3$N$_6^+$[M+H]$^+$: 413.1696, Observed: 413.1723.

1-Methyl-$N^5$,$N^6$-di-phenyl-2-(trifluoromethyl)-imidazo[4,5-b]pyrazine-5,6-diamine (13l). Synthesized by general procedure G. 42%, as a yellow solid. $^1$H NMR (500 MHz, Acetone-$d_6$) δ 8.29 (brs, 1H), 7.96 (brs, 1H), 7.82 (d, 2H, J=7.8 Hz), 7.82 (d, 2H, J=7.8 Hz), 7.38 (t, 2H, J=7.8 Hz), 7.33 (t, 2H, J=7.8 Hz), 7.07 (t, 1H, J=7.8 Hz), 7.01 (t, 1H, J=7.8 Hz), 3.96 (s, 3H); $^{19}$F NMR (376 MHz, Acetone-$d_6$) δ−62.93 (s, 3 F); HRMS (ESI$^+$): Calcd for $C_{19}H_{16}F_3N_6^+$ [M+H]$^+$: 385.1383, Observed: 385.1419.

1-Methyl-$N^5$,$N^6$-bis(4-(trifluoromethoxy)phenyl)-2-(trifluoromethyl)-imidazo[4,5-b]pyrazine-5,6-diamine (13m). Synthesized by general procedure G. 32%, as a yellow solid. $^1$H NMR (500 MHz, Acetone-$d_6$) δ 8.55 (brs, 1H), 8.22 (brs, 1H), 7.96 (d, 2H, J=9.1 Hz), 7.81 (d, 2H, J=9.1 Hz), 7.35 (d, 2H, J=8.5 Hz), 7.31 (d, 2H, J=8.5 Hz), 3.99 (s, 3H); $^{19}$F NMR (376 MHz, Acetone-$d_6$) δ−58.89 (s, 6 F), −63.09 (s, 3 F); HRMS (ESI$^+$): Calcd for $C_{21}H_{14}F_9N_6O_2^+$[M+H]$^+$: 553.1029, Observed: 553.1051.

1-Methyl-$N^5$,$N^6$-bis(4-methoxyphenyl)-2-(trifluoromethyl)-imidazo[4,5-b]pyrazine-5,6-diamine (13n). Synthesized by general procedure G. 37%, as a yellow solid. $^1$H NMR (500 MHz, Acetone-$d_6$) δ 8.18 (brs, 1H), 7.84 (brs, 1H), 7.74 (d, 2H, J=9.0 Hz), 7.64 (d, 2H, J=9.0 Hz), 6.96 (d, 2H, J=9.0 Hz), 6.92 (d, 2H, J=9.0 Hz), 3.92 (s, 3H), 3.81 (s, 3H), 3.79 (s, 3H); $^{19}$F NMR (376 MHz, Acetone-$d_6$) δ−62.74 (s, 3 F); HRMS (ESI$^+$): Calcd for $C_{21}H_{20}F_3N_6O_2^+$[M+H]$^+$: 445.1594, Observed: 445.1597.

1-Methyl-$N^5$-(2-fluorophenyl)-$N^6$-(3-fluorophenyl)-2-(trifluoromethyl)-imidazo[4,5-b]pyrazine-5,6-diamine (13o). Synthesized by general procedure G. It is a mixture of two compounds, with the ratio of isomer 1:isomer 2=4:3.38%, as a yellow solid. Isomer 1: $^1$H NMR (500 MHz, Acetone-$d_6$) δ 8.32 (brs, 1H), 8.02 (td, 1H, J=8.4, 1.7 Hz), 7.99 (brs, 1H), 7.74 (dt, 1H, J=12.0, 2.3 Hz), 7.44 (ddd, 1H, J=8.2, 2.1, 0.9 Hz), 7.34 (dt, 1H, J=8.2, 6.7 Hz), 7.25 (m, 2H), 7.18 (m, 1H), 6.76 (td, 1H, J=8.9, 2.8 Hz), 3.90 (s, 3H); $^{19}$F NMR (376 MHz, Acetone-$d_6$) δ−63.13 (s, 3 F), −114.12 (s, 1 F), −126.43 (s, 1 F); Isomer 2: $^1$H NMR (500 MHz, Acetone-$d_6$) δ 8.62 (brs, 1H), 7.64 (brs, 1H), 7.84 (m, 2H), 7.58 (ddd, 1H, J=8.2, 2.1, 0.9 Hz), 7.39 (dt, 1H, J=8.2, 6.7 Hz), 7.25 (m, 1H), 7.18 (m, 1H), 7.10 (m, 1H), 6.83 (td, 1H, J=8.4, 2.6 Hz), 4.01 (s, 3H); $^{19}$F NMR (376 MHz, Acetone-$d_6$) δ−63.13 (s, 3 F), −113.81 (s, 1 F), −127.16 (s, 1 F); HRMS (ESI$^+$): Calcd for $C_{19}H_{14}F_5N_6^+$ [M+H]$^+$: 421.1195, Observed: 421.1217.

1-Methyl-$N^5$-(2-fluorophenyl)-$N^6$-(4-(trifluoromethoxy)phenyl)-2-(trifluoromethyl)-imidazo[4,5-b]pyrazine-5,6-diamine (13p). Synthesized by general procedure G. It is a mixture of two compounds, with the ratio of isomer 1:isomer 2=1:1.42%, as a yellow solid. Isomer 1: $^1$H NMR (500 MHz, Acetone-$d_6$) δ 8.35 (brs, 1H), 8.02 (brs, 1H), 8.04 (t, 1H, J=7.4 Hz), 8.00 (d, 2H, J=8.9 Hz), 7.35 (d, 2H, J=8.9 Hz), 7.25 (m, 1H), 7.19 (m, 1H), 7.11 (m, 2H), 3.90 (s, 3H); $^{19}$F NMR (376 MHz, Acetone-$d_6$) δ−58.91 (s, 3 F), −63.14 (s, 3 F), −127.18 (s, 1 F); Isomer 2: $^1$H NMR (500 MHz, Acetone-$d_6$) δ 8.67 (brs, 1H), 8.22 (t, 1H, J=7.4 Hz), 7.67 (brs, 1H), 7.85 (d, 2H, J=8.9 Hz), 7.31 (d, 2H, J=8.9 Hz), 7.25 (m, 1H), 7.19 (m, 1H), 7.11 (m, 2H), 3.99 (s, 3H); $^{19}$F NMR (376 MHz, Acetone-$d_6$) δ−58.87 (s, 3 F), −63.12 (s, 3 F), −126.44 (s, 1 F); HRMS (ESI$^+$): Calcd for $C_{19}H_{12}F_7N_6O^+$[M+H]$^+$: 487.1112, Observed: 487.1130.

1-Methyl-$N^5$-(2-fluorophenyl)-$N^6$-(3,5-bis(trifluoromethyl)phenyl)-2-(trifluoromethyl)-imidazo[4,5-b]pyrazine-5,6-diamine (13q). Synthesized by general procedure G. It is a mixture of two compounds, with the ratio of isomer 1:isomer 2=4:3.38%, as a yellow solid. Isomer 1: $^1$H NMR (500 MHz, Acetone-$d_6$) δ 8.79 (brs, 1H), 8.43 (s, 2H), 8.15 (m, 1H), 7.99 (t, 1H, J=8.9 Hz), 7.60 (s, 1H), 7.25 (m, 2H), 7.19 (m, 1H), 3.92 (s, 3H); $^{19}$F NMR (376 MHz, Acetone-$d_6$) δ−63.26 (s, 3 F), −63.53 (s, 6 F), −125.91 (s, 1 F); Isomer 2: $^1$H NMR (500 MHz, Acetone-$d_6$) δ 9.09 (brs, 1H), 8.57 (s, 2H), 7.82 (t, 1H, J=8.9 Hz), 7.78 (s, 1H), 7.67 (s, 1H), 7.25 (m, 1H), 7.19 (m, 1H), 7.12 (m, 1H), 4.02 (s, 3H); $^{19}$F NMR (376 MHz, Acetone-$d_6$) δ−63.25 (s, 3 F), −63.63 (s, 6 F), −126.89 (s, 1 F); HRMS (ESI$^+$): Calcd for $C_{21}H_{13}F_{10}N_6^+$[M+H]$^+$: 539.1037, Observed: 539.1029.

1-Methyl-$N^5$-(2-fluorophenyl)-$N^6$-(4-methoxyphenyl)-2-(trifluoromethyl)-imidazo[4,5-b]pyrazine-5,6-diamine (13r). Synthesized by general procedure G. It is a mixture of two compounds, with the ratio of isomer 1:isomer 2=1:0.65. 32%, as a yellow solid. Isomer 1: $^1$H NMR (500 MHz, Acetone-$d_6$) δ 8.06 (t, 1H, J=8.2 Hz), 8.02 (brs, 1H), 7.92 (brs, 1H), 7.64 (d, 2H, J=8.9 Hz), 7.24 (m, 2H), 7.16 (m, 1H), 6.93 (d, 2H, J=8.9 Hz), 3.89 (s, 3H), 3.80 (s, 3H); $^{19}$F NMR (376 MHz, Acetone-$d_6$) δ−62.97 (s, 3 F), −126.77 (s, 1 F); Isomer 2: $^1$H NMR (500 MHz, Acetone-$d_6$) δ 8.37 (brs, 1H), 7.58 (brs, 1H), 7.87 (t, 1H, J=8.2 Hz), 7.76 (d, 2H, J=8.9 Hz), 7.24 (m, 1H), 7.16 (m, 1H), 7.10 (m, 1H), 6.97 (d, 2H, J=8.9 Hz), 3.94 (s, 3H), 3.81 (s, 3H); $^{19}$F NMR (376 MHz, Acetone-$d_6$) δ−62.97 (s, 3 F), −127.41 (s, 1 F); HRMS (ESI$^+$): Calcd for $C_{20}H_7F_4N_6O^+$[M+H]$^+$: 433.1394, Observed: 433.1397.

1-Methyl-$N^5$-(2-fluorophenyl)-$N^6$-phenyl-2-(trifluoromethyl)-imidazo[4,5-b]pyrazine-5,6-diamine (13s). Synthesized by general procedure G. It is a mixture of two compounds, with the ratio of isomer 1:isomer 2=1:2.28%, as a yellow solid. Isomer 1:$^1$H NMR (500 MHz, Acetone-$d_6$) δ 8.13 (brs, 1H), 8.06 (t, 2H, J=7.9 Hz), 7.99 (brs, 1H), 7.72 (d, 2H, J=7.9 Hz), 7.33 (t, 1H, J=7.9 Hz), 7.20 (m, 3H), 7.02 (t, 1H, J=7.9 Hz), 3.90 (s, 3H); $^{19}$F NMR (376 MHz, Acetone-$d_6$) δ−63.07 (s, 3 F), −126.60 (s, 1 F); Isomer 2:1H NMR (500 MHz, Acetone-$d_6$) δ 8.46 (brs, 1H), 7.85 (d, 2H, J=7.9 Hz), 7.65 (brs, 1H), 7.34 (t, 2H, J=7.9 Hz), 7.38 (t, 1H, J=7.9 Hz), 7.20 (m, 2H), 7.11 (m, 1H), 7.08 (t, 1H, J=7.9 Hz), 3.98 (s, 3H); $^{19}$F NMR (376 MHz, Acetone-$d_6$) δ−63.06 (s, 3 F), −127.20 (s, 1 F); HRMS (ESI$^+$): Calcd for $C_{19}H_{15}F_4N_6^+$[M+H]$^+$: 403.1289, Observed: 403.1272.

1-Methyl-$N^5$-(2-fluorophenyl)-$N^6$-(2-fluoro-3-(trifluoromethyl)phenyl)-2-(trifluoromethyl)-imidazo[4,5-b]pyrazine-5,6-diamine (13t). Synthesized by general procedure G. It is a mixture of two compounds, with the ratio of isomer 1:isomer 2=2:3.67%, as a yellow solid. Isomer 1: $^1$H NMR (500 MHz, Acetone-$d_6$) δ 8.22 (brs, 1H), 8.19 (m, 1H), 8.13 (t, 1H, J=7.3 Hz), 8.05 (brs, 1H), 7.44 (m, 2H), 7.21 (m, 3H), 3.93 (s, 3H); $^{19}$F NMR (376 MHz, Acetone-$d_6$) δ−61.69 (d, 3 F, J=12.9 Hz), −63.29 (s, 3 F), −126.69 (s, 1 F), −130.45 (s, 1 F); Isomer 2: $^1$H NMR (500 MHz, Acetone-$d_6$) δ 8.39 (brs, 1H), 8.37 (m, 1H), 7.94 (t, 1H, J=7.3 Hz), 7.86 (brs, 1H), 7.44 (m, 2H), 7.21 (m, 2H), 7.11 (m, 1H), 3.93 (s, 3H); $^{19}$F NMR (376 MHz, Acetone-$d_6$) δ−61.81 (d, 3 F, J=12.9 Hz), −63.27 (s, 3 F), −127.38 (s, 1 F), −128.35 (s, 1 F); HRMS (ESI$^+$): Calcd for $C_{20}H_{13}F_8N_6^+$[M+H]$^+$: 489.1068, Observed: 489.1056.

1-Methyl-$N^5$-(2-fluorophenyl)-$N^6$-(p-tolyl)-2-(trifluoromethyl)-imidazo[4,5-b]pyrazine-5,6-diamine (13u). Synthesized by general procedure G. It is a mixture of two compounds, with the ratio of isomer 1:isomer 2=0.9:1. 43%, as a yellow solid. Isomer 1: $^1$H NMR (500 MHz, Acetone-$d_6$) δ 8.06 (t, 1H, J=7.4 Hz), 8.05 (brs, 1H), 7.62 (d, 2H, J=8.3 Hz), 7.62 (brs, 1H), 7.24 (m, 1H), 7.17 (m, 4H), 3.89 (s, 3H), 2.30 (s, 3H); $^{19}$F NMR (376 MHz, Acetone-$d_6$) δ−57.82 (s, 3 F), −121.44 (s, 1 F); Isomer 2: $^1$H NMR (500 MHz, Acetone-$d_6$) δ 8.40 (brs, 1H), 7.86 (t, 1H, J=7.4 Hz), 7.73 (d, 2H, J=8.3 Hz), 7.62 (brs, 1H), 7.24 (m, 1H), 7.17

(m, 3H), 7.09 (m, 1H), 3.96 (s, 3H), 2.32 (s, 3H); $^{19}$F NMR (376 MHz, Acetone-d$_6$) δ –57.82 (s, 3 F), –122.07 (s, 1 F); HRMS (ESI$^+$): Calcd for C$_{20}$H$_7$ F$_4$N$_6$$^+$[M+H]$^+$: 417.1445, Observed: 417.1435.

1-Methyl-N$^5$-(2-fluorophenyl)-N$^6$-cyclohexyl-2-(trifluoromethyl)-imidazo[4,5-b]pyrazine-5,6-diamine (13v). Synthesized by general procedure G. It is a mixture of two compounds, with the ratio of isomer 1:isomer 2=5:1. 29%, as a yellow solid. Isomer 1: $^1$H NMR (500 MHz, Acetone-d$_6$) δ 7.88 (td, 1H, J=8.1, 1.7 Hz), 7.33 (brs, 1H), 7.15 (m, 2H), 7.07 (m, 1H), 6.32 (d, 1H, J=6.0 Hz), 4.13 (m, 1H), 3.84 (s, 3H), 2.18 (m, 2H), 1.69 (m, 2H), 1.44 (m, 2H), 1.26 (m, 4H); $^{19}$F NMR (376 MHz, Acetone-d$_6$) δ –64.09 (s, 3 F), –132.43 (s, 1 F); Isomer 2: $^1$H NMR (500 MHz, Acetone-d$_6$) δ 8.03 (td, 1H, J=8.1, 1.7 Hz), 7.64 (brs, 1H), 7.15 (m, 3H), 5.90 (d, 1H, J=6.0 Hz), 4.69 (m, 1H), 3.93 (s, 3H), 1.81 (m, 2H), 1.69 (m, 2H), 1.44 (m, 2H), 1.26 (m, 4H); $^{19}$F NMR (376 MHz, Acetone-d$_6$) δ –64.22 (s, 3 F), –130.37 (s, 1 F); HRMS (ESI$^+$): Calcd for C$_{19}$H$_{21}$ F$_4$N$_6$$^+$[M+H]$^+$: 409.1758, Observed: 409.1740.

1-Methyl-N$^5$-(2-fluorophenyl)-N$^6$-propyl-2-(trifluoromethyl)-imidazo[4,5-b]pyrazine-5,6-diamine (13w). Synthesized by general procedure G. It is a mixture of two compounds, with the ratio of isomer 2=3:4. 32%, as a yellow solid. Isomer 1: $^1$H NMR (500 MHz, Acetone-d$_6$) δ 8.09 (td, 1H, J=8.1, 1.6 Hz), 7.31 (brs, 1H), 7.18 (m, 2H), 7.18 (m, 3H), 6.62 (brs, 1H), 3.93 (s, 1H), 3.57 (td, 2H, J=7.2, 5.3 Hz), 1.76 (m, 2H), 1.02 (t, 3H, J=7.2 Hz); $^{19}$F NMR (376 MHz, Acetone-d$_6$) δ –62.74 (s, 3 F), –128.21 (s, 1 F); Isomer 2: $^1$H NMR (500 MHz, CDCl$_3$) δ 7.95 (td, 1H, J=8.1, 1.6 Hz), 7.62 (brs, 1H), 6.97 (m, 1H), 6.18 (brs, 1H), 3.86 (s, 1H), 3.50 (td, 2H, J=7.2, 5.3 Hz), 1.76 (m, 2H), 1.01 (t, 3H, J=7.2 Hz); $^{19}$F NMR (376 MHz, Acetone-d$_6$) δ –62.74 (s, 3 F), –127.40 (s, 1 F); HRMS (ESI$^+$): Calcd for C$_{16}$H$_{17}$ F$_4$N$_6$$^+$[M+H]$^+$: 369.1445, Observed: 369.1451.

1-Methyl-N$^5$-(2-fluorophenyl)-N$^6$-3,3,3-trifluoropropyl-2-(trifluoromethyl)-imidazo[4,5-b]pyrazine-5,6-diamine (13x). Synthesized by general procedure G. It is a mixture of two compounds, with the ratio of isomer 1:isomer 2=3:4. 32%, as a yellow solid. Isomer 1: $^1$H NMR (500 MHz, Acetone-d$_6$) δ 8.11 (td, 1H, J=8.2, 1.7 Hz), 7.65 (brs, 1H), 7.18 (m, 3H), 6.52 (brs, 1H), 3.88 (s, 3H), 3.83 (td, 2H, J=7.1, 5.5 Hz), 2.72 (m, 2H); $^{19}$F NMR (376 MHz, Acetone-d$_6$) δ –62.82 (s, 3 F), –65.67 (t, 3 F, J=11.3), –127.57 (s, 1 F); Isomer 1: $^1$H NMR (500 MHz, Acetone-d$_6$) δ 7.97 (td, 1H, J=8.2, 1.7 Hz), 7.33 (brs, 1H), 7.18 (m, 2H), 7.07 (m, 2H), 6.94 (brs, 1H), 3.96 (s, 3H), 3.90 (td, 2H, J=7.1, 5.5 Hz), 2.72 (m, 2H); $^{19}$F NMR (376 MHz, Acetone-d$_6$) δ –62.85 (s, 3 F), –65.85 (t, 3 F, J=11.3), –128.46 (s, 1 F); HRMS (ESI$^+$): Calcd for C$_{16}$H$_{14}$ F$_7$N$_6$$^+$[M+H]$^+$: 423.1163, Observed: 423.1172.

Methyl 5,6-bis((2-fluorophenyl)amino)-2-(trifluoromethyl)-imidazo[4,5-b]pyrazine-1-carboxylate (14a). Synthesized by general procedure H. 54%, as a yellow solid. $^1$H NMR (500 MHz, CDCl$_3$) δ 8.48 (td, 1H, J=8.2, 1.7 Hz), 8.27 (s, 1H), 8.09 (s, 1H), 7.83 (td, 1H, J=8.2, 1.7 Hz), 7.22 (m, 6H), 4.14 (s, 3H); $^{19}$F NMR (376 MHz, CDCl$_3$) δ –63.04 (s, 3 F), –125.81 (m, 1 F), –127.85 (m, 1 F); HRMS (ESI$^+$): Calcd for C$_{20}$H$_{14}$ F$_8$N$_6$O$_2$$^+$ [M+H]$^+$: 465.1093, Observed: 465.1113.

Methyl 5,6-bis((2-fluoro-4-(trifluoromethyl)phenyl)amino)-2-(trifluoromethyl)-imidazo[4,5-b]pyrazine-1-carboxylate (14b). Synthesized by general procedure H. 64%, as a yellow solid. $^1$H NMR (500 MHz, CDCl$_3$) δ 8.59 (t, 2H, J=8.3 Hz), 8.17 (m, 2H), 7.51 (m, 2H), 7.22 (d, 1H, J=3.4 Hz), 6.73 (d, 1H, J=3.4 Hz), 4.20 (s, 3H); $^{19}$F NMR (376 MHz, CDCl$_3$) δ –62.11 (s, 3 F), –62.11 (s, 3 F), –62.83 (s, 3 F), –129.17 (m, 1 F), –129.56 (m, 1 F); HRMS (ESI$^+$): Calcd for C$_{22}$H$_{12}$ F$_{11}$N$_6$O$_2$$^+$ [M+H]$^+$: 601.0841, Observed: 601.0787.

Methyl 5,6-bis((3,5-difluorophenyl)amino)-2-(trifluoromethyl)-imidazo[4,5-b]pyrazine-1-carboxylate (14c). Synthesized by general procedure H. 71%, as a yellow solid. $^1$H NMR (500 MHz, CDCl$_3$) δ 7.51 (s, 1H), 7.37 (m, 2H), 6.92 (s, 1H), 6.82 (m, 2H), 6.56 (dt, 1H, J=8.8, 2.5 Hz), 6.43 (t, 1H, J=8.8 Hz), 4.25 (s, 3H); $^{19}$F NMR (376 MHz, CDCl$_3$) δ –62.79 (s, 3 F), –108.60 (t, 2 F, J=8.6 Hz), –109.0 (t, 2 F, J=8.6 Hz); HRMS (ESI$^+$): Calcd for C$_{20}$H$_{12}$ F$_7$N$_6$O$_2$$^+$ [M+H]$^+$: 501.0883, Observed: 501.0904.

N$^2$,N$^3$-bis(2-(trifluoromethyl)phenyl)pyrazine-2,3-diamine (16a). Synthesized by general procedure D. 11%, yellow oil. $^1$H NMR (400 MHz, Acetone-d$_6$) δ 8.28 (s, 2H), 7.87-7.82 (m, 4H), 7.82 (s, 2H), 7.65-7.60 (m, 4H). $^{19}$F NMR (376 MHz, Acetone-d$_6$) δ –61.52. (s 6 F); HRMS (ESI$^+$) m/z calcd for C$_8$H$_{13}$ F$_6$N$_4$ [M+H]$^+$: 399.1039, Found: 399.1036.

N$^2$,N$^3$-bis(3-(trifluoromethyl)phenyl)pyrazine-2,3-diamine (16b). Synthesized by general procedure D. 65%, yellow oil. $^1$H NMR (400 MHz, Acetone-d$_6$) δ 8.20 (s, 2H), 8.09-8.06 (m, 2H), 7.95-7.91 (m, 2H), 7.78 (s, 2H), 7.56-7.50 (m, 2H), 7.32-7.28 (m, 2H). $^{19}$F NMR (376 MHz, Acetone-d$_6$) δ –63.20 (s 6 F) HRMS (ESI$^+$) m/z calcd for C$_{18}$H$_{13}$ F$_6$N$_4$$^+$[M+H]$^+$: 399.1039, Found: 399.1044.

N$^2$,N$^3$-bis(4-(trifluoromethyl)phenyl)pyrazine-2,3-diamine (16c). Synthesized by general procedure D. 7%, yellow oil. $^1$H NMR (400 MHz, Acetone-d$_6$) δ 8.28 (s, 2H), 7.87-7.82 (m, 4H), 7.82 (s, 2H), 7.66-7.60 (m, 4H). $^{19}$F NMR (376 MHz, Acetone-d$_6$) δ –62.05. (s 6 F) HRMS (ESI$^+$) m/z calcd for C$_8$H$_{13}$ F$_6$N$_4$$^+$[M+H]$^+$: 399.1039, Found: 399.1037.

N$^2$,N$^3$-bis(3-methoxyphenyl)pyrazine-2,3-diamine (16d). Synthesized by general procedure D. 7%, yellow oil. $^1$H NMR (400 MHz, Acetone-d$_6$) δ 7.76 (s, 2H), 7.67 (s, 2H), 7.39-7.36 (m, 2H), 7.21-7.13 (m, 4H), 6.59-6.55 (m, 2H), 3.78 (s, 6H). HRMS (ESI$^+$) m/z calcd for C$_8$H$_{19}$N$_4$O$_2$$^+$[M+H]$^+$: 323.1503 Found: 323.1494.

N$^2$,N$^3$-bis(2-methoxyphenyl)pyrazine-2,3-diamine (16e). Synthesized by general procedure D. 20%, yellow oil. $^1$H NMR (400 MHz, Acetone-d$_6$) δ 8.10-8.05 (m, 2H), 7.69 (s, 2H), 7.39 (s, 2H), 7.05-6.89 (m, 6H), 3.89 (s, 6H). HRMS (ESI$^+$) m/z calcd for C$_{18}$H$_{19}$N$_4$O$_2$$^+$[M+H]$^+$: 323.1503 Found: 323.1517.

N$^2$,N$^3$-bis(3,5-bis(trifluoromethyl)phenyl)pyrazine-2,3-diamine (16f). Synthesized by general procedure D. 30%, yellow oil. $^1$H NMR (400 MHz, Acetone-d$_6$) δ 8.63 (s, 2H), 8.32 (s, 4H), 7.91 (s, 2H), 7.57 (s, 2H). $^{19}$F NMR (376 MHz, Acetone-d$_6$) δ –63.62. HRMS (ESI$^+$) m/z calcd for C$_{20}$H$_{11}$ F$_{12}$N$_4$$^+$[M+H]$^+$: 535.0787 Found: 535.0788.

N$^2$,N$^3$-bis(2-fluoro-5-(trifluoromethyl)phenyl)pyrazine-2,3-diamine (16g). Synthesized by general procedure D. 19%, yellow oil. $^1$H NMR (400 MHz, Acetone-d$_6$) δ 8.40-8.34 (m, 2H), 8.00 (s, 2H), 7.83 (s, 2H), 7.45-7.40 (m, 4H). HRMS (ESI$^+$) m/z calcd for C$_{18}$H$_{11}$ F$_8$N$_4$$^+$[M+H]$^+$: 435.0850 Found: 435.0849.

N$^2$,N$^3$-bis(2-fluoro-4-(trifluoromethyl)phenyl)pyrazine-2,3-diamine (16h). Synthesized by general procedure D. 15%, yellow oil. $^1$H NMR (400 MHz, Acetone-d$_6$) δ 8.19 (t, J=8.2 Hz, 2H), 8.08 (s, 2H), 7.88 (s, 2H), 7.58-7.48 (m, 4H). $^{19}$F NMR (376 MHz, Acetone-d$_6$) δ –62.31 (s, 2 F) –126.62 (s, 6 F). HRMS (ESI$^+$) m/z calcd for C$_{18}$H$_{11}$ F$_8$N$_4$$^+$[M+H]$^+$: 435.0840 Found: 435.0818.

N$^2$,N$^3$-bis(3-fluorophenyl)pyrazine-2,3-diamine (16i). Synthesized by general procedure D. 51%, yellow oil. $^1$H NMR (400 MHz, Acetone-d$_6$) δ 8.09-8.01 (m, 2H), 7.74 (s, 2H), 7.71-7.65 (m, 2H), 7.36-7.26 (m, 4H), 6.76-6.70 (m, 2H). $^{19}$F NMR (376 MHz, Acetone-$d_6$) δ −114.23. HRMS (ESI$^+$) m/z calcd for $C_6H_{13}F_2N_4^+$[M+H]$^+$: 299.1103 Found: 299.1109.

$N^2,N^3$-bis(2-(trifluoromethoxy)phenyl)pyrazine-2,3-diamine (16j). Synthesized by general procedure D. 6%, yellow oil. $^1$H NMR (400 MHz, Acetone-$d_6$) δ 7.99-7.95 (m, 2H), 7.78 (s, 2H), 7.72-7.65 (m, 2H), 7.40-7.31 (m, 4H), 7.17-7.11 (m, 2H). $^{19}$F NMR (376 MHz, Acetone-$d_6$) δ −58.45. HRMS (ESI$^+$) m/z calcd for $C_8H_{13}F_6N_4O_2^+$[M+H]$^+$: 431.0937 Found: 431.0938.

$N^2,N^3$-bis(3-(trifluoromethoxy)phenyl)pyrazine-2,3-diamine (16k). Synthesized by general procedure D. 8%, yellow oil. $^1$H NMR (400 MHz, Acetone-$d_6$) δ 8.16 (s, 2H), 7.83-7.79 (m, 2H), 7.76 (s, 2H), 7.61-7.57 (m, 2H), 7.40 (t, J=8.2 Hz, 2H), 6.95-6.90 (m, 2H). $^{19}$F NMR (376 MHz, Acetone-$d_6$) δ −58.33. HRMS (ESI$^+$) m/z calcd for $C_{18}H_{13}F_6N_4O_2^+$[M+H]$^+$: 431.0937 Found: 431.0955.

$N^2,N^3$-bis(2,3-difluorophenyl)pyrazine-2,3-diamine (16l). Synthesized by general procedure D. 39%, yellow oil. $^1$H NMR (400 MHz, Acetone-$d_6$) δ 7.85 (s, 2H), 7.74 (s, 2H), 7.69-7.63 (m, 2H), 7.19-7.10 (m, 2H), 7.05-6.95 (m, 2H). $^{19}$F NMR (376 MHz, Acetone-$d_6$) δ −140.64, −151.60. HRMS (ESI$^+$) m/z calcd for $C_6H_{11}F_4N_4^+$[M+H]$^+$: 335.0914 Found: 335.0913.

$N^2,N^3$-bis(2,4-difluorophenyl)pyrazine-2,3-diamine (16m). Synthesized by general procedure D. 30%, yellow oil. $^1$H NMR (400 MHz, Acetone-$d_6$) δ 7.91-7.82 (m, 2H), 7.61 (m, 4H), 7.13-7.06 (m, 2H), 7.04-6.96 (m, 2H). $^{19}$F NMR (376 MHz, Acetone-$d_6$) δ −118.40, −121.64. HRMS (ESI$^+$) m/z calcd for $C_6H_{11}F_4N_4^+$[M+H]$^+$: 335.0914 Found: 335.0923.

$N^2,N^3$-bis(4-(trifluoromethoxy)phenyl)pyrazine-2,3-diamine (16n). Synthesized by general procedure D. 24%, yellow oil. $^1$H NMR (400 MHz, Acetone-$d_6$) δ 8.03 (s, 2H), 7.79-7.73 (m, 4H), 7.70 (s, 2H), 7.30-7.24 (m, 4H). HRMS (ESI$^+$) m/z calcd for $C_8H_{13}F_6N_4O_2^+$[M+H]$^+$: 431.0937 Found: 431.0935.

Example 2. Biological Activity of Table 1 Compounds

Biological activities of the compounds synthesized is determined by determining increase in oxygen consumption rate (OCR).

Oxygen consumption rate (OCR) in whole cells is measured in general accordance with the method of Kenwood B M et al. (Mol. Met. (2014) 3:114-123).

OCR is measured using a Seahorse XF-24 Flux Analyzer (Seahorse Biosciences, North Billerica, MA). NMuLi, C2C12, and L6 cells are seeded in a Seahorse 24-well tissue culture plate at a density of $3.5\times10^4$ cells/well, isolated cardiomyocytes at a density of $4\times10^4$ cells/well, and human primary fibroblasts at a density of $1.1\times10^4$ cells/well. The cells are then allowed to adhere for 24 h. Prior to the assay, the media is changed to unbuffered DMEM containing pyruvate and glutamine (Gibco #12800-017. pH=7.4 at 37° C.) and the cells are equilibrated for 30 mins at 37° C. Compounds are injected during the assay and OCR is measured using 2 min measurement periods.

2-3 wells are used per condition and averaged over three plates (n=6-9). Statistical significance is determined by two-way ANOVA with Bonferroni's posttest.

The activity (increase in OCR) are presented in TABLE 2. Activities are reported as binned $EC_{50}$ values: A=5 μM or less; B=>5 to 20 μM; C=over 20 μM; 0=no effect.

TABLE 2

Increase in OCR of TABLE 1 Compounds

| Entry | Compound | $EC_{50}$ (μM) |
|---|---|---|
| 1 | 3a | C |
| 2 | 3b | A |
| 3 | 3c | B |
| 4 | 3d | 0 |
| 5 | 3e | C |
| 6 | 3f | 0 |
| 7 | 3g | 0 |
| 8 | 3h | B |
| 9 | 3i | 0 |
| 10 | 3j | 0 |
| 11 | 3k | A |
| 12 | 3l | A |
| 13 | 3m | A |
| 14 | 3n | A |
| 15 | 3o | 0 |
| 16 | 3p | 0 |
| 17 | 3q | A |
| 18 | 3r | A |
| 19 | 3s | A |
| 20 | 3t | A |
| 21 | 3u | 0 |
| 22 | 3v | 0 |
| 23 | 3w | A |
| 24 | 3x | A |
| 25 | 3y | A |
| 26 | 3z | C |
| 27 | 3aa | A |
| 28 | 3bb | A |
| 29 | 3cc | A |
| 30 | 3dd | 0 |
| 31 | 3ee | A |
| 32 | 4a | A |
| 33 | 4b | C |
| 34 | 4c | A |
| 35 | 4d | A |
| 36 | 4e | A |
| 37 | 4f | A |
| 38 | 4g | A |
| 39 | 4h | A |
| 40 | 4i | B |
| 41 | 4j | 0 |
| 42 | 4k | A |
| 43 | 4l | A |
| 44 | 4m | 0 |
| 45 | 4n | A |
| 46 | 4o | A |
| 47 | 4p | 0 |
| 48 | 4q | A |
| 49 | 4r | B |
| 50 | 4s | A |
| 51 | 4t | A |
| 52 | 4u | A |
| 53 | 4v | A |
| 54 | 4w | A |
| 55 | 4x | A |
| 56 | 4y | A |
| 57 | 4z | C |
| 58 | 4aa | A |
| 59 | 4bb | A |
| 60 | 6a | 0 |
| 61 | 6b | 0 |
| 62 | 7a | B |
| 63 | 7b | B |
| 64 | 7c | B |
| 65 | 7d | C |
| 66 | 7e | 0 |
| 67 | 7f | B |
| 68 | 7g | 0 |
| 69 | 7h | 0 |
| 70 | 10 | B |
| 71 | 11a | 0 |
| 72 | 11b | 0 |
| 73 | 11c | 0 |
| 74 | 12a | B |
| 75 | 12b | B |
| 76 | 12c | B |

TABLE 2-continued

Increase in OCR of TABLE 1 Compounds

| Entry | Compound | $EC_{50}$ (μM) |
|---|---|---|
| 77 | 12d | B |
| 78 | 12e | B |
| 79 | 12f | B |
| 80 | 12g | A |
| 81 | 12h | B |
| 82 | 12i | B |
| 83 | 12j | A |
| 84 | 12k | C |
| 85 | 12l | C |
| 86 | 12m | B |
| 87 | 12n | C |
| 88 | 12o | B |
| 89 | 12p | A |
| 90 | 12q | B |
| 91 | 12r | C |
| 92 | 12s | B |
| 93 | 12t | A |
| 94 | 12u | B |
| 95 | 12v | C |
| 96 | 12w | C |
| 97 | 12x | 0 |
| 98 | 13a | C |
| 99 | 13b | B |
| 100 | 13c | B |
| 101 | 13d | B |
| 102 | 13e | B |
| 103 | 13f | B |
| 104 | 13g | A |
| 105 | 13h | C |
| 106 | 13i | B |
| 107 | 13j | C |
| 108 | 13k | C |
| 109 | 13l | 0 |
| 110 | 13m | B |
| 111 | 13n | 0 |
| 112 | 13o | 0 |
| 113 | 13p | C |
| 114 | 13q | C |
| 115 | 13r | C |
| 116 | 13s | C |
| 117 | 13t | C |
| 118 | 13u | C |
| 119 | 13v | C |
| 120 | 13w | C |
| 121 | 13x | C |
| 122 | 14a | B |
| 123 | 14b | 0 |
| 124 | 14c | B |
| 125 | 16a | 0 |
| 126 | 16b | A |
| 127 | 16c | A |
| 128 | 16d | 0 |
| 129 | 16e | 0 |
| 130 | 16f | B |
| 131 | 16g | 0 |
| 132 | 16h | B |
| 133 | 16i | 0 |
| 134 | 16j | 0 |
| 135 | 16k | B |
| 136 | 16l | 0 |
| 137 | 16m | 0 |
| 138 | 16n | A |

Example 3. Diet Induced Obesity Mouse Study

Figure 2:
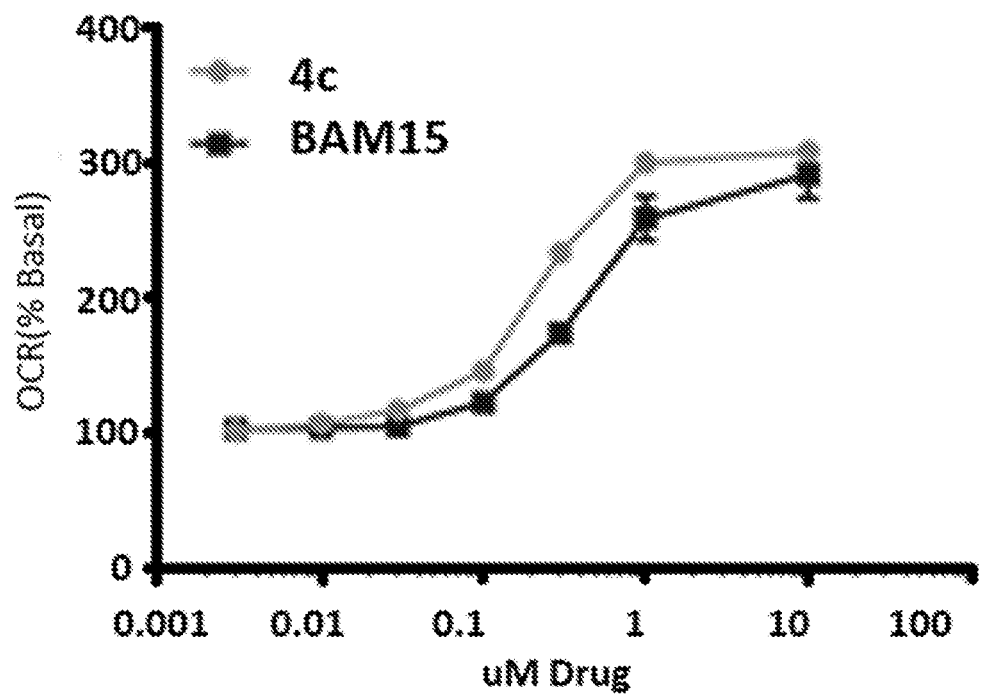
FIG. 2. Oxygen consumption rate as a function of drug dose plotted on a log scale. Compound 4c produces a consistently high oxygen consumption rate than the mitochondrial uncoupler BAM15.
Figure 3:
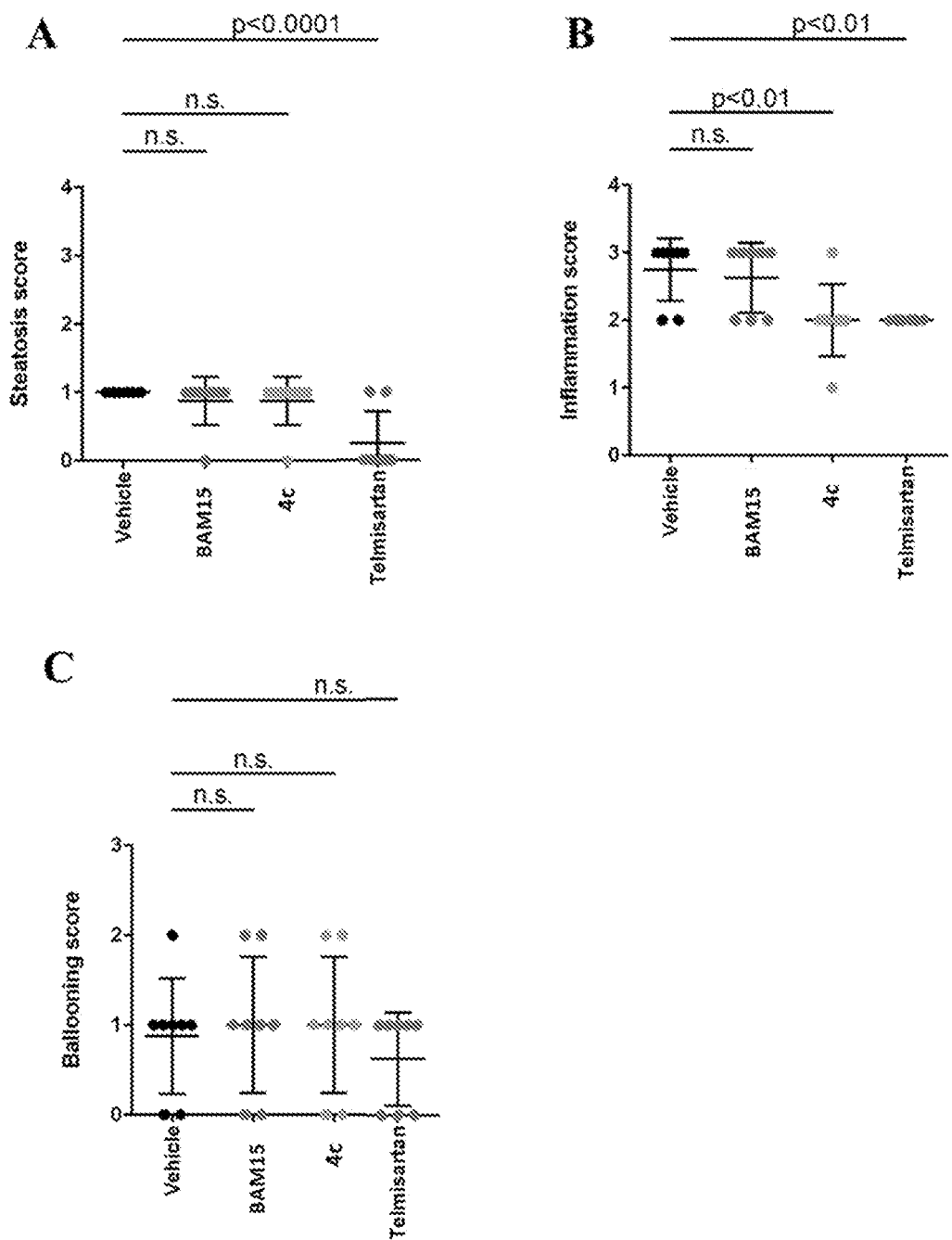
FIG. 3. Performance of compound 4c vs. BAM15 in assays that measure NALFD criteria.
Figure 4:
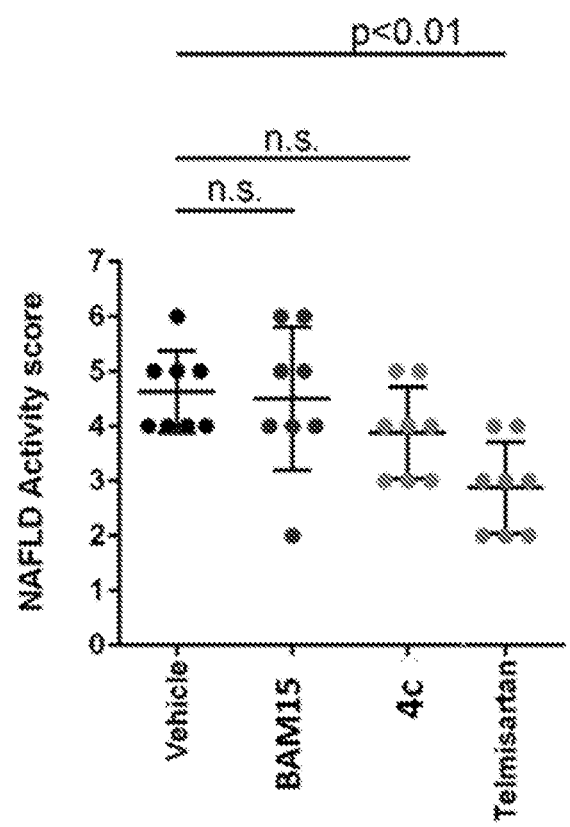
FIG. 4. Combined NALFD score based on the steatosis, inflammation and ballooning assays. Compound 4c produces as significantly lower NALFD score than BAM15.
Figure 5:
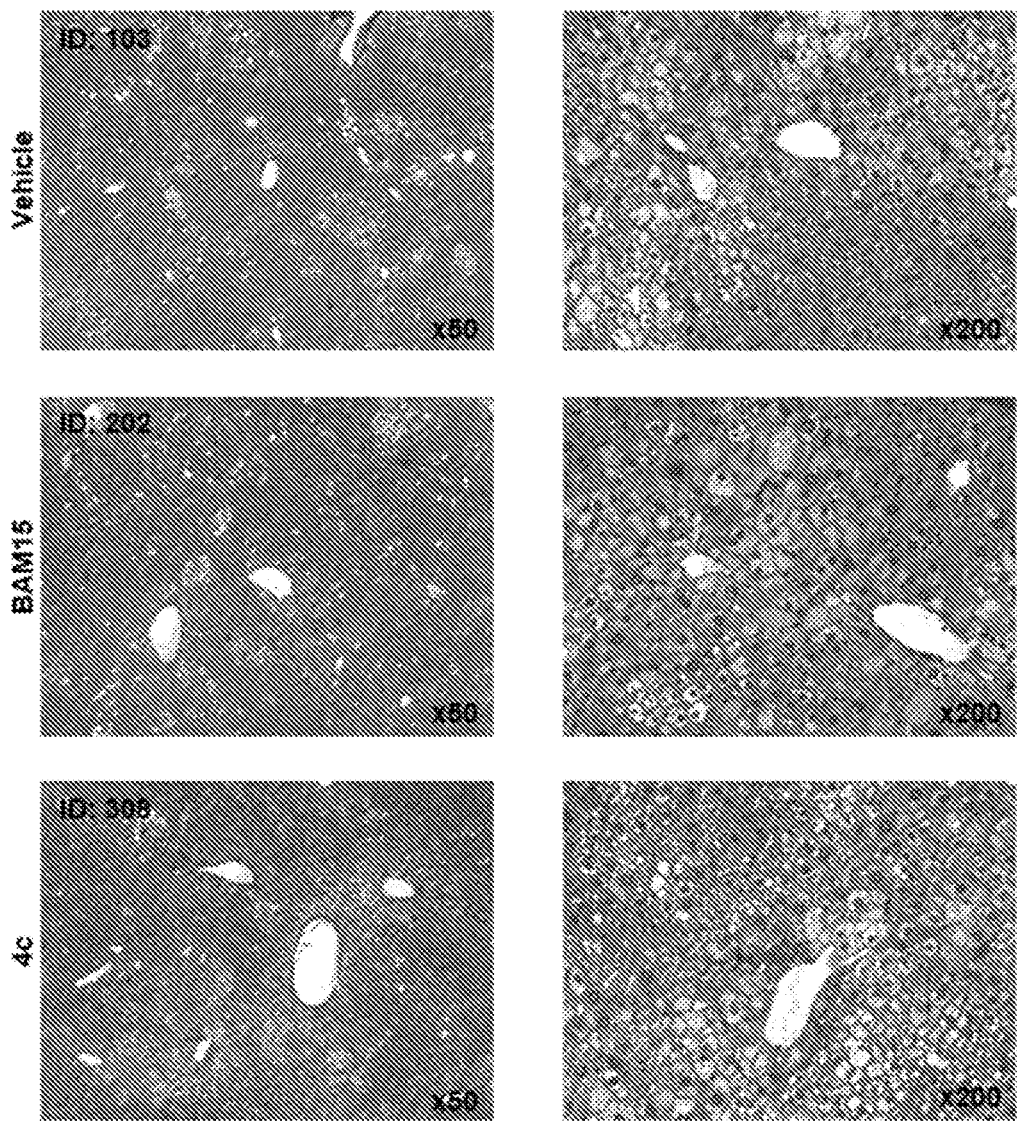
FIG. 5. Representative photomicrographs of HE-stained liver sections.
Figure 6:
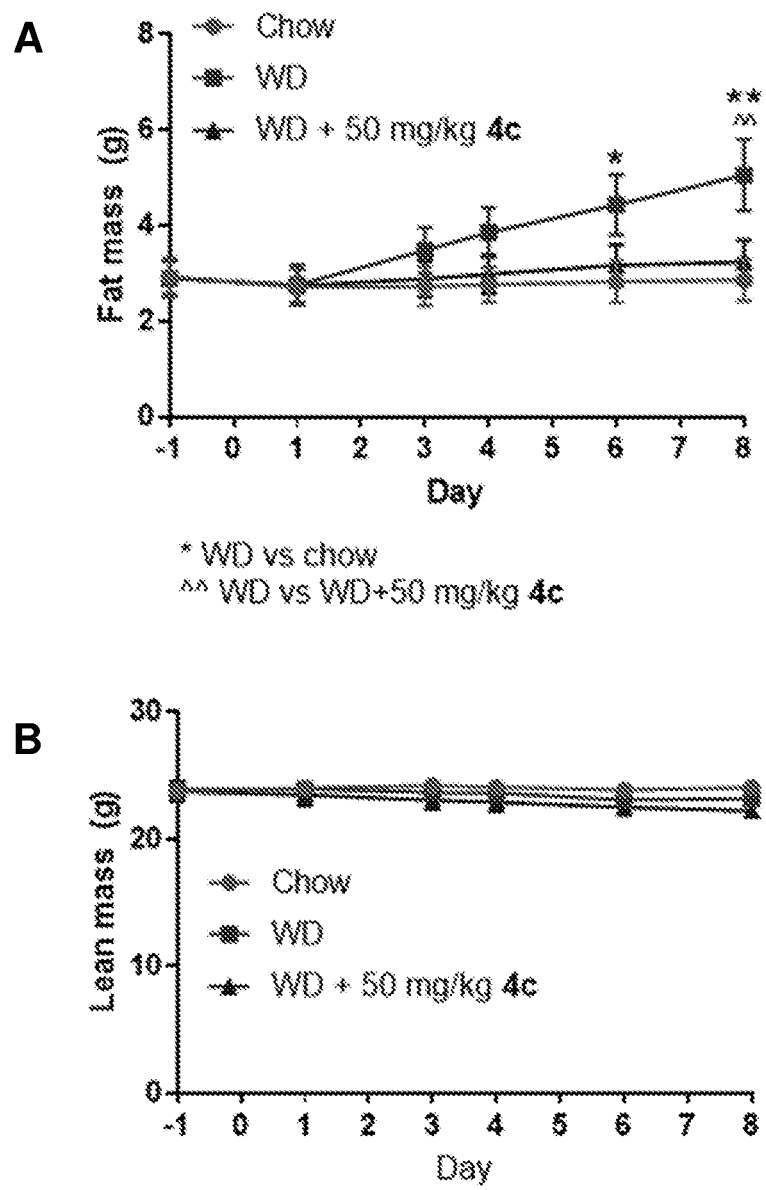
FIG. 6. Diet-induced Obesity Mouse Model. A. Mice administered compound 4c gained significantly less fat mass when fed a high fat Western Diet (WD) than mice fed the WD without compound 4c. B. All mice had substantially the same lean mass.
Figure 7:
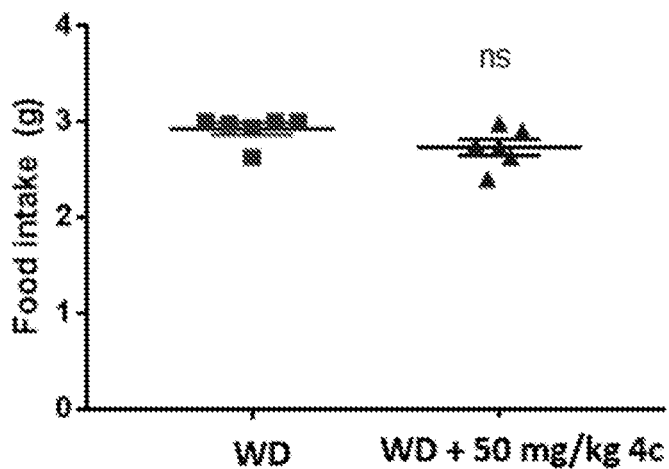
FIG. 7. Diet-induced Obesity Mouse Model. A. Comparison of food intake for mice given WD or WD+compound 4c. Both groups had similar food intake levels. B. Glucose tolerance test for mice given chow diet, high fat WD, or WD+50 mg/kg/day compound 4c. Mice administered compound 4c had significantly improved glucose tolerance compared to mice fed the high fat WD without compound 4c.
Figure 7:
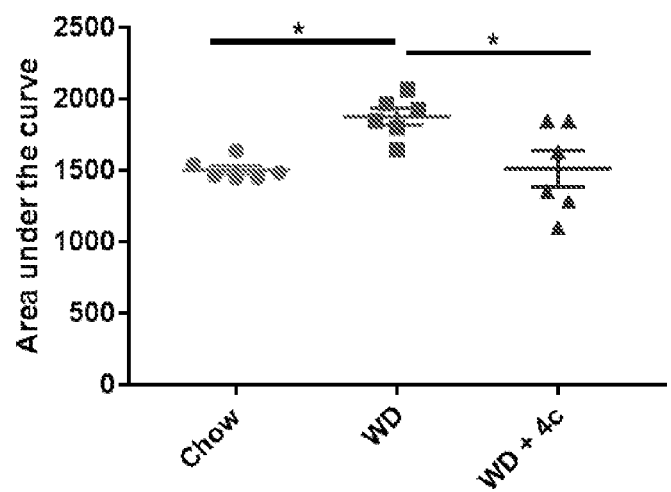

Male C57B/6J mice aged 3 months (n=6) are assigned to one of three treatment groups: normal chow diet (Chow), western diet (WD) or western diet containing compound 4c (WD+4c). Mice fed WD and WD 4c are individually housed and given 3 grams of fresh food daily. WD+4c contained a dose of 4c equivalent to 50 mg/kg/day. For all treatments pre-weighed food is placed in cages and food intake is calculated daily. Fat and lean mass are measured by EchoMRI. Oxygen consumption rate as a function of drug dose is shown in FIGS. 1 and 2. Fat and lean mass for mice given the high fat Western Diet or the Western Diet with the compound 4c was determined by Echo MRI and shown in FIG. 6. Mice receiving WD+4c gain less fat mass than W) control without losing lean mass and without a significant change in food intake (FIG. 7). FIG. 3 shows that compound 4c has anti-inflammatory effects in the STAM mouse model of fatty liver disease.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

Example 4. ROS Production Assay

Certain compounds of the disclosure also decrease ROS production, which can be measured in this assay. L6 myoblasts are seeded into black-walled clear-bottom 96-well microplates in L6 growth media and grown to confluence. Cells are then washed twice with PBS and co-incubated with 7.5 μM CM–$H_2$DCFDA and 0.5 ng/μL of each hit compound or vehicle control (DMSO) in KRP buffer (136 mM NaCl, 4.7 mM KCl, 10 mM $NaPO_4$, 0.9 mM $MgSO_4$, 0.9 mM $CaCl_2$, pH 7.4) supplemented with 25 mM D-glucose at 37° C. in 5% $CO_2$/95% air for 1 hr. 100 nM $H_2O_2$ is used as a positive control for ROS production. Following incubation, cells are washed three times with PBS to remove excess probe. Cells are then covered with 100 μL/well PBS and fluorescence intensity is measured by a Tecan Infinite® M200 microplate reader (Tecan Group Ltd, Switzerland) using a top-read configuration and with the excitation and emission filters set at 495±9 nm and 530±20 nm, respectively. Fluorescence data are recorded on Magellan (version 6.4) software and exported to Microsoft Excel for subsequent analysis. After subtracting the background fluorescence (that emitted from a well which does not receive the CM–$H_2$DCFDA probe) from each well, ROS production is expressed in terms of percentage fluorescence of the vehicle control for each condition. Compounds which increase ROS levels by greater than 20% are eliminated.

What is claimed is:

1. A compound or pharmaceutically acceptable salt thereof, wherein the compound is
   $N^5$-(2-fluorophenyl)-$N^6$-(pyridin-2-yl)-[1,2,5]oxadiazolo[3,4-b]pyrazine-5,6-diamine (4b);
   $N^5$-(2-fluorophenyl)-$N^6$-(3-fluorophenyl)-[1,2,]oxadiazolo[3,4-b]pyrazine-5,6-diamine (4c);
   $N^5$-(2,3-difluorophenyl)-$N^6$-(2-fluorophenyl)-[1,2,5]oxadiazolo[3,4-b]pyrazine-5,6-diamine (4e);
   $N^5$-(2,4-difluorophenyl)-$N^6$-(2-fluorophenyl)-[1,2,5]oxadiazolo[3,4-b]pyrazine-5,6-diamine (4f);
   $N^5$-(2-fluorophenyl)-$N^6$-(o-tolyl)[1,2,5]oxadiazolo[3,4-b]pyrazine-5,6-diamine (4g);
   $N^5$-(2-fluorophenyl)-$N^6$-(m-tolyl)[1,2,5]oxadiazolo[3,4-b]pyrazine-5,6-diamine (4h);
   $N^5$-(2-fluorophenyl)-$N^6$-(3-methoxyphenyl)-[1,2,5]oxadiazolo[3,4-b]pyrazine-5,6-diamine (4k);
   $N^5$-(2-fluorophenyl)-$N^6$-(4-methoxyphenyl)-[1,2,5]oxadiazolo[3,4-b]pyrazine-5,6-diamine (4l);

N⁵-(2-ethoxyphenyl)-N⁶-(2-fluorophenyl)-[1,2,5]oxadiazolo[3,4-b]pyrazine-5,6-diamine (4m);
N⁵-(3-ethoxyphenyl)-N⁶-(2-fluorophenyl)-[1,2,5]oxadiazolo[3,4-b]pyrazine-5,6-diamine (4n);
N⁵-(4-ethoxyphenyl)-N⁶-(2-fluorophenyl)-[1,2,5]oxadiazolo[3,4-b]pyrazine-5,6-diamine (4o);
3-((6-(2-fluorophenyl)amino)-[1,2,5]oxadiazolo[3,4-b]pyrazin-5-yl)amino)phenol (4p);
N⁵-(2-fluorophenyl)-N⁶-(2-(trifluoromethoxy)phenyl)-[1,2,5]oxadiazolo[3,4-b]pyrazine-5,6-diamine (4q);
N⁵-(2-fluorophenyl)-N⁶-(3-(trifluoromethoxy)phenyl)-[1,2,5]oxadiazolo[3,4-b]pyrazine-5,6-diamine (4r);
N⁵-(2-fluorophenyl)-N⁶-(4-(trifluoromethoxy)phenyl)-[1,2,5]oxadiazolo[3,4-b]pyrazine-5,6-diamine (4s);
2,2,2-Trifluoro-N-(4-((6-(2-fluorophenyl)amino)-[1,2,5]oxadiazolo[3,4-b]pyrazin-5-yl)amino)phenyl)acetamide (4t);
N⁵-(2-fluorophenyl)-N⁶-(2-(trifluoromethyl)phenyl)-[1,2,5]oxadiazolo[3,4-b]pyrazine-5,6-diamine (4u);
N⁵-(2-fluorophenyl)-N⁶-(3-(trifluoromethyl)phenyl)-[1,2,5]oxadiazolo[3,4-b]pyrazine-5,6-diamine (4v);
N⁵-(2-fluorophenyl)-N⁶-(4-(trifluoromethyl)phenyl)-[1,2,5]oxadiazolo[3,4-b]pyrazine-5,6-diamine (4w);
Methyl 4-((6-((2-fluorophenyl)amino)-[1,2,5]oxadiazolo[3,4-b]pyrazin-5-yl)amino)benzoate (4y);
4-Fluoro-3-((6-((2-fluorophenyl)amino)-[1,2,5]oxadiazolo[3,4-b]pyrazin-5-yl)amino)phenol (4z);
N⁵-(3,5-bis(trifluoromethyl)phenyl)-N⁶-(2-fluorophenyl)-[1,2,5]oxadiazolo[3,4-b]pyrazine-5,6-diamine (4aa);
N⁵-(2-fluoro-3-(trifluoromethyl)phenyl)-N⁶-(2-fluorophenyl)-[1,2,5]oxadiazolo[3,4-b]pyrazine-5,6-diamine (4bb);
N⁵-(2-fluorophenyl)-N⁶-methyl[1,2,5]oxadiazolo[3,4-b]pyrazine-5,6-diamine (7a);
N⁵-ethyl-N⁶-(2-fluorophenyl)-[1,2,5]oxadiazolo[3,4-b]pyrazine-5,6-diamine (7b);
N⁵-(2-fluorophenyl)-N⁶-propyl[1,2,5]oxadiazolo[3,4-b]pyrazine-5,6-diamine (7c);
N⁵-(2-fluorophenyl)-N⁶-(3,3,3-trifluoropropyl)-[1,2,5]oxadiazolo[3,4-b]pyrazine-5,6-diamine (7d);
N⁵-(2-fluorophenyl)-N⁶-(1-methylpiperidin-4-yl)-[1,2,5]oxadiazolo[3,4-b]pyrazine-5,6-diamine (7e); or
N⁵-cyclohexyl-N⁶-(2-fluorophenyl)-[1,2,5]oxadiazolo[3,4-b]pyrazine-5,6-diamine (7f).

2. A pharmaceutical composition comprising the compound or pharmaceutically acceptable salt thereof of claim 1 as a first active agent, a pharmaceutically acceptable carrier, and optionally an additional active agent.

3. A method of therapeutically treating a condition responsive to mitochondrial uncoupling, comprising administering a therapeutically effective amount of the compound or pharmaceutically acceptable salt thereof of claim 1 to a patient in need of such treatment.

4. The method of claim 3, wherein the condition responsive to mitochondrial uncoupling is obesity, type II diabetes, fatty liver disease, insulin resistance, Parkinson's disease, ischemia reperfusion injury, heart failure, non-alcoholic fatty liver disease (NALFD), or non-alcoholic steatohepatitis (NASH).

5. A method of regulating glucose homeostasis or insulin action in a patient comprising administering a therapeutically effective amount of the compound or pharmaceutically acceptable salt thereof of claim 1 to a patient in need thereof.

6. A compound of the formula:

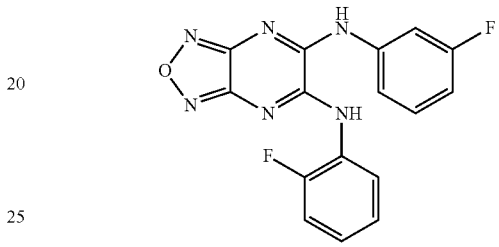

or a pharmaceutically acceptable salt thereof.

7. A pharmaceutical composition comprising the compound of claim 6 or a pharmaceutically acceptable salt thereof, and a pharmaceutically acceptable carrier.

8. A method of therapeutically treating a condition responsive to mitochondrial uncoupling, comprising administering a therapeutically effective amount of the compound or pharmaceutically acceptable salt thereof of claim 6 to a patient in need of such treatment.

9. The method of claim 8, wherein the condition responsive to mitochondrial uncoupling is obesity, type II diabetes, fatty liver disease, insulin resistance, Parkinson's disease, ischemia reperfusion injury, heart failure, non-alcoholic fatty liver disease (NALFD), or non-alcoholic steatohepatitis (NASH).

10. The method of claim 8, wherein the condition responsive to mitochondrial uncoupling is non-alcoholic steatohepatitis (NASH).

11. A method of regulating glucose homeostasis or insulin action in a patient comprising administering a therapeutically effective amount of the compound or pharmaceutically acceptable salt thereof of claim 6 to the patient.

* * * * *